US007169786B2

(12) United States Patent
Andrés-Gil et al.

(10) Patent No.: US 7,169,786 B2
(45) Date of Patent: Jan. 30, 2007

(54) ISOXAZOLINE DERIVATIVES AS ANTI-DEPRESSANTS

(76) Inventors: José Ignacio Andrés-Gil, Janssen-Cilag, S.A., Edificio Johnson & Johnson, Paseo de las Doce Estrellas, 5-7, Campo de las Naciones, 28042 Madrid (ES); Francisco Javier Fernández-Gadea, Janssen-Cilag, S.A., Edificio Johnson & Johnson, Paseo de las Doce Estrellas, 5-7, Campo de las Naciones, 28042 Madrid (ES); Manuel Jesús Alcázar-Vaca, Janssen-Cilag, S.A., Edificio Johnson & Johnson, Paseo de las Doce Estrellas, 5-7, Campo de las Naciones, 28042 Madrid (ES); José Maria Cid-Nuñez, Janssen-Cilag, S.A., Edificio Johnson & Johnson, Paseo de las Doce Estrellas, 5-7, Campo de las Naciones, 28042 Madrid (ES); Joaquin Pastor-Fernandez, Janssen-Cilag, S.A., Edificio Johnson & Johnson, Paseo de las Doce Estrellas, 5-7, Campo de las Naciones, 28042 Madrid (ES); Antonius Adrianus Hendrikus Petrus Megens, Janssen Pharmaceutica N.V., Turnhoutseweg 30, 2340 Beerse (BE); Godelieve Irma Christine Maria Heylen, Janssen Pharmaceutica N.V., Turnhoutseweg 30, 2340 Beerse (BE); Xavier Jean Michel Langlois, Janssen Pharmaceutica N.V., Turnhoutseweg 30, 2340 Beerse (BE); Margaretha Henrica Maria Bakker, Janssen Pharmaceutica N.V., Turnhoutseweg 30, 2340 Beerse (BE); Thomas Horst Wolfgang Steckler, Janssen Pharmaceutica N.V., Turnhoutseweg 30, 2340 Beerse (BE)

( * ) Notice: Subject to any disclaimer, the term of this patent is extended or adjusted under 35 U.S.C. 154(b) by 0 days.

(21) Appl. No.: 10/468,555

(22) PCT Filed: Feb. 13, 2002

(86) PCT No.: PCT/EP02/01567

§ 371 (c)(1),
(2), (4) Date: Aug. 21, 2003

(87) PCT Pub. No.: WO02/066484

PCT Pub. Date: Aug. 29, 2002

(65) Prior Publication Data
US 2004/0122037 A1 Jun. 24, 2004

(30) Foreign Application Priority Data
Feb. 21, 2001 (EP) .................. 01200611
Apr. 5, 2001 (EP) .................. 01201264

(51) Int. Cl.
A61K 31/496 (2006.01)
A61K 31/454 (2006.01)
C07D 498/04 (2006.01)
C07D 498/14 (2006.01)

(52) U.S. Cl. .................. 514/253.03; 514/254.04; 514/293; 514/321; 544/361; 544/368; 546/83; 546/198

(58) Field of Classification Search ............... 544/361, 544/368; 546/83, 198; 514/253.03, 254.04, 514/293, 321
See application file for complete search history.

(56) References Cited

U.S. PATENT DOCUMENTS 5,880,121 A * 3/1999 Hrib .................. 514/218

(Continued)

FOREIGN PATENT DOCUMENTS

EP 0 361 577 B1 4/1990

OTHER PUBLICATIONS

Berger, U.V. et al., "Depletion of Serotonin Using p-Chlorophenylalanine (PCPA) and Reserpine Protects against the Neurotoxic Effects of p-Chloroamphetamine (PCA) in the Brain", *Experimental Neurology.*, 1989, 103,111-115.

(Continued)

*Primary Examiner*—Emily Bernhardt

(57) ABSTRACT

The invention concerns substituted isoxazolines derivatives according to Formula (I): wherein X=CH?2#191, N—R$_7$, S or O, R$_1$, R$_2$ and R$_3$ are certain specific substituents, Pir is an optionally substituted piperidyl or piperazyl radical and R3 represents an optionally substituted aromatic homocyclic or heterocyclic ring system including a partially or completely hydrogenated hydrocarbon chain of maximum 6 atoms long with which the ring system is attached to the Pir radical and which may contain one or more heteroatoms selected from the group of O, N and S; a process for their preparation, pharmaceutical compositions comprising them and their use as a medicine, in particular for the treatment of depression and/or anxiety and disorders of body weight. The compounds according to the invention have surprisingly been shown to have a serotonine (5-HT) reuptake inhibitor activity in combination with additional α2-adrenoceptor antagonist activity and show a strong anti-depressant activity without being sedative. Compounds according to the invention are also suitable for treating patients with anxiety disorders and disorders of body weight. The invention also relates to novel combination of substituted isoxazolines derivatives having anti-depressant activity and/or anxiolytic activity and/or body weight control activity with antidepressants, anxiolytics and/or antipsychotics to improve efficacy and/or onset of action (I)

16 Claims, No Drawings

U.S. PATENT DOCUMENTS 6,583,141 B1 * 6/2003 Freyne et al. ............ 514/236.8

OTHER PUBLICATIONS

Eichinger, K. et al., "A Convenient Synthesis of 3- and 3,4-Substituted 4,5-Dihydroisoxazole-5-Acetic Acids", *Synthetic Communications*, 1997, 27(16), 2733-2742.

Fuller, R.W. et al., "Reversible and Irreversible Phases of Serotonin Depletion by 4-Chloroamphetamine", *European Journal of Pharmacology.*, 1975, 33, 119-124.

Janssen, P.A.J. et al., "Pharamacology of Risperidone (R 64 766 ), a New Antipsychotic with Serotonin-S2 and Dopamine-D2 Antagonistic Properties", *The Journal of Pharmacology Experimental Therapeutics*, 1988, 244, 685-693.

Lassen, J.B., "Influence of the New 5-Ht-Uptake Inhibitor Paroxetine on Hypermotility in Rats Produced by p-Chloroamphetamine (PCA) and 4-α-Dimethyl-m-Tyramine (H/77/77)", *Psychopharmacology*, 1978, 57, 151-153.

* cited by examiner

ISOXAZOLINE DERIVATIVES AS ANTI-DEPRESSANTS

This application is a 371 filing of PCT/EP02/01567, filed Feb. 13, 2002, which claims priority benefit from European application EP 01200611.0, filed Feb. 21, 2001 and EP 01201264.7, filed Apr. 5, 2001. The present application claims benefit of and priority from all these previously filed patent applications.

The invention concerns substituted isoxazolines derivatives having anti-depressant activity and/or anxiolytic activity and/or body weight control activity, processes for their preparation, pharmaceutical compositions comprising them and their use as a medicine, in particular for the treatment of depression, anxiety, stress-related disorders associated with depression and/or anxiety and disorders of body weight including anorexia nervosa and bulimia.

The invention also relates to novel combination of substituted isoxazolines derivatives having anti-depressant activity and/or anxiolytic activity and/or body weight control activity with antidepressants, anxiolytics and/or antipsychotics.

Tetrahydronaphtalene and indane derivatives showing anti-depressant activity are known from EP-361 577 B 1. These compounds are typical monoamine reuptake blockers with additional $\alpha_2$-adrenoceptor antagonist activity and they show anti-depressant activity without being sedative.

The problems associated with the compounds according to the state of the art is that the compounds cause considerable side-effects, such as nausea, excitation, an increased heart rate and a reduced sexual function. Furthermore, it requires a long time, in particular 3–4 weeks, before the response starts.

The purpose of the present invention is to provide novel compounds derivatives having anti-depressant and/or anxiolytic and/or body weight control activity, in particular compounds that do not exhibit the aforementioned disadvantages.

The present invention relates to novel isoxazoline derivatives according to the general Formula (I)

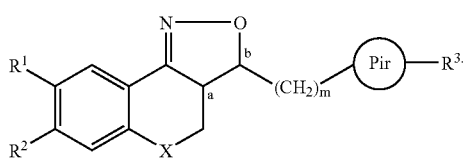

the pharmaceutically acceptable acid or base addition salts thereof, the stereochemically isomeric forms thereof and the N-oxide form thereof, wherein:

X is $CH_2$, N—$R^7$, S or O;

$R^7$ is selected from the group of hydrogen, alkyl, phenyl, phenylalkyl, alkylcarbonyl, alkyloxycarbonyl and mono- and dialkylaminocarbonyl, the phenyl and alkyl groups being optionally substituted with one or more halo atoms;

$R^1$ and $R^2$ are each, independently from each other, selected from the group of hydrogen, hydroxy, cyano, halo, $OSO_2H$, $OSO_2CH_3$, phenyl, phenylalkyl, alkyloxy, alkyloxyalkyloxy, alkyloxyalkyloxyalkyloxy, tetrahydrofuranyloxy, alkylcarbonyloxy, alkylthio, alkyloxyalkylcarbonyloxy, pyridinylcarbonyloxy, alkylcarbonyloxyalkyloxy, alkyloxycarbonyloxy, alkenyloxy, alkenylcarbonyloxy and mono- and dialkylaminoalkyloxy, the alkyl and aryl radicals being optionally substituted with one or more hydroxy or halo atoms or amino groups; or $R^1$ and $R^2$ may be taken together to form a bivalent radical —$R^1$—$R^2$— selected from the group of —$CH_2$—$CH_2$—O—, —O—$CH_2$—$CH_2$—, —O—$CH_2$—O—, —$CH_2$—O—$CH_2$— and —O—$CH_2$—$CH_2$—O—;

a and b are asymmetric centers;

$(CH_2)_m$ is a straight hydrocarbon chain of m carbon atoms, m being an integer ranging from 1 to 4;

Pir is an optionally substituted radical according to any one of Formula (IIa), (IIB or (IIc)

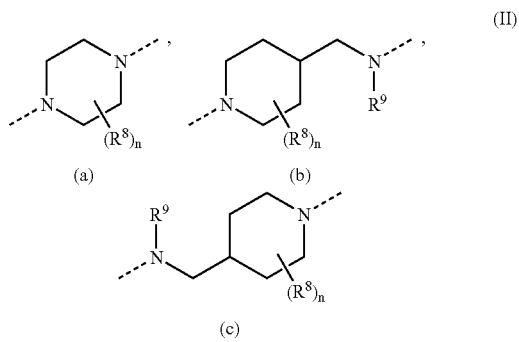

wherein:

each $R^8$ is independently from each other, selected from the group of hydrogen, hydroxy, amino, nitro, cyano, halo and alkyl;

n is an integer ranging from 1 to 5;

$R^9$ is selected from the group of hydrogen, alkyl and formyl; and $R^3$ represents an optionally substituted aromatic homocyclic or heterocyclic ring system together with an optionally substituted and partially or completely hydrogenated hydrocarbon chain of 1 to 6 atoms long with which said ring system is attached to the Pir radical and of which may contain one or more heteroatoms selected from the group of O, N and S.

More in particular, the invention relates to compounds according to Formula (I) wherein $R^3$ is a radical according to any one of Formula (IIIa), (IIIb) and (IIIc)

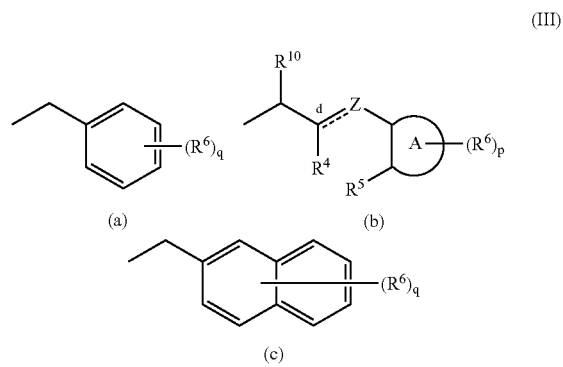

wherein:

d is a single bond while Z is a bivalent radical selected from the group of —$CH_2$—, —C(=O)—, —CH(OH)—, —C(=N—OH)—, —CH(alkyl)-, —O—, —S—, —S(=O), —NH— and —SH—; or d is a double bond while Z is a trivalent radical of formula =CH— or =C(alkyl)-;

A is a 5- or 6-membered aromatic homocyclic or heterocyclic ring, selected from the group of phenyl, pyranyl, pyridinyl, pyrazinyl, pyrimidinyl, pyridazinyl, thienyl, isothiazolyl, pyrrolyl, imidazolyl, pyrazolyl, furanyl, oxadiazolyl and isoxazolyl;

p is an integer ranging from 0 to 4;

q is an integer ranging from 0 to 7;

$R^4$ is selected from the group of hydrogen, alkyl, phenyl, biphenyl, naphthyl, halo and cyano, the alkyl and aryl radicals being optionally substituted with one or more hydroxy or halo atoms or amino groups;

$R^5$ is equal to $R^4$; or $R^4$ and $R^5$ may be taken together to form a bivalent radical —$R^4$—$R^5$— selected from the group of —$CH_2$—, =CH—, —$CH_2$—$CH_2$—, —CH=CH—, —O—, —NH—, =N—, —S—, —$CH_2$N(-alkyl)-, —CH=N—, —$CH_2$O— and —$OCH_2$—;

each $R^6$ is independently from each other, selected from the group of hydrogen, hydroxy, amino, nitro, cyano, halo, carboxyl, alkyl, phenyl, alkyloxy, phenyloxy, alkylcarbonyloxy, alkyloxycarbonyl, alkylthio, mono- and dialkylamino, alkylcarbonylamino, mono- and dialkylaminocarbonyl, mono- and dialkylaminocarbonyloxy, mono- and dialkylaminoalkyloxy, the alkyl and aryl radicals being optionally substituted with one or more hydroxy or halo atoms or amino groups; or two vicinal radicals $R^6$ may be taken together to form a bivalent radical —$R^6$—$R^6$— selected from the group of —$CH_2$—$CH_2$—O—, —O—$CH_2$—$CH_2$—, —O—$CH_2$—C(=O)—, —O—$CH_2$—O—, —$CH_2$—O—$CH_2$—, —O—$CH_2$—$CH_2$—O—, —CH=CH—CH=CH—, —CH=CH—CH=N—, —CH=CH—N=CH—, —CH=N—CH=CH—, —N=CH—CH=CH—, —$CH_2$—$CH_2$—$CH_2$—, —$CH_2$—$CH_2$—C(=O)— and —$CH_2$—$CH_2$—$CH_2$—$CH_2$—; and $R^{10}$ is selected from the group of hydrogen, alkyl, phenylalkyl and phenyl.

Preferably, the invention relates to those compounds wherein X=O or NH; $R^1$ and $R^2$ are both alkyloxy ; m=1; Pir is a radical according to Formula (IIa) wherein $R^8$ is hydrogen and n=4; $R^3$ is a radical according to Formula (IIIb) wherein Z is =CH—, d is a double bond, A is a phenyl ring, $R^4$ is an alkyl and $R^{10}$ is hydrogen.

More preferably, the invention relates to compounds where X=O, $R^1$ and $R^2$ are both methoxy ; m=1; Pir is a radical according to Formula (IIa) wherein $R^8$ is hydrogen and n=4; $R^3$ is a radical according to Formula (IIIb) wherein Z is =CH—, d is a double bond, A is a phenyl ring, $R^4$ is methyl and $R^{10}$ is hydrogen In the framework of this application, alkyl defines straight or branched saturated hydrocarbon radicals having from 1 to 6 carbon atoms, for example methyl, ethyl, propyl, butyl, 1-methylpropyl, 1,1-dimethylethyl, pentyl, hexyl; or alkyl defines cyclic saturated hydrocarbon radicals having from 3 to 6 carbon atoms, for example cyclopropyl, methylcyclopropyl, cyclobutyl, cyclopentyl and cyclohexyl. Halo is generic to fluoro, chloro, bromo and iodo. Alkyl radicals being optionally substituted with one or more halo atoms are for example polyhaloalkyl radicals, for example difluoromethyl and trifluoromethyl.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to Formula (I) containing acidic protons may also be converted into their therapeutically active non-toxic metal or amine addition salts forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate base or acid.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more nitrogens of the piperazinyl radical are N-oxidized.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*]. If "α" and "β" are used : the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds of Formula (I)) relative to the position of the highest priority substituent on the reference atom is denominated "α", if it is on the same side of the mean plane determined by the ring system, or "β", if it is on the other side of the mean plane determined by the ring system.

Compounds of Formula (I) and some of the intermediates have at least two stereogenic centers in their structure, respectively denoted a and b in Formula (I). Due to the synthetic pathway followed for the synthesis of the tricyclic system, the configuration of those two asymmetric centers a and b is predetermined, so that the relative configuration of center a is S* and of center b is R*.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems*, 1985, pp. 112–176, and *Drugs*, 1985, 29, pp. 455–473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the formula —COOR$^x$, where R$^x$ is a C$_{1-6}$alkyl, phenyl, benzyl or one of the following groups:

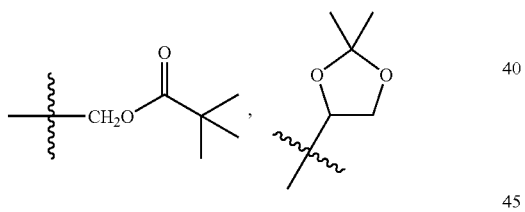

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The compounds according to the invention have surprisingly been shown to have selective serotonine (5-HT) reuptake inhibitor activity in combination with additional α$_2$-adrenoceptor antagonist activity and show a strong antidepressant and/or anxiolytic activity and/or a body weight control activity without being sedative. Also, in view of their selective serotonine (5-HT) reuptake inhibitor as well as α$_2$-adrenoceptor antagonist activity, compounds according to the invention are also suitable for treatment and/or prophylaxis in diseases where either one of the activities alone or the combination of said activities may be of therapeutic use. In particular, the compounds according to the invention may be suitable for treatment and/or prophylaxis in the following diseases:

Central nervous system disorders, including:
Mood disorders, including particularly major depressive disorder, depression with or without psychotic features, catatonic features, melancholic features, atypical features of postpartum onset and, in the case of recurrent episodes, with or without seasonal pattern, dysthymic disorder, bipolar I disorder, bipolar II disorder, cyclothymic disorder,-recurrent brief depressive disorder, mixed affective disorder, bipolar disorder not otherwise specified, mood disorder due to a general medical condition, substance-induced mood disorder, mood disorder not otherwise specified, seasonal affective disorder and premenstrual dysphoric disorders.

Anxiety disorders, including panic attack, agoraphobia, panic disorder without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

Stress-related disorders associated with depression and/or anxiety, including acute stress reaction, adjustment disorders (brief depressive reaction, prolonged depressive reaction, mixed anxiety and depressive reaction, adjustment disorder with predominant disturbance of other emotions, adjustment disorder with predominant disturbance of conduct, adjustment disorder with mixed disturbance of emotions and conduct, adjustment disorders with other specified predominant symptoms) and other reactions to severe stress.

Dementia, amnesic disorders and cognitive disorders not otherwise specified, especially dementia caused by degenerative disorders, lesions, trauma, infections, vascular disorders, toxins, anoxia, vitamin deficiency or endocrinic disorders, or amnesic disorders caused by alcohol or other causes of thiamin deficiency, bilateral temporal lobe damage due to Herpes simplex encephalitis and other limbic encephalitis, neuronal loss secondary to anoxia/hypoglycemia/severe convulsions and surgery, degenerative disorders, vascular disorders or pathology around ventricle III.

Cognitive disorders due to cognitive impairment resulting from other medical conditions.

Personality disorders, including paranoid personality disorder, schizoid personality disorder, schizotypical personality disorder, antisocial personality disorder, borderline personality disorder, histrionic personality disorder, narcissistic personality disorder, avoidant personality disorder, dependent personality disorder, obsessive-compulsive personality disorder and personality disorder not otherwise specified.

Schizoaffective disorders resulting from various causes, including schizoaffective disorders of the manic type, of the depressive type, of mixed type, paranoid, disorganized, catatonic, undifferentiated and residual schizophrenia, schizophreniform disorder, schizoaffective disorder, delusional disorder, brief psychotic disorder, shared psychotic disorder, substance-induced psychotic disorder and psychotic disorder not otherwise specified.

Akinesia, akinetic-rigid syndromes, dyskinesia and medication-induced parkinsonism, Gilles de la Tourette syndrome and its symptoms, tremor, chorea, myoclonus, tics and dystonia.

Attention-deficit/hyperactivity disorder (ADHD).

Parkinson's disease, drug-induced Parkinsonism, post-encephalitic Parkinsonism, progressive supranuclear palsy, multiple system atrophy, corticobasal degeneration, parkinsonism-ALS dementia complex and basal ganglia calcification.

Dementia of the Alzheimer's type, with early or late onset, with depressed mood.

Behavioral disturbances and conduct disorders in dementia and the mentally retarded, including restlessness and agitation.

Extra-pyramidal movement disorders.

Down's syndrome.

Akathisia.

Eating Disorders, including anorexia nervosa, atypical anorexia nervosa, bulimia nervosa, atypical bulimia nervosa, overeating associated with other psychological disturbances, vomiting associated with other psychological disturbances and non-specified eating disorders.

AIDS-associated dementia.

Chronic pain conditions, including neuropathic pain, inflammatory pain, cancer pain and post-operative pain following surgery, including dental surgery. These indications might also include acute pain, skeletal muscle pain, low back pain, upper extremity pain, fibromyalgia and myofascial pain syndromes, orofascial pain, abdominal pain, phantom pain; tic douloureux and atypical face pain, nerve root damage and arachnoiditis, geriatric pain, central pain and inflammatory pain.

Neurodegenerative diseases, including Alzheimer's disease, Huntington's chorea, Creutzfeld-Jacob disease, Pick's disease, demyelinating disorders, such as multiple sclerosis and ALS, other neuropathies and neuralgia, multiple sclerosis, amyotropical lateral sclerosis, stroke and head trauma.

Addiction disorders, including:
Substance dependence or abuse with or without physiological dependence, particularly where the substance is alcohol, amphetamines, amphetamine-like substances, caffeine, cannabis, cocaine, hallucinogens, inhalants, nicotine, opioids, phencyclidine, phencyclidine-like compounds, sedative-hypnotics, benzodiazepines and/or other substances, particularly useful for treating withdrawal from the above substances and alcohol withdrawal delirium.

Mood disorders induced particularly by alcohol, amphetamines, caffeine, cannabis, cocaine, hallucinogens, inhalants, nicotine, opioids, phencyclidine, sedatives, hypnotics, anxiolytics and other substances.

Anxiety disorders induced particularly by alcohol, amphetamines, caffeine, cannabis, cocaine, hallucinogens, inhalants, nicotine, opioids, phencyclidine, sedatives, hypnotics, anxiolytics and other substances and adjustment disorders with anxiety.

Smoking cessation.

Body weight control, including obesity.

Sleep disorders and disturbances, including
Dyssomnias and/or parasomnias as primary sleep disorders, sleep disorders related to another mental disorder, sleep disorder due to a general medical condition and substance-induced sleep disorder.

Circadian rhythms disorders.

Improving the quality of sleep.

Sexual dysfunction, including sexual desire disorders, sexual arousal disorders, orgasmic disorders, sexual pain disorders, sexual dysfunction due to a general medical condition, substance-induced sexual dysfunction and sexual dysfunction not otherwise specified.

The present invention thus also relates to compounds of Formula (I) as defined hereinabove, the pharmaceutically acceptable acid or base addition salts thereof, the stereochemically isomeric forms thereof, the N-oxide form thereof, as well as the pro-drugs thereof for use as a medicine. Further, the present invention also relates to the use of a compound of Formula (I), the pharmaceutically acceptable acid or base addition salts thereof, the stereochemically isomeric forms thereof, the N-oxide form thereof as well as the pro-drugs thereof for the manufacture of a medicament for treating depression, anxiety and body weight disorders or more generally any one of the diseases mentioned above.

The compounds according to the invention may also be suitable as add-on treatment and/or prophylaxis in the above listed diseases in combination with antidepressants, anxiolytics and/or antipsychotics which are currently available or in development or which will become available in the future, to improve efficacy and/or onset of action. This is evaluated in rodent models in which antidepressants, anxiolytics and/or antipsychotics are shown to be active. For example, compounds are evaluated in combination with antidepressants, anxiolytics and/or antipsychotics for attenuation of stress-induced hyperthermia.

The invention therefore also relates to a pharmaceutical composition comprising the compounds according to the invention and one or more other compounds selected from the group of antidepressants, anxiolytics and antipsychotics as well as to the use of such a composition for the manufacture of a medicament to improve efficacy and/or onset of action in the treatment of depression and/or anxiety.

In vitro receptor and neurotransmitter transporter binding and signal-transduction studies can be used to evaluate the $\alpha_2$-adrenoceptor antagonism activity and serotonine (5-HT) reuptake inhibitor activity of the present compounds. As indices for central penetration and potency to block the $\alpha_2$-adrenoceptors and serotonin transporters, respectively, ex vivo α$_2$-adrenoceptor and serotonin transporter occupancy can be used. As indices of α$_2$-adrenoceptor antagonism-in vivo, the reversal of the loss of righting reflex, observed in rats after subcutaneous injection or oral dosage of the compound before intravenous medetomidine administration in rats can-be used (medetomidine-test). As indices of serotonine (5-HT) reuptake inhibition activity, the inhibition of head-twitches and excitation in rats, observed after subcutaneous injection or oral dosage of the compound before subcutaneous p-chloroamphetamine administration in rats can be used (pCA-test).

The invention also relates to a composition comprising a pharmaceutically acceptable carrier and, as active ingredient, a therapeutically effective amount of a compound according to the invention. The compounds of the invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The compounds according to the invention can generally be prepared by a succession of steps, each of which is known to the skilled person.

In particular, the compounds according to Formula (I) with a Pir-radical according to Formula (IIa) can be prepared by a nucleophilic substitution reaction with a substituted piperazine according to Formula (V) on an intermediate of Formula (IV). These reactions may be carried out in a reaction inert solvent such as dioxane, methylisobutylketone or N,N'-dimethylformamide, in the presence of a suitable base such as potassium carbonate, sodium carbonate or triethylamine, or even without a base, using in this latter case excess of reagent of Formula (V). Convenient reaction temperatures range between 100° C. and 150° C.

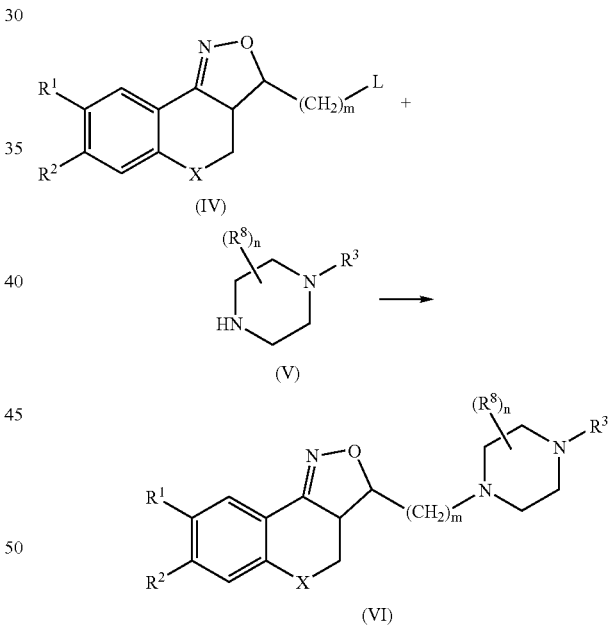

In compound (IV), L represents any suitable reactive leaving group, in particular halo, such as chloro, bromo or iodo or sulfonyloxy, such as methylsulphonyloxy or 4-methylbenzenesulfonyloxy.

The compounds according to Formula (I) with a Pir-radical according to Formula (IIa) can also be prepared by a 2-step reaction scheme in which an intermediate of Formula (IV) is first reacted with a substituted piperazine according to Formula (VII) after which the R$^3$-radical is introduced into the molecule. Reaction conditions are similar to those described above for compounds of Formula (VI).

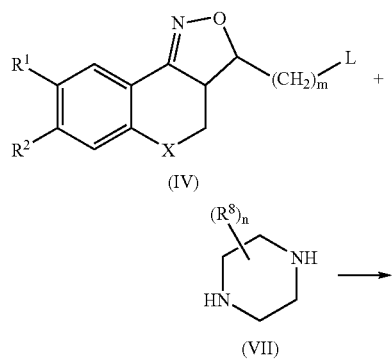

(step 1)

(IV)

(VII)

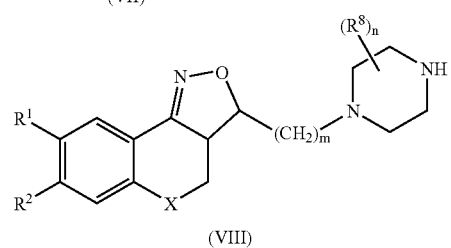

(VIII)

In compound (IV), L represents any suitable reactive leaving group, in particular halo, such as chloro, bromo or iodo or sulfonyloxy, such as methylsulphonyloxy or 4-methylbenzenesulfonyloxy.

In intermediate compound (VII), one of the nitrogen function may also be protected, e.g. by a tert-butyloxycarbonyl-group.

(step 2)

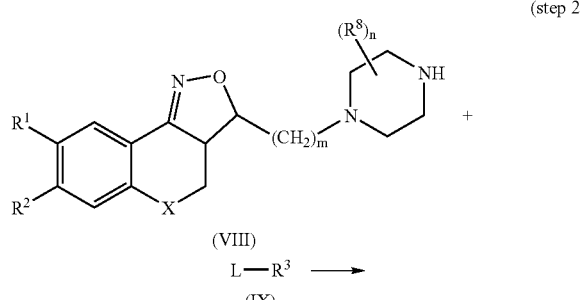

(VIII)

L—R³ ⟶

(IX)

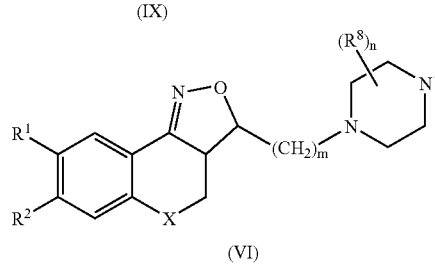

(VI)

In compound (IX), L represents any suitable reactive leaving group, in particular halo, such as chloro, bromo or iodo or sulfonyloxy, such as methylsulphonyloxy or 4-methylbenzenesulfonyloxy. Also R³–CHO may be used as compound (IX).

The compounds according to Formula (I) with a Pir-radical according to Formula (IIa) can also be prepared by a 2-step reaction scheme in which an intermediate of Formula (VIII) is reacted with an acid according to Formula (X), followed by a subsequent reduction of the carbonyl-function of intermediate (XI). Reactions of step 1 may be carried out in a reaction inert solvent, such as chloroform, dichloromethane, tetrahydrofuran, dimethylformamide or a mixture thereof, using any of methods known to a person skilled in the art using condensation reagents such as 1,1'-carbonyldiimidazole, N,N'-dicyclohexylcarbodiimide or by previous transformation of carboxylic acid of Formula (X) into its corresponding acid chloride. Reactions shown in step 2 can be performed using a suitable reducing agent, such as lithium-aluminum hydride or aluminum hydride, in a suitable solvent, for example tetrahydrofuran. Generally, these reactions are run at a temperature ranging between −20° C. and room temperature.

(step 1)

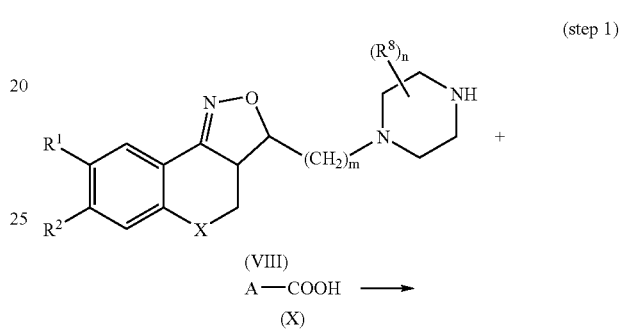

(VIII)

A—COOH ⟶

(X)

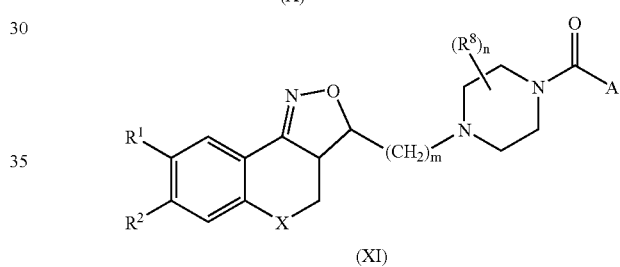

(XI)

(step 2)

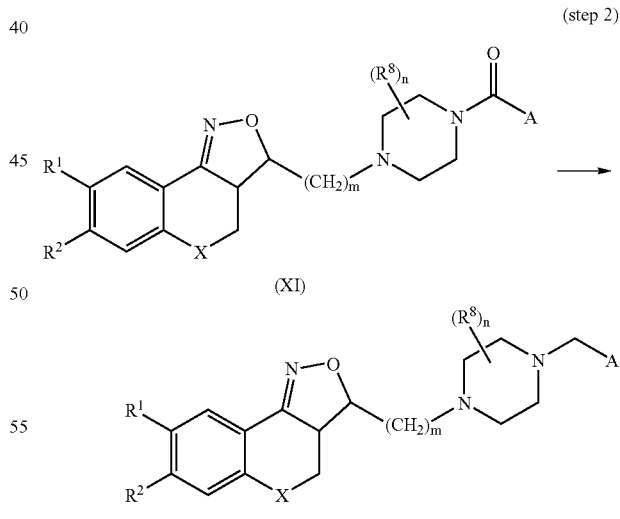

R³ = CH₂A (XII)

In intermediate compounds (XI) and (XII), the A-group represents an optionally substituted aromatic homocyclic or heterocyclic ring system including a partially or completely hydrogenated hydrocarbon chain of maximum 5 atoms long of which one or more carbon atoms may be replaced by one or more atoms selected from the group of oxygen, nitrogen and sulphur, with which the ring system is attached to the Pir radical that has been defined above.

The substituents $R^1$ and $R^2$ may be changed or interconverted into each other by methods well known in the art, such as demethylation, acylation, esterification, amination and amidation.

The starting materials and some of the intermediates are compounds that are either commercially available or may be prepared according to conventional reaction procedures generally known in the art. For example, intermediates of Formula (IV) in which X=O may be prepared according to the following reaction scheme (Scheme 1):

Scheme 1

(step 1a)

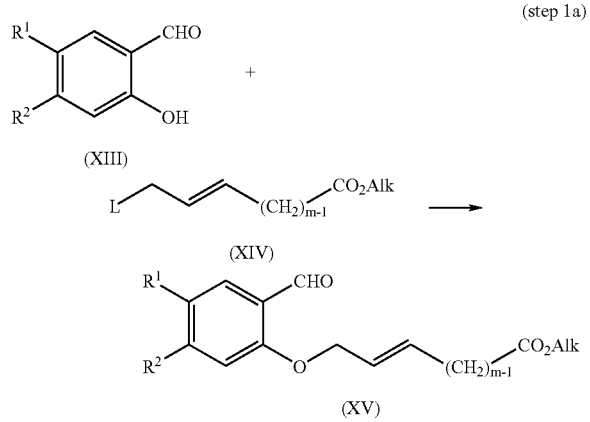

In intermediate compound (XIV), L represents any suitable reactive leaving group, in particular halo, such as chloro, bromo or iodo or sulfonyloxy, such as methylsulphonyloxy or 4-methylbenzenesulfonyloxy. Furthermore, Alk in intermediate compound (XIV) represents any $C_{1-6}$ alkyl-group, in particular an ethyl-group and m is defined as in Formula (I).

Intermediates according to Formula (IV) in which X=NH may also be prepared in an equivalent manner according to above step 1, provided that the intermediate compound (XIII) is replaced by its amine-analog (XVI), preferably with the amine group protected with e.g. a $COCF_3$— group. The alkylation step may be carried out in a reaction inert solvent, for example, tetrahydrofuran or dimethylformamide, in the presence of a strong base, such as sodium or potassium hydride, and the addition of a crown-ether, such as 18-crown-6 or 15crown-5. Convenient reaction temperatures range between room temperature and 60° C.

(step 1b)

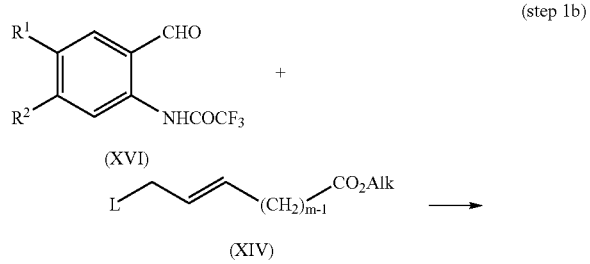

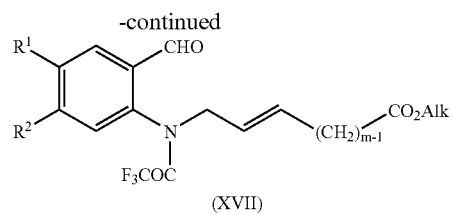

(step 2)

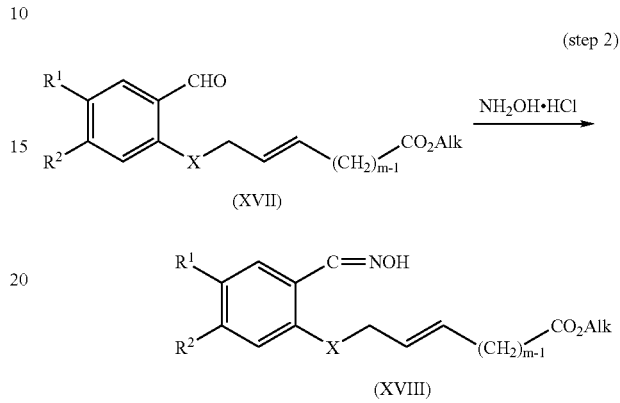

Intermediates of Formula (XVII) are converted to oximes of Formula (XVII) using art-known techniques, such as using hydroxylamine hydrochloride in the presence of $NaHCO_3$ or pyridine in a reaction inert solvent, for example ethanol. Intermediate (XVIII) is oxidized to its nitril oxide and undergoes in situ an intramolecular cycloaddition, yielding compound of Formula (XIX). This oxidation can be carried out using a sodium hypochlorite solution in the presence of triethylamine in an inert solvent such as dichloromethane at room temperature. Oxidation can also be performed using Chloramine-T (N-chloro4-methyl-benzenesulfonamide, sodium salt), stirring and heating in a solvent such as refluxing ethanol. At this stage the two stereocenters a and b of Formula (I) are formed.

(step 3)

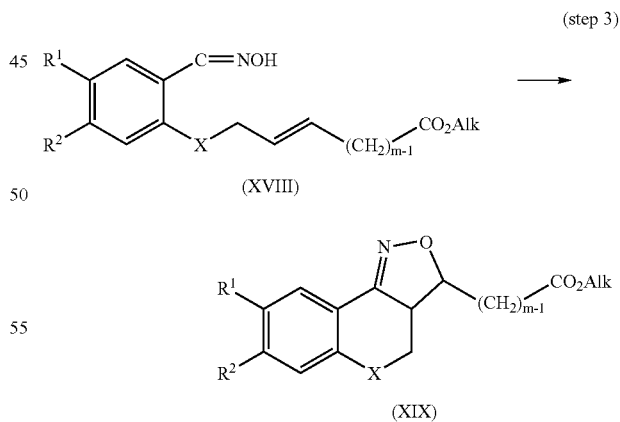

Preparation of a compound of Formula (XX) can be achieved using procedures known in the art, for instance by reduction of the carbonyl compound of Formula (XIX) in the presence of a suitable reducing agent, for example, sodiumborohydride in a suitable solvent, such as water, an alcohol, tetrahydrofuran or a mixture thereof, generally at room temperature.

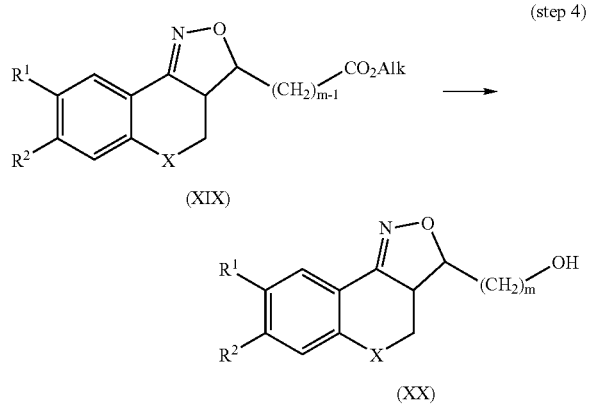

(XIX)

(XX)

Intermediate of Formula (IV) can be prepared from intermediate of Formula (XX) using standard techniques. Thus, reaction with methanesulfonyl chloride or 4-methylbenzenesulfonyl chloride in the presence of a base, such as triethylamine, in a reaction inert solvent, for example dichloromethane, at reaction temperatures ranging between 0° C. and room temperature, yields the corresponding sulfonyloxy derivative intermediate (IV). The corresponding halo-derivative can also be prepared, e.g. treating intermediate of Formula (XX) with triphenylphosphine, in the presence of tetrachloromethane, in a reaction inert solvent, such as tetrahydrofuran, stirring and refluxing the mixture.

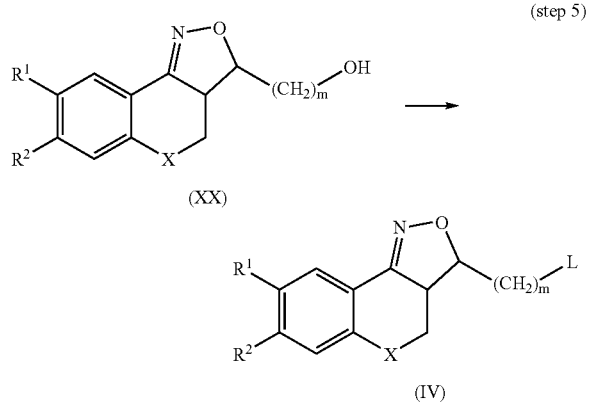

(XX)

(IV)

It is evident that in the foregoing and in the following reactions, the reaction products may be isolated from the reaction medium and, if necessary, further purified according to methodologies generally known in the art such as extraction, crystallization and chromatography. It is further evident that reaction products that exist in more than one enantiomeric form, may be isolated from their mixture by known techniques, in particular preparative chromatography, such as preparative HPLC. Typically, intermediate compounds (IV) and final compounds according to Formula (I) may be separated into their enantiomeric forms.

Compounds according to the invention in which $X=CH_2$ may be prepared according to the following reaction scheme (Scheme 2) in which an intermediary compound according to Formula (V) is first N-alkylated with a dihaloderivative of Formula (XX) using standard techniques, in the presence or absence of a base and in an inert reaction solvent, such as chloroform, dichloromethane or 1,2-dichloroethane, and at reaction temperatures ranging between room temperature and 80° C., yielding an intermediate of Formula (XXI). An aldehyde of Formula (XXII) was reacted with tert-butylamine in an aprotic solvent such as toluene, stirring and heating at reflux temperature with removal of water using a standard device, such as a Dean-Stark water separator, yielding an imine of Formula (XXIV). C-alkylation of intermediary compound of Formula (XXIV) with intermediate of Formula (XXI) can be achieved in the presence of an alkyl-lithium derivative, such as n-butyllithium, under an inert atmosphere and in a dry inert solvent, such as tetrahydrofuran, at low temperatures ranging between −78° C. and 0° C., yielding an intermediate of Formula (XXV). The intermediate compound of Formula (XXVI) may be prepared by reaction of compound of Formula (XXV) with hydroxylamine, in the presence of a base such as sodium bicarbonate, in a solvent such as a lower alkyl-alcohol like ethanol, generally at room temperature. Finally, the oxidation of the oxime derivative of Formula (XXVI) to its nitril oxide and subsequent in situ cycloaddition to give compound of Formula (XXVII), may be achieved by similar standard techniques such as those described above for intermediate of Formula (XVIII) to give compounds of Formula (XIX).

Schema 2

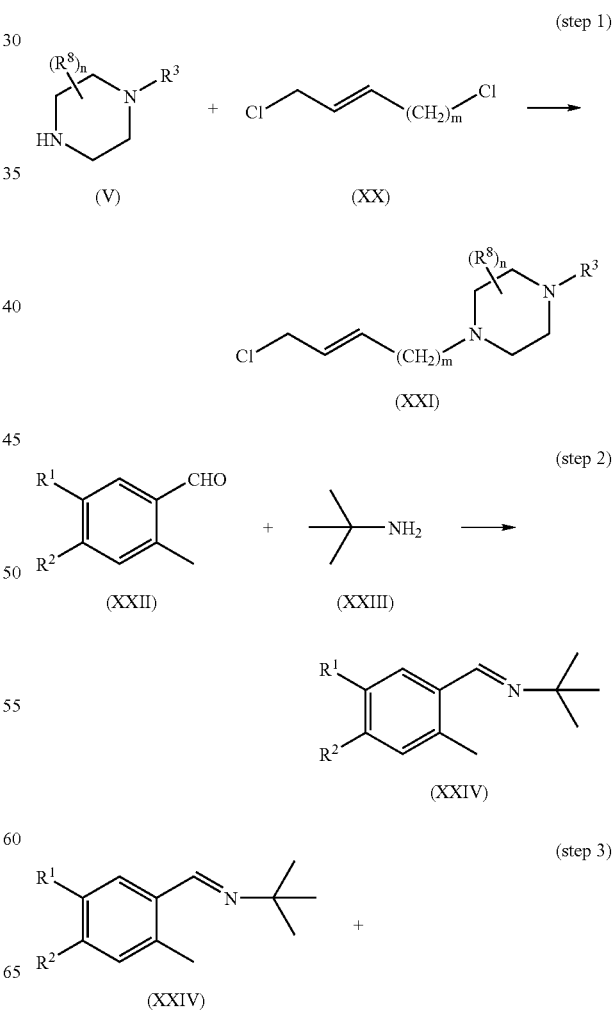

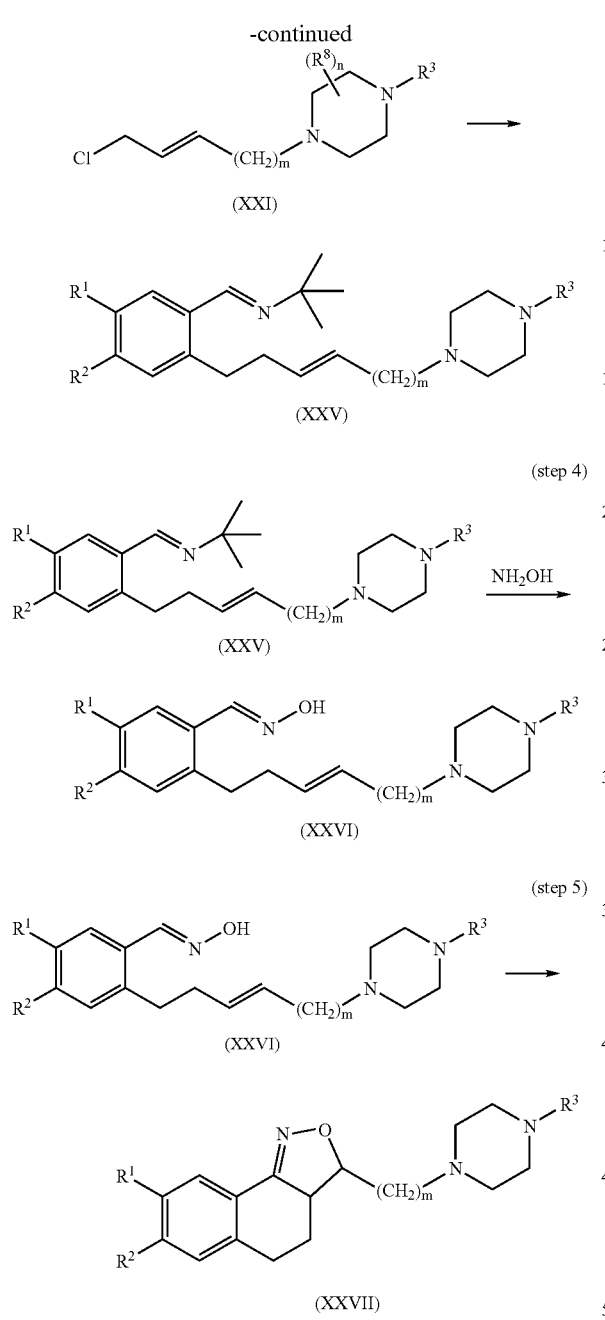

matory, analgesic and antipyretic compounds and is excluded from patent protection.

The following examples illustrate the present invention without being limited thereto.

EXPERIMENTAL PART

The carbon ring numbering system for the compounds according to Formula (I) used in this application is as follows:

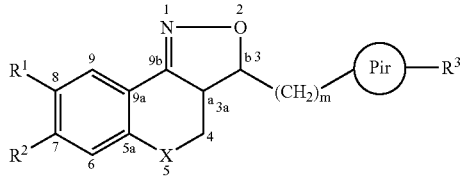

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction. The stereogenic centers a and b in Formula (I) have respectively the ring numbers 3a and 3.

Hereinafter, "DMF" is defined as N,N-dimethylformamide, "DIPE" is defined as diisopropyl ether, and "THF" is defined as tetrahydrofurane.

A. Preparation of the Intermediate Compounds

EXAMPLE A1.a

Preparation of Intermediate 1

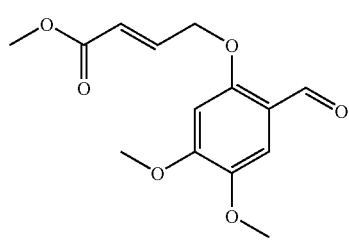

A solution of 4-bromo-2-butenoic acid methyl ester (0.1647 mol) in DMF (50 ml) was added dropwise to a mixture of 2-hydroxy-4,5-dimethoxy-benzaldehyde (0.0823 mol) and $K_2CO_3$ (0.1647 mol) in DMF (200 ml). The reaction mixture was stirred for 2 hours at room temperature, filtered and the filtrate was evaporated to dryness. The residue was washed in a 10% aqueous NaOH solution, then extracted with $CH_2Cl_2$. The separated organic layer was dried ($Na_2SO_4$), filtered, and the solvent was evaporated. The residue was washed with diethyl ether, then dried. Yielding: 20 g of intermediate 1 (87%).

It is evident that the reaction steps disclosed above may be adapted to the specific reaction products. The reaction steps disclosed may be performed in any way known to the skilled person, including in solution or as solid phase reactions, the latter during which the reaction products are bound to a resin material and are—in a final cleavage step—released from the resin material. Examples of such embodiments and adaptations have been disclosed by way of the Examples further in this application.

The compound 3,3a,4,5-tetrahydronaphto[1,2-c]isoxazole-3-acetic acid (Formula (IV) wherein each of $R^1$ and $R^2$ are H, m=0, X=$CH_2$ and L=COOH) and has been disclosed in Synthetic Communications, 27(16), 2733–2742 (1997) as an intermediate for the syntheses of anti-inflam-

EXAMPLE A1.b

Preparation of Intermediate 2

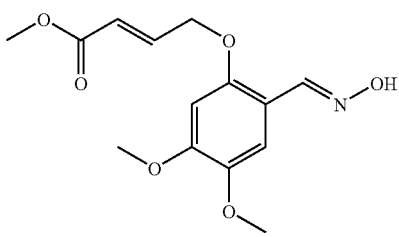

Hydroxylamine (0.045 mol) was added to a solution of intermediate 1 (0.041 mol) in ethanol (150 ml). Pyridine (57 ml) was added. The reaction mixture was stirred for 2 hours at room temperature, then poured out into water and acidified with concentrated HCl. This mixture was extracted with $CH_2Cl_2$. The separated organic layer was dried ($Na_2SO_4$), filtered, and the solvent was evaporated. Yielding: 11.7 g (96%, crude yield). A sample (2 g) was purified by high-performance liquid chromatography over silica gel (eluent: $CH_2Cl_2/CH_3OH$ 95/5). The pure fractions were collected and the solvent was evaporated. The residue was washed with diethyl ether, then dried. Yielding: 0.9 g intermediate 2.

EXAMPLE A1.c

Preparation of Intermediate 3

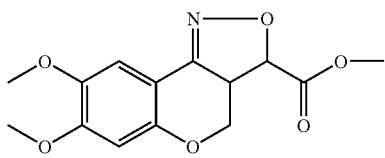

NaOCl, 5% (130 ml) was added dropwise to a mixture of intermediate 2 (0.037 mol) and $Et_3N$ (1 ml) in $CH_2Cl_2$ (220 ml). The reaction mixture was stirred for 4 hours at room temperature, then washed with water, dried ($Na_2SO_4$), filtered, and the filtrate was evaporated. The residue was purified by short open column chromatography over silica gel (eluent: $CH_2Cl_2$/2-propanone 100/0 and 95/5). The desired fractions were collected and the solvent was evaporated. Yielding: 5.8 g (54%, used in next traction step without further purification). A sample (2 g) was recrystallised from EtOAc. The precipitate was filtered off and dried. Yielding: 1.7 g of intermediate 3.

EXAMPLE A1.d

Preparation of Intermediate 4

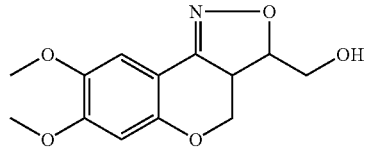

$NaBH_4$ (0.043 mol) was added portionwise to a solution of intermediate 3 (0.017 mol) in THF (50 ml) and $H_2O$ (5 ml), stirred and cooled on an ice-bath. The resulting reaction mixture was stirred for 2 hours at room temperature. 2-Propanone was added while stirring for 30 min. The reaction mixture was washed with water and extracted with $CH_2Cl_2$. The separated organic layer was washed with brine, dried ($Na_2SO_4$), filtered and the solvent evaporated. The residue was purified by short open column chromatography over silica gel (eluent: $CH_2Cl_2/CH_3OH$ 95/5) and by high-performance liquid chromatography over silica gel (eluent: $CH_2Cl_2/CH_3OH$ 98/2). The pure fractions were collected and the solvent was evaporated. A sample (1.8 g) was treated with diethyl ether, then dried. Yielding: 1.2 g of intermediate 4 (59%).

EXAMPLE A1.e

Preparation of Intermediate 5

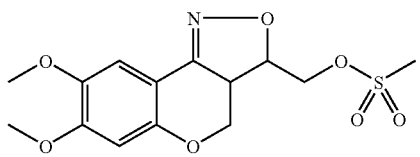

$Et_3N$ (0.016 mol) was added to a solution of intermediate 4 (prepared according to A3) (0.0109 mol) in $CH_2Cl_2$ (60 ml). The mixture was cooled in an ice-bath. Methanesulfonyl chloride (0.012 mol) was added and the resulting reaction mixture was stirred for 30 min. Then, the mixture was washed with water, dried ($Na_2SO_4$), filtered and the solvent was evaporated. Yielding: 3.5 g of intermediate 5 (82%, used in next reaction step without further purification).

EXAMPLE A1.f

Preparation of Intermediate 6

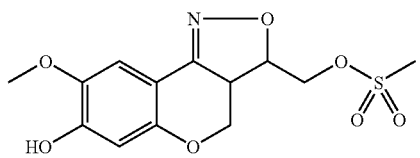

Reaction under $N_2$ atmosphere. $BBr_3$ (0.04368 mol) was added dropwise to a stirred solution of intermediate 5 (prepared according to A1.e) (0.00873 mol) in $CH_2Cl_2$ (100 ml), cooled to −78° C. The reaction mixture was allowed to warm to −40° C. and stirring was continued for 2 hours at −40° C. Then, the mixture was poured out into ice-water and extracted with CH₂Cl₂. The separated organic layer was dried (MgSO₄), filtered and the solvent evaporated. The residue was purified by flash column chromatography over silica gel (eluent: CH₂Cl₂/CH₃OH 97/3), then by HPLC (eluent: CH₂Cl₂/CH₃OH 99.5/0.5 to 90/10). Two product fraction groups were collected and their solvent was evaporated. Yield: 0.750 g of intermediate 6 (26%).

EXAMPLE A1.g

Preparation of Intermediate 7

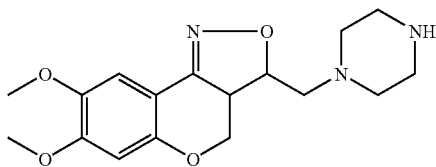

A mixture of intermediate 5 (prepared according A1d) (0.0422 mol) and piperazine (0.1267 mol) in 1,4-dioxane (15 ml) was stirred for 2 hours at 100° C. The solvent was evaporated. The residue was washed with water and extracted with CH₂Cl₂. The separated organic layer was dried (Na₂SO₄), filtered and the solvent was evaporated. Yielding: 13 g of intermediate 7 (NMR: 85%).

EXAMPLE A1.h

Preparation of Intermediate 8

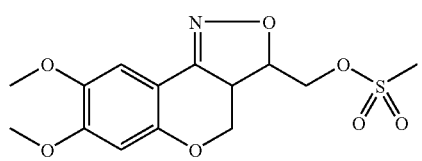

Intermediate 5 (prepared according to A1.e) (200 g, 0.58 mol) was separated into its enantiomers by chiral column chromatography over column LC110-2 with stationary phase CHMRALPAK-AD (2000 g, packing pressure: 45 bar, detector range: 2.56, wavelength: 240 nm, temperature: 30° C.; injection solution: 200 g in 8.4 L CH₃CN; then, 19.6 L methanol (+2% ethanol) was added, then filtered; injection-volume: 700 ml; eluent: CH₃OH/CH₃CN 70/30 v/v). Two product fraction groups were collected and their solvent was evaporated. Yield: 95 g of intermediate 8.

EXAMPLE A1.i

Preparation of Intermediate 9

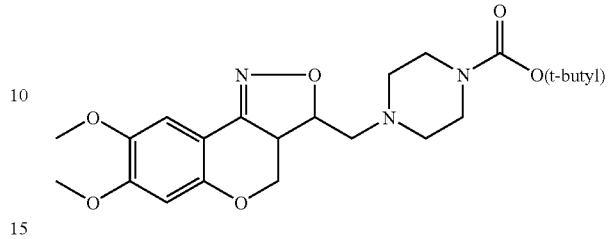

A mixture of intermediate 8 (prepared according A1.h) (0.0728 mol) and 1-(tert-butyloxycarbonyl)piperazine (0.087 mol) in dioxane (500 ml) was stirred and refluxed for 48 hours. The solvent was evaporated and CH₂Cl₂ was added. H₂O and NaOH (50%) were added also and the mixture was extracted with CH₂Cl₂. The separated organic layer was dried (MgSO₄) and the solvent was evaporated in vacuum. Yield intermediate 9

EXAMPLE A1.j

Preparation of Intermediate 10

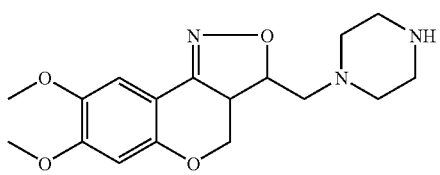

A mixture of intermediate 9 (0.00318 mol) and 2,2,2-trifluoroacetic acid (189 ml) in CH₂Cl₂ (500 ml) was stirred for 1 hour at room temperature. The solvent was evaporated and the residue was dissolved in CH₂Cl₂. NaOH (50%)was added and the mixture was extracted. The separated organic layer was dried(MgSO₄), filtered and the solvent was evaporated in vacuum. The residue was purified by short column chromatography over silica gel (eluent: CH₂Cl₂/(MeOH/NH₃) 100/0;95/5). The pure fractions were collected and the solvent was evaporated. Yield: 14.32 g of intermediate 10 (59%).

EXAMPLE A1.k

Preparation of Intermediate 11

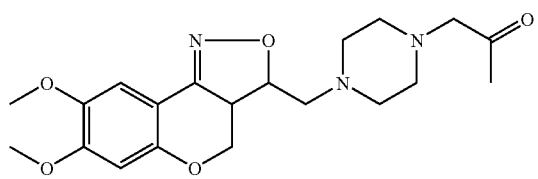

A mixture of intermediate 10 (0.00599 mol), 1-Chloro-2-propanone (0.00599 mol) and K₂CO₃ (0.01199 mol) in DMF (200 ml) was stirred for 24 hours at room temperature.

The solvent was evaporated. The residue was dissolved in CH₂Cl₂. The organic solution was washed with water, dried (MgSO₄), filtered and the solvent was evaporated in vacuo. Yield: (quantitative yield) of intermediate 11.

EXAMPLE A1.l

Preparation of Intermediate 12

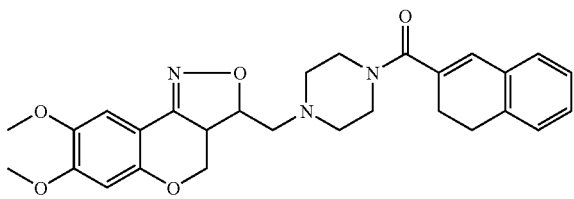

Reaction under N₂ atmosphere. A mixture of 3,4-Dihydro-2-naphthalenecarboxylic acid (0.0043 mol) and 1,1'-carbonylbis[1H-imidazole] (0.0047 mol) in CH₂Cl₂, dry was stirred for one hour at room temperature. A solution of intermediate 7 (prepared according to A1.g) (0.0043 mol) in CH₂Cl₂, dry was added and the resulting reaction solution was stirred for ±24 hours at room temperature. The solution was washed with water, then extracted with CH₂Cl₂. The separated organic layer was dried (Na₂SO₄), filtered and the solvent was evaporated. The residue was purified by short open column chromatography over silica gel (eluent: CH₂Cl₂/CH₃OH 97/3). The pure fractions were collected and the solvent was evaporated. Yield: 0.4 g of intermediate 12 (22%).

EXAMPLE A1.m

Preparation of Intermediate 13

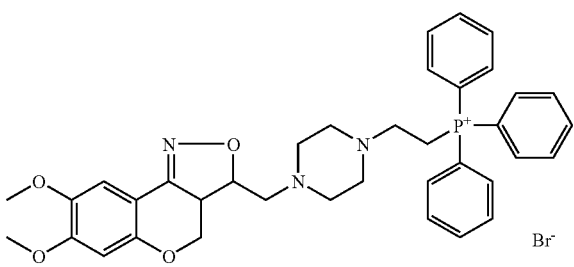

Ethenyltriphenylphosphonium bromide (0.0025 mol) was added to a solution of intermediate 7 (prepared according A1.g) (0.003 mol) in CH₂Cl₂ (20 ml). The reaction mixture was stirred for 4 hours at room temperature. The solvent was evaporated under reduced pressure. Yield: 2.2 g of intermediate 13, used in next reaction step, without further purification.

EXAMPLE A1.n

Preparation of Intermediate 14

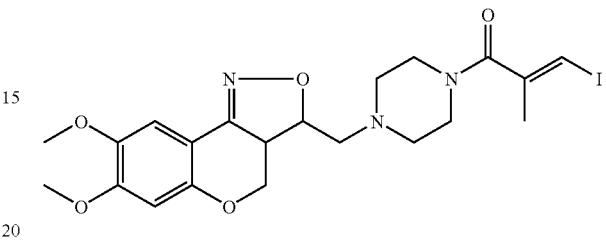

To a solution of (E)-3-iodo-2-methylpropenoic acid (0.009 mol) in CH₂Cl₂, dry (100 ml) at room temperature under N₂ flow, 1,1'-carbonylbis[1H-imidazole] (0.0099 mol) was added. The mixture was stirred for 1 hour, then intermediate 7 (prepared according to A1.g) (0.009 mol) was added. The reaction mixture was stirred at room temperature for 16 hours, washed with H₂O and brine, dried (Na₂SO₄) and the solvent was evaporated under reduced pressure. The residue (white foam) was purified by short open column chromatography over silica gel (eluent: CH₂Cl₂/MeOH 99/1). The pure fractions were collected and the solvent was evaporated. Yield: 3.82 g of intermediate 14 (white solid, 81%).

EXAMPLE A1.o

Preparation of Intermediate 15

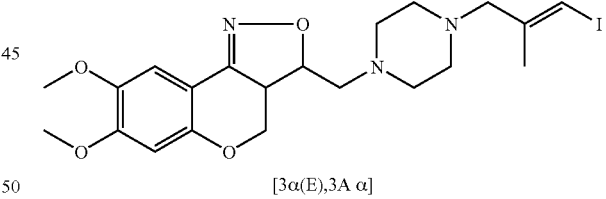

[3α(E),3A α]

A solution of LiAlH₄, 1.0 M/THF (0.00848 mol) in THF (100 ml) was stirred and refluxed under N₂ flow at −20° C. AlCl₃ (0.0093 mol) was added in one portion and the resulting mixture was stirred at −20° C. for 10 minutes. A solution of intermediate 14 (prepared according to A1.n) (0.0077 mol) in THF (100 ml) was added dropwise and the resulting mixture was stirred at −20° C. for 1 hour. A saturated NH₄Cl-solution 20% was added dropwise at −10° C. and the reaction mixture was allowed to warm to room temperature. H₂O was added to the suspension and was extracted with CH₂Cl₂. The separated organic layer was dried (Na₂SO₄) and the solvent was evaporated under reduced pressure. The residue was treated with Et₂O and dried. Yield: 3.73 g of intermediate 15 (white solid, 94%).

EXAMPLE A1.p

Preparation of Intermediate 16

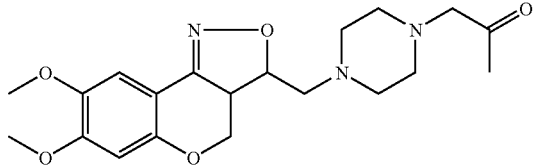

A mixture of intermediate 7 (prepared according A1.g) (0.015 mol), 1-chloro-2-propanone (0.015 mol) and $K_2CO_3$ (0.030 mol) in $CH_3CN$ (60 ml) was stirred for 24 hours at room temperature. The solvent was evaporated. The residue was partitioned between water and $CH_2Cl_2$. The separated organic layer was dried ($Na_2SO_4$), filtered and the solvent evaporated. The residue was purified by short open column chromatography over silica gel (eluent: $CH_2Cl_2/CH_3OH$ 95/5). The pure fractions were collected and the solvent was evaporated. Yield: 4.79 g of intermediate 16 (82%).

EXAMPLE A1.q

Preparation of Intermediate 17

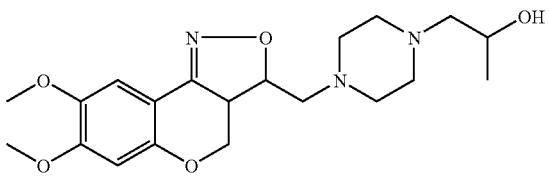

$NaBH_4$ (0.0128 mol) was added portionwise to a solution of intermediate 16 (prepared according A1.p) (0.0051 mol) and $H_2O$ (3.2 ml) in TBF (40.5 ml), at 0° C. The reaction mixture was stirred overnight at room temperature, then treated with a 10% aqueous $NH_4Cl$ solution. This mixture was extracted with $CH_2Cl_2$. The separated organic layer was dried, filtered and the solvent evaporated. The residue was purified by short open column chromatography over silica gel (eluent: $CH_2Cl_2/CH_3OH$ 97/3). The desired fractions were collected and the solvent was evaporated. Yield: 1.6 g of intermediate 17 (80%).

EXAMPLE A1.r

Preparation of Intermediate 18

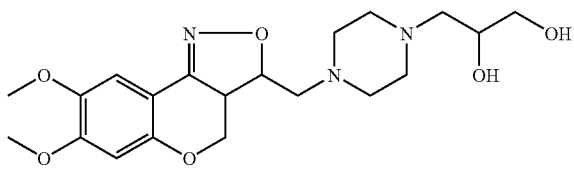

Intermediate 7 (prepared according A1.g) (0.03 mol) was dissolved in $CH_3CN$ (200 ml) and $K_2CO_3$ (0.27 ml) was added. Oxiranemethanol (0.27 mol) was added and the reaction mixture was stirred over the weekend at 60° C. The solvent was evaporated in vacuo. The residue was partitioned between water and $CH_2Cl_2$. The organic layer was separated, dried (Na2SO4), filtered and the solvent was evaporated under reduced pressure. The residue was purified by preparatory HPLC ((1) eluent: $CH_2Cl_2/(CH3OH/NH_3)$ 95/5, then (2) eluent: $CH_2Cl_2/CH_3OH$ 90/10). The product fractions were collected and the solvent was evaporated. Yield: 7.5 g (61%) of pure intermediate 18 and 3.5 g of a mixture of starting material/target compound 1/1.

EXAMPLE A1.s

Preparation of Intermediate 19

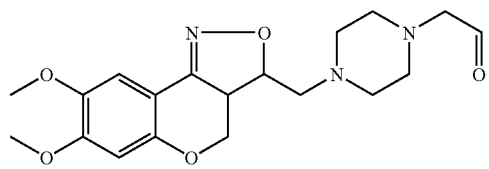

Intermediate 18 (prepared according A1.r) (0.0012 mol) was dissolved in $CH_2Cl_2$ (20 ml). A solution of periodic acid sodium salt (0.0024 mol) in $NaHCO_3/H_2O$ (q.s.) was added and the resulting reaction mixture was stirred vigorously for 2 hours. The mixture was partitioned between water and $CH_2Cl_2$. The separated organic layer was washed with brine, dried ($Na_2SO_4$), filtered and the solvent evaporated in vacuo. Yield: 0.430 g of intermediate 19 (quantitative yield; used in next reaction step, without further purification).

EXAMPLE A2.a

Preparation of Intermediate 20

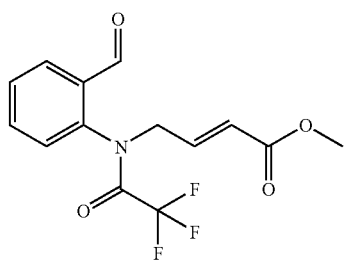

Reaction under N2 atmosphere. A solution of 2,2,2-trifluoro-N-(2-formylphenyl)-acetamide, (0.1869 mol) in DMF (375 ml) was added dropwise to NaH (0.2055 mol) in DMF (375 ml). The mixture was stirred for 30 min. at room temperature. A solution of 4-Bromo-3-butenoic acid methyl ester (0.2803 mol) in DMF (200 ml) was added dropwise. Then, 18-crown-6 (catalytic quantity) was added. The resulting reaction mixture was stirred for 2 hours at 60° C., then overnight at room temperature. The solvent was evaporated. The residue was washed in water and extracted with $CH_2Cl_2$. The separated organic layer was dried ($Na_2SO_4$), filtered and the solvent evaporated. The residue was purified by open column chromatography over silica gel (eluent: $CH_2Cl_2$/hexane 90/10, 100/0 and with $CH_2Cl_2$/2-propanone 96/4, 90/10 and 80/20). The pure fractions were collected and the solvent was evaporated. Yielding: 44.37 g of intermediate 20 (75%, used in next reaction step, without further purification).

EXAMPLE A2.b

Preparation of Intermediate 21

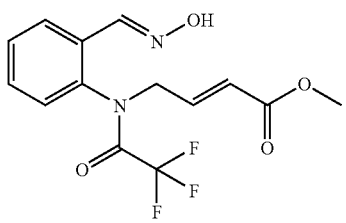

Hydroxylamine (0.169 mol) and pyridine (0.211 mol) were added to a solution of intermediate 20 (prepared according to A2.a) (0.1407 mol) in ethanol (450 ml) and the resulting reaction mixture was stirred for 3 hours at room temperature. The mixture was washed with a 10% citric acid solution, then extracted with $CH_2Cl_2$. The separated organic layer was dried ($Na_2SO_4$), filtered and the solvent was evaporated. Yielding: 45.76 g of intermediate 21 (98%, used in next reaction step, without further purification).

EXAMPLE A2.c

Preparation of Intermediate 22

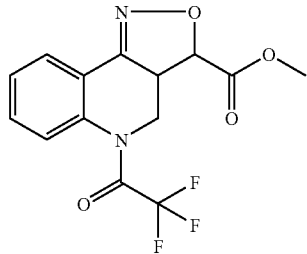

A mixture of intermediate 21 (prepared according to A2.b) (0.0658 mol) and N-chloro-4-methyl-benzenesulfonamide, sodium salt (0.0658 mol) in ethanol (500 ml) was stirred and refluxed for 2 hours. The mixture was concentrated in vacuo, filtered over dicalite, and the filtrate was washed with water and brine, then extracted with $CH_2Cl_2$. The separated organic layer was dried ($Na_2SO_4$), filtered and the solvent evaporated. The residue was purified by open column chromatography over silica gel (eluent: $CH_2Cl_2$/2-propanone 100/0, 96/4, 90/10 and 80/20). The desired fractions were collected and the solvent was evaporated. The residue (syrup) was crystallized from hexane, then washed with DIPE, and dried. Yielding: 12.32 g of intermediate 22 (57%).

EXAMPLE A2.d

Preparation of Intermediate 23

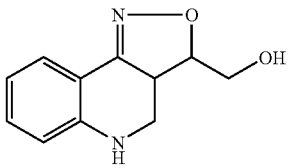

$NaBH_4$ (0.0289 mol) was added portionwise to a mixture of intermediate 22 (prepared according to A2.c) (0.0116 mol) in THF (81 ml) and $H_2O$ (6.8 ml), stirred and cooled on an ice-bath. The resulting reaction mixture was stirred overnight at room temperature. The mixture was treated with a saturated aqueous $NH_4Cl$ solution, then extracted with EtOAc. The separated organic layer was dried ($Na_2SO_4$), filtered and the solvent was evaporated. The residue was washed with $CH_2Cl_2$, then recrystallized from EtOAc. The precipitate was filtered off and dried. Yielding: 0.9 g of intermediate 23 (38%).

EXAMPLE A2.e

Preparation of Intermediate 24

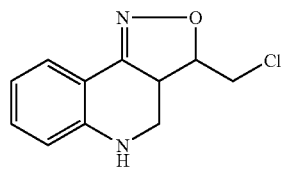

A mixture of intermediate 23 (prepared according A2.d) (0.001468 mol) and triphenylphosphine (0.001909 mol) in tetrachloromethane (30 ml) and THF (20 ml) was stirred and refluxed for 3 hours. The solvent was evaporated till dryness. The residue was purified by short open column chromatography over silica gel (eluent: $CH_2Cl_2$/hexane 90/10, then 100/0). The desired fractions were collected and the solvent was evaporated. The residue was crystallized from methanol. The precipitate was filtered off and dried. Yielding: 2.6 g of intermediate 24 (79%).

EXAMPLE A3.a

Preparation of Intermediate 25

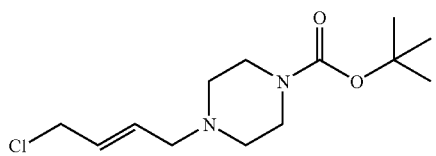

1,1-Dimethylethyl 1-piperazinecarboxylate (0.02 mol) was added portionwise to a solution of 1,4-dichloro-2-butene (0.025 mol) in $CHCl_3$ (60 ml). The reaction mixture was stirred for 24 hours at room temperature, then stirred and refluxed for 24 hours. The reaction was quenched with a saturated aqueous NaHCO₃ solution, dried (Na₂SO₄), filtered and the solvent was evaporated. The residue was purified by short open column chromatography over silica gel (eluent: CH₂Cl₂/EtOAc). The pure fractions were collected and the solvent was evaporated. Yielding: 2.2 g of intermediate 25 (40%).

EXAMPLE A3.b

Preparation of Intermediate 26

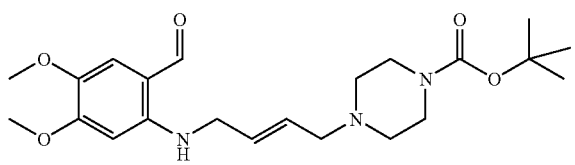

Reaction was carried out under N₂ flow. A mixture of NaH, 60% (0.0579 mol) and 18-crown-6 (cat.quant.) in THF (25 ml) was cooled. A mixture of 2-Amino4,5-dimethoxybenzaldehyde (0.0579 mol) in THF (50 ml) was added portionwise. The reaction was stirred at room temperature for 30 min. A mixture of intermediate 25 (prepared according to A3.a) (0.0386 mol) in THF (50 ml) was added portionwise. The mixture was stirred at room temperature for 3 days and then treated with NH₄Cl (10%). The mixture was extracted with CH₂Cl₂. The organic layer was separated, dried, filtered and the solvent was evaporated till dryness. The residue was purified by short open column chromatography (eluent: CH₂Cl₂/CH₃OH 99/1 and 98/2). The pure fractions were collected and the solvent was evaporated. Yield: 5.5 g of intermediate 26 (23%).

EXAMPLE A3.c

Preparation of Intermediate 27

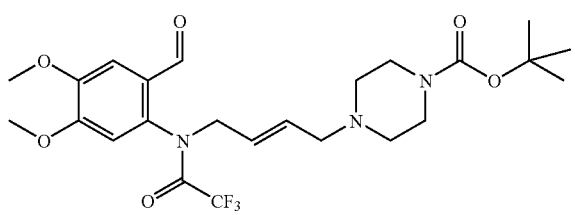

The reaction was carried out under N₂ flow. A mixture of intermediate 26 (prepared according A2.b) (0.02 mol) in THF (80 ml) and 18-crown-6 (cat.quant.) were added portionwise to a mixture of NaH, 60% (0.03 mol) in THF (20 ml). The mixture was stirred at room temperature for 20 min. trifluoroacetic acid anhydride (0.022 mol) was added portionwise. The mixture was stirred at room temperature for 3 hours, treated with a solution of NH₄Cl (20%) and then extracted with CH₂Cl₂ and the solvent was evaporated till dryness. The residue was purified by short column chromatography over silica gel (CH₂Cl₂/CH₃OH 99/1 and 98/2). The pure fractions were collected and the solvent was evaporated. Yield: 5.3 g of intermediate 27 (58%).

EXAMPLE A3.d

Preparation of Intermediate 28

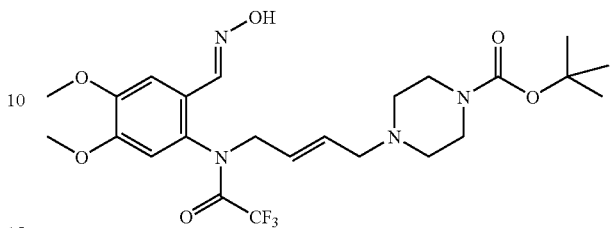

A mixture of intermediate 27 (prepared according to A3.c) (0.0115 mol), hydroxylamine (0.0126 mol) and NaHCO₃ (0.023 mol) in ethanol, abs. (60 ml) was stirred at room temperature for 24 hours, filtered off and the solvent was evaporated till dryness. Yield: 5.8 g of intermediate 28 (95%).

EXAMPLE A3.e

Preparation of Intermediate 29

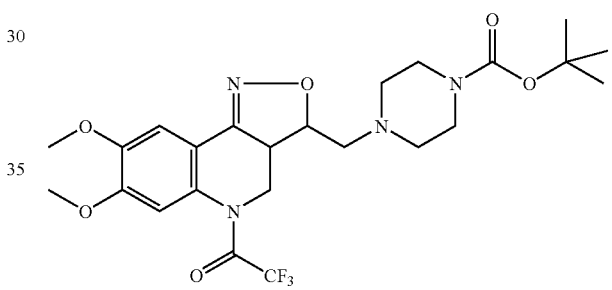

1-chloro-2,5-Pyrrolidinedione (0.0272 mol) was added portionwise to a solution of intermediate 28 (prepared according to A3.d) (0.0109 mol) in CH₂Cl₂ (100 ml). The mixture was stirred at room temperature for 2 hours. Et₃N (0.0272 mol) was added dropwise. The mixture was stirred at room temperature overnight, quenched with a K₂CO₃ 10% solution, then extracted and the solvent was evaporated till dryness. Yield: of intermediate 29.

EXAMPLE A3.f

Preparation of Intermediate 30

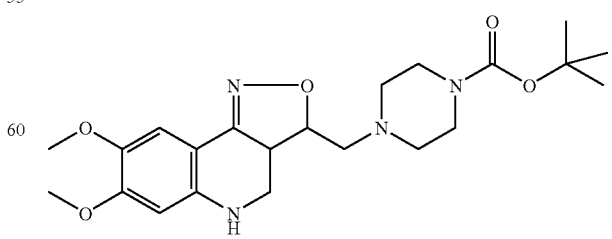

A mixture of intermediate 29 (prepared according to A3.e) (0.0109 mol) and LiOH (0.0119 mol) in H₂O (17.5 ml) and 1,4-dioxane (70 ml) was stirred at room temperature for 3 hours. The mixture was treated with a NaOH (2N) solution and then extracted with CH$_2$Cl$_2$. The solvent was evaporated till dryness. The residue was purified by short open column chromatography (eluent: CH$_2$Cl$_2$/CH$_3$OH 98/2). The pure fractions were collected and the solvent was evaporated. Yield: 2.07 g of intermediate 30 (45%).

EXAMPLE A3.g

Preparation of Intermediate 31

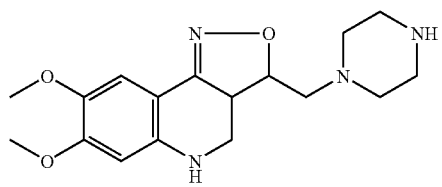

Trifluoroacetic acid (7.9 ml) was added dropwise to a solution of intermediate 30 (0.0047 mol) in CH$_2$Cl$_2$ (33 ml). The mixture was stirred at room temperature for 3 hours, cooled and basified with a 50% NaOH solution. The mixture was extracted and the solvent was evaporated till dryness. Yield: 1.6 g of compound 31 (100%).

EXAMPLE A4.a

Preparation of Intermediate 32

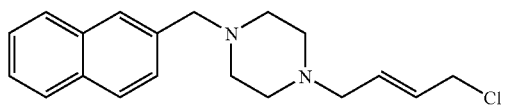

1,4-dichloro-2-butene (0.03 mol) was added to a mixture of 1-(2-naphthylmethyl)piperazine (0.025 mol) and NaHCO$_3$ (0.025 mol) in CH$_2$Cl$_2$ (75 ml). The reaction mixture was stirred for 24 hours at room temperature. The solid was filtered off, washed with more CH$_2$Cl$_2$ and the organic solution was washed with a 10% Na$_2$CO$_3$ solution, dried (Na$_2$SO$_4$), filtered and the solvent was evaporated. The residue was purified by short open column chromatography over silica gel (eluent: CH$_2$Cl$_2$/EtOAc/2-propanone). The pure fractions were collected and the solvent was evaporated. Yield: 3.4 g of intermediate 32 (43%).

EXAMPLE A4.b

Preparation of Intermediate 33

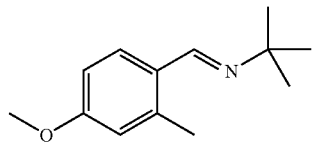

A solution of NS (0.0546 mol) and tert-Butylamine (0.0983 mol) in toluene (75 ml) was stirred and refluxed for 24 hours using a Dean-Stark water separator. The solvent was evaporated. The residue was purified by distillation (bp at 0.5 mm Hg: 75° C.). Yielding: 8.1 g of intermediate 33 (72%).

EXAMPLE A4.c

Preparation of Intermediate 34

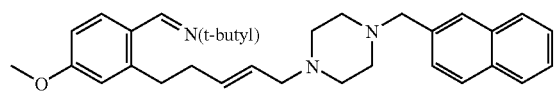

Reaction under N$_2$ atmosphere. n-BuLi (0.014 mol) was added dropwise to a solution of intermediate 33 (prepared according A4.a) (0.0125 mol) and 2,2,6,6-tetramethylpiperidine (0.0012 mol) in THF, dry (25 ml), stirred at −78° C. The mixture was stirred for 3 hours at −10° C. A solution of intermediate 32 (prepared according A4.b) (0.0083 mol) in THF, dry (25 ml) was added portionwise at −10° C. The reaction mixture was stirred for 24 hours at room temperature, then quenched with NH$_4$Cl (10%) and the organic layer was separated. The aqueous layer was extracted with CH$_2$Cl$_2$. The combined organic layers were dried (Na$_2$SO$_4$), filtered and the solvent was evaporated. Yielding: 5.6 g of intermediate 34 (100%)

EXAMPLE A4.d

Preparation of Intermediate 35

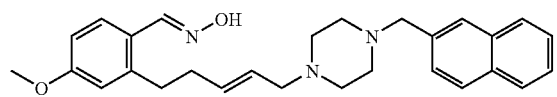

NaHCO$_3$ (0.015 mol) and hydroxylamine (0.0125 mol) were added to a solution of intermediate 34 (prepared according A4.c) (0.0083 mol) in ethanol, abs. (50 ml). The reaction mixture was stirred for 24 hours at room temperature. CH$_2$Cl$_2$ was added and the solid was filtered off and washed with CH$_2$Cl$_2$. The solvent was evaporated. The residue was taken up into CH$_2$Cl$_2$ and washed with 10% Na$_2$CO$_3$ and with brine. The organic layer was separated, dried (Na$_2$SO$_4$), filtered and the solvent was evaporated. The residue was purified by short open column chromatography over silica gel (eluent: CH$_2$Cl$_2$/EtOAc/2-propanone). The desired fractions were collected and the solvent was evaporated. Yielding: 0.9 g of intermediate 35 (24%).

EXAMPLE A5.a

Preparation of Compound 36

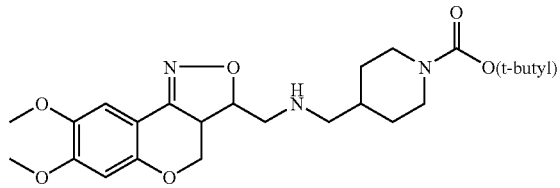

A mixture of A (0.029 mol) and intermediate5 (prepared according to A1.e) (0.0058 mol) in 1,4-dioxane (5 ml) was stirred for 6 hours at 100° C. The solvent was evaporated. The residue was purified by short open column chromatography over silica gel (eluent: $CH_2Cl_2/CH_3OH$ 98/2–97/3). The product fractions were collected and the solvent was evaporated. Yield: 3.3 g of intermediate 36

EXAMPLE A5.b

Preparation of Compound 37

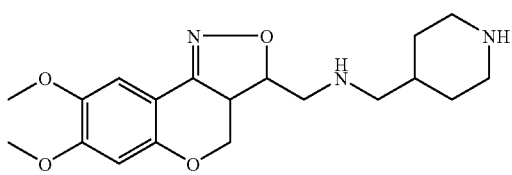

Trifluoroacetic acid (11.7 ml) was added dropwise to a solution of intermediate 36 (prepared according to A5.f) (0.0071 mol) in $CHCl_3$ (50 ml) and the resulting reaction mixture was stirred for 3 hours at ±10° C. The reaction mixture was cooled, then further alkalized with 50% NaOH. This mixture was extracted and the extract's solvent was evaporated. Yield: 2.5 g of intermediate 37 (quantitative yield; used in next reaction step, without further purification).

B. Preparation of the Final Compounds

EXAMPLE B1.a

Preparation of Compound 1

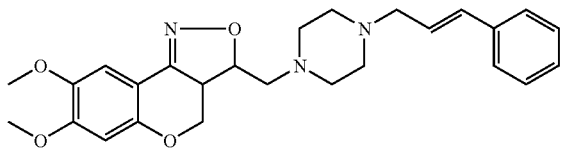

A mixture of intermediate5 (prepared according to A1.e) (0.0291 mol) and 1-(3-phenyl-2-propenyl)-piperazine, (0.0582 mol) was heated for 2 hours at 100° C. The crude reaction mixture was washed with water and extracted with $CH_2Cl_2$. The separated organic layer was dried ($Na_2SO_4$), filtered and the solvent was evaporated. The residue was purified by short open column chromatography over silica gel (eluent: $CH_2Cl_2/CH_3OH$ 95/5) and by HPLC over silica gel (eluent: $CH_2Cl_2/CH_3OH$ 80/20). The pure fractions were collected and the solvent was evaporated. This fraction was separated into its optical enantiomers by chiral column chromatography over Chiralpak AD (eluent: $C_2H_5OH/CH_3CN$ 90/10). The (B)-enantiomeric fractions were collected and the solvent was evaporated. The residue was dissolved in methanol and converted into the hydrochloric acid salt (1:2). The precipitate was filtered off and dried. Yielding: 2.47 g of compound 1.

EXAMPLE B1.b

Preparation of Compound 2

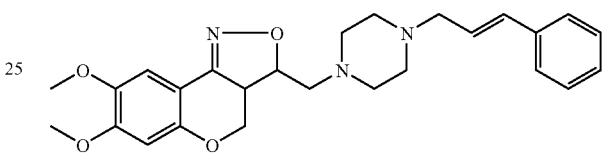

A mixture of intermediate 5 (prepared according to A1.e) (0.0044 mol) and (3-phenyl-2-propenyl)-piperazine (0.0087 mol) was stirred for 2 hours at 100° C. The reaction mixture was purified by short open column chromatography over silica gel (eluent: $CH_2Cl_2/CH_3OH$ 95/5), then by high-performance liquid chromatography over silica gel (eluent: $CH_2Cl_2/CH_3OH$ 96/4). The pure fractions were collected and the solvent was evaporated. The residue (1.4 g) was treated with diethyl ether, then dried. Yielding: 1.2 g of compound 2 (60%).

EXAMPLE B 1.c

Preparation of Compound 3

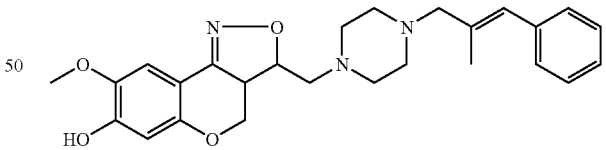

A mixture of intermediate 6 (0.00227 mol), (E) 1-(2-methyl-3-phenyl-2-propenyl)piperazine (0.00273 mol) and $NaHCO_3$ (0.00455 mol) in dioxane (30 ml) was stirred and refluxed for 48 hours. The solvent was evaporated. The residue was dissolved in $CH_2Cl_2$. The organic solution was washed with water, dried ($MgSO_4$), filtered and the solvent was evaporated. The residue was purified by short open column chromatography over silica gel (eluent: $CH_2Cl_2/(CH_3OH/NH_3)$ 99/1), then by HPLC (eluent: $CH_2Cl_2/CH_3OH$ 99.5/0.5 to 98/2). The desired fractions were collected and the solvent was evaporated. Yield: 0.17 g of compound 3.

EXAMPLE B1.d

Preparation of Compound 4

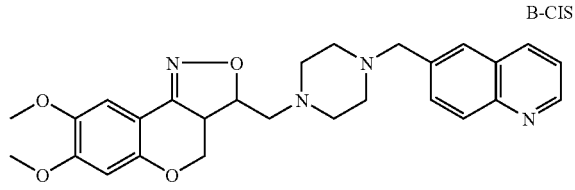

B-CIS

A mixture of intermediate 8 (prepared according to A1.h) (0.0058 mol) and

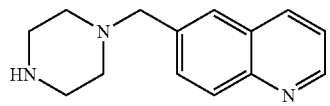

(0.0116 mol) in dioxane (10 ml) was stirred and refluxed for 8 hours, then stirred overnight at room temperature, then stirred and refluxed for 18 hours. The mixture was treated with H$_2$O and extracted with CH$_2$Cl$_2$. The solvent of the separated organic layer was evaporated. The residue was purified by short open column chromatography (eluent: CH$_2$Cl$_2$/MeOH 97/3). The desired fractions were collected and the solvent was evaporated. The residue was treated with diethyl ether, then dried. Yield: 0.9 g of compound 4 (33%).

EXAMPLE B1.e

Preparation of Compound 5

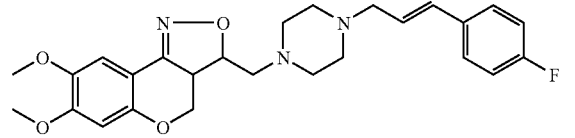

A mixture of intermediate 10 (prepared according to A1.i) (0.0029 mol),

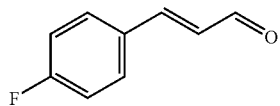

(0.0058 mol), AcOH (0.48 g) and (AcO)$_3$BHNa (0.4 g) in 1,2-dichloroethane (20 ml) was stirred and refluxed overnight. The mixture was treated with H$_2$O and extracted. The solvent of the separated organic layer was evaporated. The residue was purified by short column chromatography over silica gel (eluent: CH$_2$Cl$_2$/MeOH 97/3). The desired fractions were collected and the solvent was evaporated. The residue was treated with diethyl ether, then dried. Yield: 1.07 g of compound 5 (82%).

EXAMPLE B1.f

Preparation of Compound 6

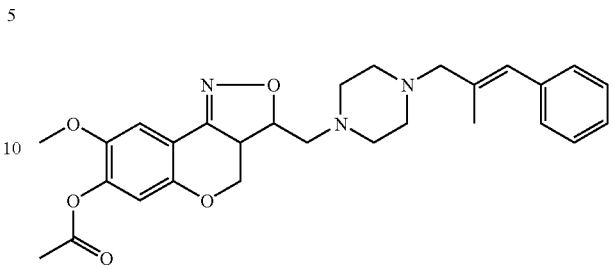

A mixture of compound 3 (prepared according ex. B1) (0.00020 mol), acetylchloride (0.00024 mol) and Et$_3$N (0.00061 mol) in chloroform (10 ml) was stirred at room temperature for 2 hours. Water was added and this mixture was extracted with CH$_2$Cl$_2$. The separated organic layer was dried (MgSO$_4$), filtered and the solvent evaporated in vacuo. The residue was purified by CC-TLC on Chromatotron (eluent: CH$_2$Cl$_2$/CH$_3$OH 97/3; then 99/1). The desired fractions were collected and the solvent was evaporated. Yield: 0.022 g of compound 6.

EXAMPLE B1.g

Preparation of Compound 7

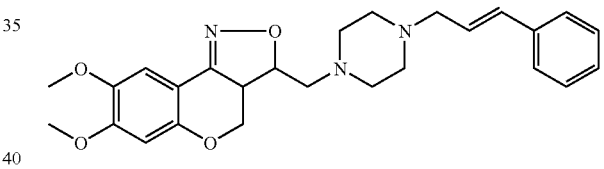

Preparation of Compound 8

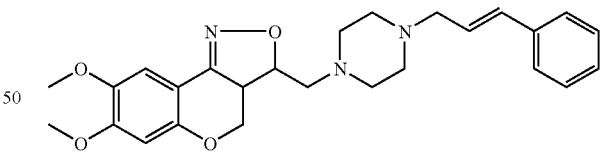

Compound 2 (prepared according B1.b) (0.0022 mol) was separated and purified into its optical enantiomers by chiral column chromatography over Chiralpak AD (eluent: C$_2$H$_5$OH/CH$_3$CN 90/10). Two fraction groups were collected and their solvent was evaporated. Yielding: ±1.5 g of fraction 1 (LCI purity: >99.5%) and ±1.5 g of fraction 2 (LCI purity: >99.5%). Fraction 1 was crystallized by treatment with hexane, stirring overnight. The precipitate was filtered off and dried. Yielding: 1.08 g of compound compound 7 (grease solid). Fraction 2 was crystallized by treatment with EtOAc, stirring overnight. The precipitate was filtered off and dried. Yielding: 0.54 g of 8 (grease solid).

EXAMPLE B2.a

Preparation of Compound 9

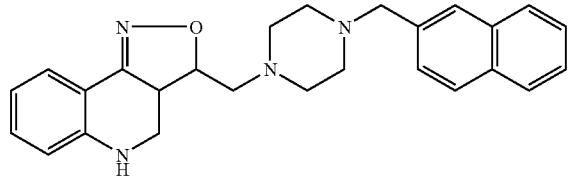

A mixture of intermediate 24 (prepared according A2.e) (0.0022 mol), 1-(2-naphthalenylmethyl)-piperazine, (0.0044 mol) and KI (catalytic quantity) in 1,4-dioxane (2.5 ml) was stirred and refluxed overnight. The reaction mixture was washed with water and this mixture was extracted with $CH_2Cl_2$. The residue was purified by short open column chromatography over silica gel (eluent: $CH_2Cl_2/CH_3OH$ 98/2), then by HPLC (eluent: $CH_2Cl_2/(CH_3OH/NH_3)$ 96/4). The pure fractions were collected and the solvent was evaporated. The residue was treated with DIPE, filtered off and dried. Yield: 0.3 g of compound 9 (30%).

EXAMPLE B2.b

Preparation of Compound 10

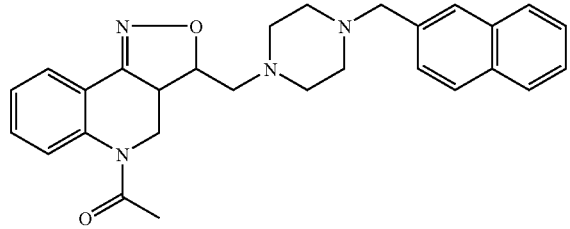

Reaction under $N_2$ atmosphere. A solution of compound 9 (prepared according to B2.a) (0.0012 mol) in THF, dry (3 ml) and 18-crown-6 (catalytic quantity) was slowly added to a solution of NaH, 60% (0.0018 mol) in THF, dry (2 ml). The reaction mixture was stirred for 30 min at room temperature acetylchloride (0.0013 mol) was added dropwise and the reaction mixture was stirred for 3 hours at room temperature. The reaction mixture was treated with aqueous $NH_4Cl$ and extracted with $CH_2Cl_2$. The separated organic layer was dried, filtered and the solvent evaporated. The residue was purified by short open column chromatography over silica gel (eluent: $CH_2Cl_2/CH_3OH$ 98/2), then by HPLC (eluent: $CH_2Cl_2/(CH_3OH/NH_3)$ 98/2). The pure fractions were collected and the solvent was evaporated. Yield: 0.26 g of compound 10 (52%).

EXAMPLE B3a

Preparation of Compound 11

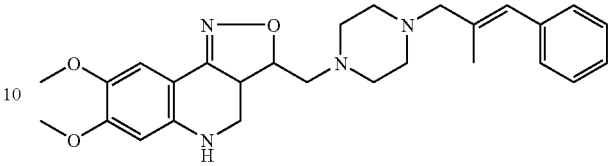

A mixture of intermediate 31 (prepared according A3.g) (0.0045 mol), (E)-(3-chloro-2-methyl-1-propenyl)-benzene (0.0037 mol) and $K_2CO_3$ (0.0037 mol) in DMF (15 ml) was stirred at 70° C. for 2 hours. The mixture was washed with water and then extracted with $CH_2Cl_2$. The organic layer was separated, dried, filtered and the solvent was evaporated. The residue was purified by short column chromatography over silica gel (eluent: $CH_2Cl_2/CH_3OH$ 98/2). The desired fractions were collected and the solvent was evaporated. The residue was purified again by HPLC (eluent: $CH_2Cl_2/(CH_3OH/NH_3)$ 98/2). The pure fractions were collected and the solvent was evaporated. The residue was treated with DIPE. The precipitate was filtered off and dried. Yield: 0.34 g of compound 11 (20%).

EXAMPLE B3.b

Preparation of Compound 12

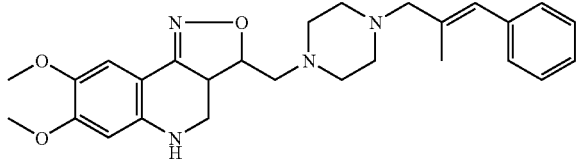

Preparation of Compound 13

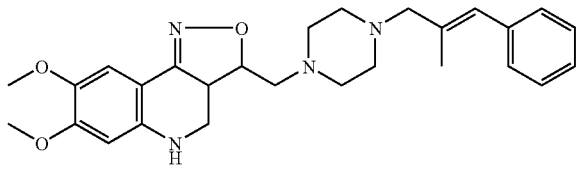

Compound 11 (prepared according to B3.a) (0.00605 mol) was purified by high-performance liquid chromatography over Chiralcel OJ (eluent: hexane/MeOH/EtOH 20/24/56). The desired fractions were collected and the solvent was evaporated. Yield: fractions A and B. Fraction A was purified by high-performance liquid chromatography over RP BDS C18 (eluent: (0.5% $NH_4OAc$ in $H_2O/CH_3CN$ (90/10))/MeOH 70/30). The pure fractions were collected and the organic solvent was evaporated. The aqueous layer was extracted with $CH_2Cl_2$. The separated organic layer was dried ($MgSO_4$), filtered and the solvent was evaporated. The residue was stirred in hexane and the precipitate was filtered off. Yield: 0.69 g of compound 12. Fraction B was purified by high-performance liquid chromatography over RP BDS C18 (eluent: (0.5% NH₄OAc in H₂O/CH₃CN(90/10))/MeOH 70/30). The pure fractions were collected and the organic solvent was evaporated. The aqueous layer was extracted with CH₂Cl₂. The separated organic layer was dried (MgSO₄), filtered and the solvent was evaporated. The residue was stirred in hexane and the precipitate was filtered off. Yield: 0.67 g of compound 13.

EXAMPLE 4

Preparation of Compound 14

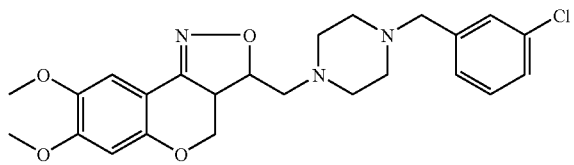

Reaction done in solid phase using a Quest 210 synthesizer (Argonaut Technologies, San Carlos, USA). N,N-Diisopropylethylamine (0.0036 mol) was added to a suspension of

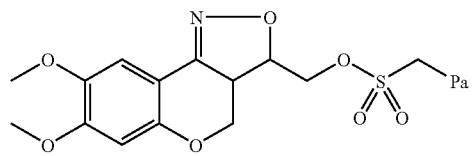

(0.0006 mol) in acetonitrile (4 ml). 1-(2-Chlorophenylmethyl)piperazine (0.0012 mol) was added and the resulting reaction mixture was stirred for 20 hours at 80° C. Then, each reaction vessel was filtrated and the filtrate was evaporated. The residue was HPLC purified. The pure fractions were collected and the solvent was evaporated. Yield: 0.102 g of compound 14

EXAMPLE B5.a

Preparation of Compound 15

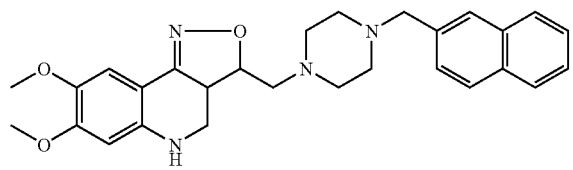

A mixture of intermediate 7 (prepared according A1.g) (0.0036 mol), 2-(bromomethyl)naphthalene (0.0055 mol) and K₂CO₃ (0.0055 mol) in MIK (15 ml) was stirred for ±24 hours at 100° C. The crude reaction mixture was washed with water, then extracted with CH₂Cl₂. The separated organic layer was dried (Na₂SO₄), filtered and the solvent was evaporated. The residue was purified by high-performance liquid chromatography over silica gel (2×) ((I) eluent: CH₂Cl₂/CH₃OH 95/5; (II) eluent: CH₂Cl₂/(CH₃OH/NH₃) 98/2). The pure fractions were collected and the solvent was evaporated. Yielding: 0.2 g of compound 15 (11%).

EXAMPLE B5.b

Preparation of Compound 16

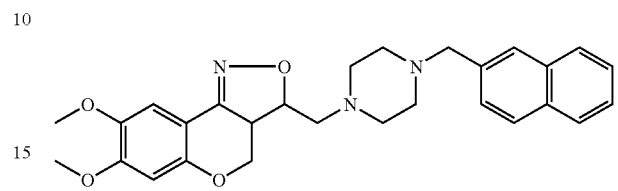

Preparation of Compound 17

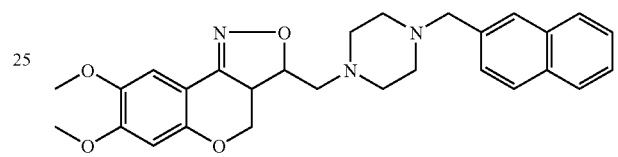

Compound 15 (prepared according B5.a) (0.0106 mol) was separated into its enantiomers by column chromatography (eluent: hexane/C₂H₅OH gradient 30/70 to 0/100; column: CHIRALPAK AD 1000 Å 20 μm DIACEL). Two pure fractions were collected and their solvents were evaporated. The residue was dissolved in CH₃OH and converted into the hydrochloric acid salt (1:2). The precipitate was filtered off and dried. Yielding: 2.08 g of compound 16 (36%) and 2.19 g of compound 17 (38%).

EXAMPLE B6

Preparation of Compound 18

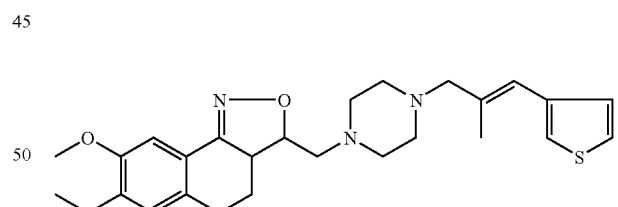

A mixture of intermediate 7 (prepared according to A1.g) (0.0045 mol), 2-methyl-3-(3-thienyl)-2-propenal (0.00675 mol), NaBH(OAc)₃ (0.00675 mol) and HOAc (2 drops) in 1,2-dichloroethaan (30 ml) was stirred overnight at room temperature. A saturated aqueous NH₄Cl solution was added and this mixture was extracted with CH₂Cl₂. The separated organic layer was dried (MgSO₄), filtered and the solvent evaporated in vacuo. The residue was purified by flash column chromatography over silica gel (eluent: CH₂Cl₂/(CH₃OH/NH₃) 97/3), then by HPLC (eluent: CH₂Cl₂/(CH₃OH/N₃) 99/1 to 98/2). The product fractions were collected and the solvent was evaporated. Yield: 0.965 g of compound 18 (46%; containing also 3% of the (Z) isomer!).

EXAMPLE B7

Preparation of Compound 19

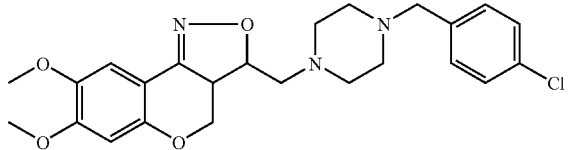

A mixture of intermediate 10 (prepared according to A1.j) (0.003 mol), 4-chlorobenzaldehyde (0.0045 mol) and (AcO)₃BHNa (0.0045 mol) in 1,2-dichloroethane (30 ml) was stirred and refluxed for 2 hours at room temperature. A saturated aqueous NH₄Cl-solution was added and the mixture was extracted with CH₂Cl₂. The separated organic layer was dried (MgSO₄), filtered and the solvent was evaporated in vacuum. The residue was purified by short open column chromatography over silica gel (eluent: CH₂Cl₂/(MeOH/NH₃) 97/3). The desired fractions were collected and the solvent was evaporated. The residue was precipitated from DIPE. Yield: 1.180 g of compound 19 (57%).

EXAMPLE B8

Preparation of Compound 20

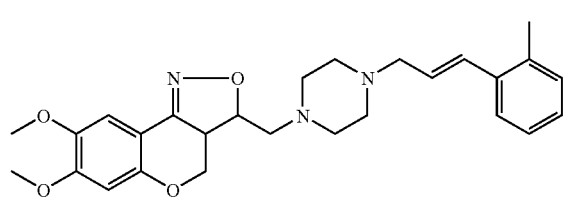

A mixture of

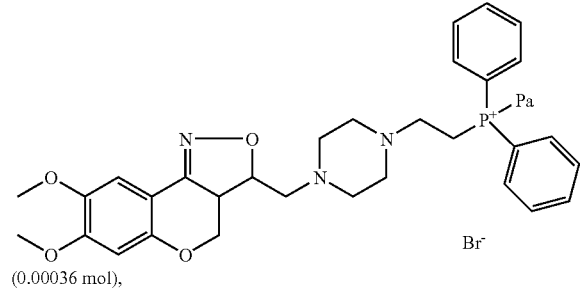

(0.00036 mol), 2-methylbenzaldehyde (0.00108 mol) and NaOCH₃, 30% in CH₃OH (0.00108 mol) in CH₃OH, dry (8 ml) was stirred for 16 hours at 65° C. (Reaction done in solid phase using a Quest 210 synthesizer (Argonaut Technologies, San Carlos, USA)). The mixtures were filtered and the filtrate was HPLC purified (eluent: CH₂Cl₂/(CH₃OH/NH₃) 98/2). The desired fractions were collected and the solvent was evaporated. Yield: 0.032 g of compound 20.

EXAMPLE B9

Preparation of Compound 21

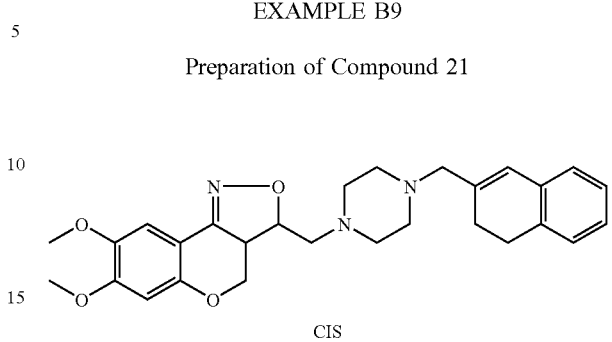

CIS

Reaction under N₂ atmosphere. Solution LiAlH₄, 1 M/THF (0.8 ml) was stirred at −20° C. AlCl₃ (0.0009 mol) was added in one portion. The resulting solution was stirred for 10 min at −20° C. A solution of intermediate 12 (prepared according to A1.l) (0.0008 mol) in THF, dry (5 ml) was added dropwise and the resulting reaction mixture was stirred for one hour at −20° C. Then, a saturated aqueous NH₄Cl solution was added carefully. The reaction mixture was washed with water, then extracted with CH₂Cl₂. The separated organic layer was dried (Na₂SO₄), filtered and the solvent was evaporated. The residue was treated with ether. The residue (0.13 g) was purified by CC-TLC Chromatotron (eluent: CH₂Cl₂/CH₃OH 97/3). The pure fractions were collected and the solvent was evaporated. Yield: 0.09 g of compound 21 (30%).

EXAMPLE B10

Preparation of Compound 22

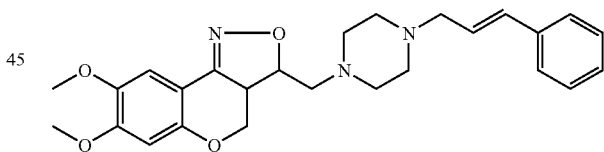

Reaction under N₂ flow. A mixture of intermediate 13 (prepared according to A1.m) (0.001 mol) in CH₃OH, dry (20 ml) was stirred at room temperature. NaOCH₃, 30% in CH₃OH (0.002 mol) was added. 5-Indanecarboxaldehyde (0.002 mol) was added and the resulting reaction mixture was stirred and refluxed for 16 hours. The reaction mixture was allowed to cool to room temperature. 20% NH₄Cl was added and this mixture was extracted with CH₂Cl₂. The separated organic layer was washed with water, with brine, dried (Na₂SO₄), filtered, and the solvent was evaporated under reduced pressure. The residue was purified by short open column chromatography and CC-TLC (eluent: CH₂Cl₂/CH₃OH 98/2). The product fractions were collected and the solvent was evaporated. Yield: 0.035 g of compound 22 (7.2%, light-brown solid).

EXAMPLE B11

Preparation of Compound 23

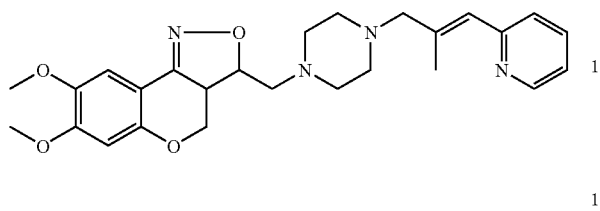

A mixture of intermediate 15 (prepared according to A1.o) (0.00136 mol), 2-(trimethylstannyl)pyridine (0.0027 mol) and Pd(PPh$_3$)$_4$ (0.00013 mol) in toluene (20 ml) was heated to 100° C. The reaction mixture was stirred for 16 hours and was allowed to cool to room temperature. H$_2$O was added and the mixture was extracted with CH$_2$Cl$_2$. The separated organic layer was collected, washed with H$_2$O and brine, dried (Na$_2$SO$_4$) and the solvent was evaporated under reduced pressure. The residue was purified by short open column chromatography over silica gel (eluent: CH$_2$Cl$_2$/MeOH 98/2). The pure fraction was collected and the solvent was evaporated. The resulting residue was purified by CC-TLC on Chromatotron (eluent: CH$_2$CL$_2$/MeOH 98/2). The pure fraction was collected and the solvent was evaporated. Yield: 0.044 g of compound 23 (light brown solid, 7%).

EXAMPLE B12

Preparation of Compound 24

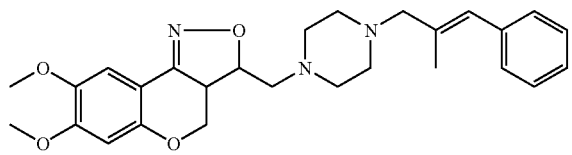

Reaction under N2 atmosphere. n-BuLi, 2.5M/hexanes (0.0062 mol) was added dropwise to a stirred solution of (p-Flurorobenzyl)triphenylphosphonium chloride (0.0062 mol) in THF (20 ml). The mixture was stirred for 15 min. A solution of intermediate 11 (prepared according A1.k) (0.00514 mol) in THF (20 ml) was added dropwise. The reaction mixture was stirred for 16 hours at 50° C. Water was added and this mixture was extracted with Et$_2$O. The separated organic layer was dried (MgSO$_4$), filtered and the solvent evaporated in vacuo. The residue was purified by short open column chromatography over silica gel (eluent: CH$_2$Cl$_2$/CH$_3$OH 97/3), then by HPLC (eluent: CH$_2$Cl$_2$/(CH$_3$OH/NH$_3$) 99/1) to separate the (E)/(Z) isomers. Two product fraction groups were collected and their solvent was evaporated. Yield: 0.651 g of compound 24 (26%, (E)).

EXAMPLE B13

Preparation of Compound 25

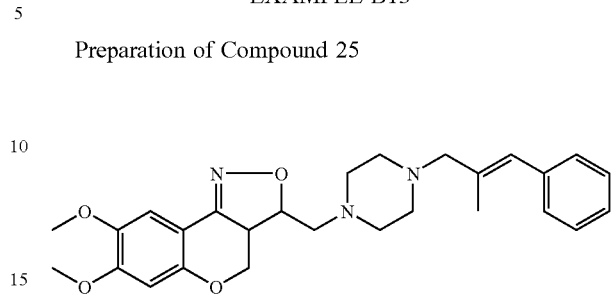

Resin

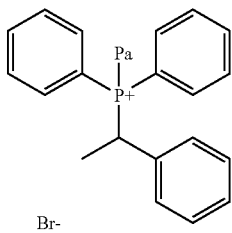

(0.0016 mol; 1.5 mmole/g) was suspended in THF. 1.6 M BuLi (0.0015 mol) was added and the mixture was stirred for 15 min. The mixture was filtered and the filter residue (resin) was washed with anhydrous THF (3×). The resin was suspended in THF (5 ml). Intermediate 19 (prepared according to A1.s) (0.0004 mol) was added and the reaction mixture was stirred overnight at 100° C. The mixture was cooled, filtered and the filtrate was evaporated in vacuo. The residue was purified by preparatory HPLC (eluent: CH$_2$Cl$_2$/(CH$_3$OH/NH3) 97/3). The product fractions were collected and the solvent was evaporated. Yield: 0.168 g of compound 25.

EXAMPLE B14

Preparation of Compound 26

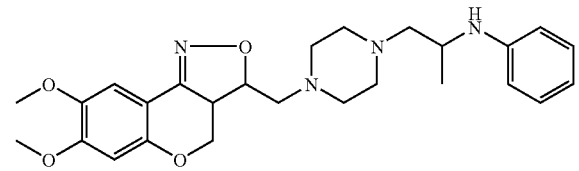

A mixture of intermediate 16 (prepared according to A1.p) (0.0025 mol), benzenamine (0.0028 mol) and NaBH$_4$ (0.0028 mol) in HOAc (50 ml) was stirred for 2 hours at room temperature. An aqueous NH₄OH solution was added. This mixture was extracted with CH₂Cl₂. The separated organic layer was dried (MgSO₄), filtered and the solvent evaporated in vacuo. The residue was purified by short open column chromatography over silica gel (eluent: CH₂Cl₂/(CH₃OH/NH₃) 99/1), then by flash column chromatography over silica gel (eluent: CH₂Cl₂/(CH₃OH/NH₃) 98/2). The product fractions were collected and the solvent was evaporated. Yield: 0.181 g of compound 26 (15%).

EXAMPLE B15

Preparation of Compound 27

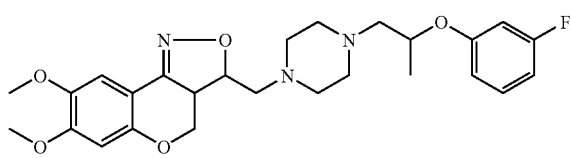

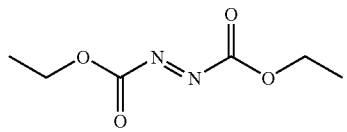

(0.0018 mol) was added dropwise to a solution of intermediate 17 (prepared according to A1.q) (0.0012 mol), 3-fluorophenol (0.0018 mol) and PPh₃, pol. (0.0024 mol) in THF, dry (10 ml), under N₂ atmosphere. The reaction mixture was stirred overnight at room temperature. The mixture was filtered, washed with CH₂Cl₂ and CH₃OH, and the solvent was evaporated. The residue was purified by short open column chromatography over silica gel (eluent: CH₂Cl₂/EtOAc 2/1 and CH₂Cl₂/CH₃OH 96/4), then by flash column chromatography over silica gel (eluent: CH₂Cl₂/CH₃OH 97/3). The product fractions were collected and the solvent was evaporated. Yield: 0.29 g of compound 27 (50%).

EXAMPLE B16

Preparation of Compound 28

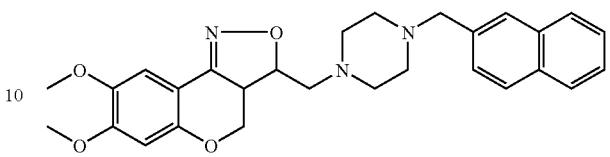

NaClO (4%) (0.005 mol) was added to a solution of intermediate 35 (prepared according A4.d) (0.002 mol) in CH₂Cl₂ (10 ml). The reaction mixture was stirred for 4 hours at room temperature. Et₃N (0.004 mol) was added and the reaction mixture was stirred for 24 hours at room temperature. The organic layer was separated, washed with Na₂SO₃ (10%), dried (Na₂SO₄), filtered and the solvent was evaporated. The residue was purified by short open column chromatography over silica gel (eluent: EtOAc and CH₂Cl₂/CH₃OH 95/5). The desired fractions were collected and the solvent was evaporated. The residue was taken up into diethyl ether, then filtered through dicalite and the filtrate was evaporated. The residue was dissolved in diethyl ether and converted into the hydrochloric acid salt (1:2). The precipitate was filtered off, washed with 2-propanone and diethyl ether, and dried. Yield: 0.15 g of compound 28 (15%).

EXAMPLE B17

Preparation of Compound 29

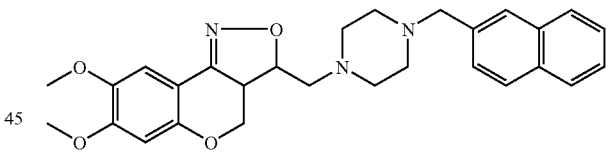

A mixture of intermediate 37 (prepared according to A5.g) (0.006 mol) and 2-(bromomethyl)naphthalene (0.003 mol) in dioxane (40 ml) was stirred at 100° C. for 6 hours, then overnight at room temperature. The reaction mixture was treated with a 10% aqueous K₂CO₃ solution, then extracted with CH₂Cl₂. The separated organic layer was evaporated. The residue was purified by short open column chromatography over silica gel (eluent: CH₂Cl₂/CH₃OH 95/5 and 90/10 and CH₂Cl₂/(CH₃OH/NH₃) 95/5). The product fractions were collected and the solvent was evaporated. The residue (1.49 g) was treated with diethyl ether, then dried. Yield: 0.8 g of compound 29 (53%).

In the following tables (Tables 1–5) a number of compounds are given which have been prepared according to any one of the Examples above. All compounds have also been tested for their pharmacological activity.

TABLE 1
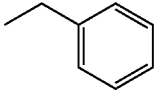
| Comp. nr. | Ex. nr. | R8 a | b | c | d | R3 | Phys.data and stereochemistry |
|---|---|---|---|---|---|---|---|
| 31 | B1a/B1b | H | H | H | H | 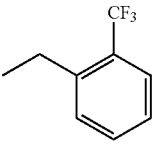 | cis |
| 79 | B4 | H | H | H | H | 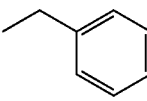 | |
| 85 | B4 | H | H | H | H | 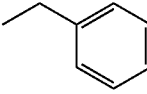 | |
| 89 | B4 | H | H | H | H | 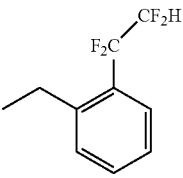 | |
| 80 | B4 | H | H | H | H | 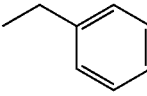 | |
| 14 | B4 | H | H | H | H | 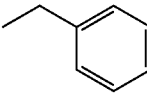 | |
| 86 | B7 | H | H | H | H | 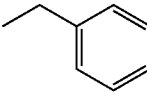 | cis |
| 19 | B7 | H | H | H | H | 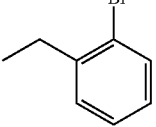 | (B-cis) |
| 84 | B4 | H | H | H | H | 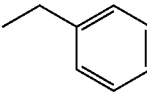 | |
| 90 | B4 | H | H | H | H | | |

TABLE 1-continued
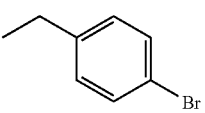
| Comp. nr. | Ex. nr. | R8 a | b | c | d | R3 | Phys.data and stereochemistry |
|---|---|---|---|---|---|---|---|
| 91 | B4 | H | H | H | H | 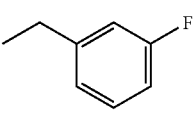 | |
| 285 | B4 | H | H | H | H | 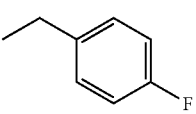 | B-cis |
| 286 | B4 | H | H | H | H | 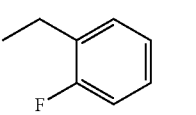 | B-cis HCl(1:2) Hydrate (1:1) |
| 287 | B4 | H | H | H | H | 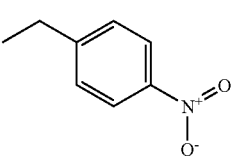 | B-cis |
| 81 | B4 | H | H | H | H | 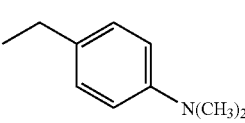 | |
| 83 | B4 | H | H | H | H | 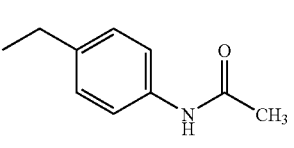 | |
| 94 | B4 | H | H | H | H | 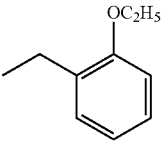 | |
| 87 | B4 | H | H | H | H | 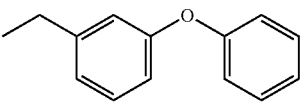 | |
| 88 | B4 | H | H | H | H | 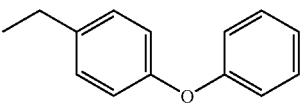 | |
| 82 | B4 | H | H | H | H | | |

TABLE 1-continued
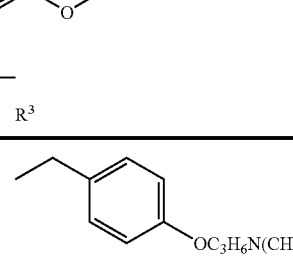
| Comp. nr. | Ex. nr. | R⁸ a | b | c | d | R³ | Phys.data and stereochemistry |
|---|---|---|---|---|---|---|---|
| 99 | B4 | H | H | H | H | 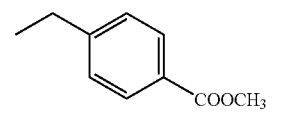 4-OC₃H₆N(CH₃)₂ benzyl | |
| 93 | B4 | H | H | H | H | 4-COOCH₃ benzyl | |
| 97 | B4 | H | H | H | H | 3-CN benzyl | |
| 98 | B4 | H | H | H | H | 4-CN benzyl | |
| 57 | B1a/B1b | H | H | H | H | 3-phenylbenzyl | cis |
| 95 | B4 | H | H | H | H | 2-OCH₃,4-OCH₃ benzyl | |
| 96 | B4 | H | H | H | H | 3-OCH₃,4-OCH₃ benzyl | |
| 288 | B4 | H | H | H | H | 2,4-diCl benzyl | cis |
| 289 | B4 | H | H | H | H | 3,4-diCl benzyl | cis |

TABLE 1-continued
| Comp. nr. | Ex. nr. | R8 a | b | c | d | R3 | Phys.data and stereochemistry |
|---|---|---|---|---|---|---|---|
| 290 | B4 | H | H | H | H | 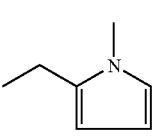 | cis |
| 291 | B5b | H | H | H | H | 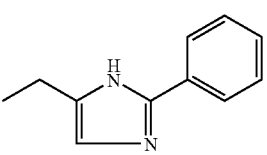 | cis |
| 128 | B5b | H | H | H | H | 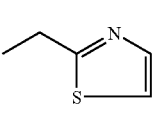 | cis |
| 292 | B5b | H | H | H | H | 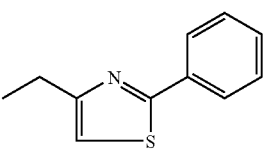 | cis |
| 149 | B5b | H | H | H | H | 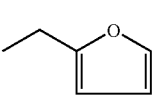 | cis |
| 293 | B5b | H | H | H | H | 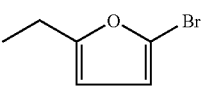 | cis |
| 294 | B5b | H | H | H | H | 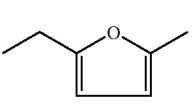 | cis |
| 295 | B5b | H | H | H | H | 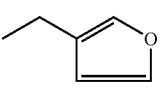 | cis |
| 296 | B5b | H | H | H | H | 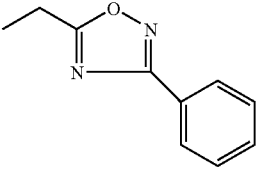 | cis |
| 141 | B5b | H | H | H | H |  | cis |

TABLE 1-continued

| Comp. nr. | Ex. nr. | R⁸ a | b | c | d | R³ | Phys.data and stereochemistry |
|---|---|---|---|---|---|---|---|
| 138 | B5b | H | H | H | H | ethyl-(2-phenyl-1,3,4-oxadiazol-5-yl) | cis |
| 297 | B5b | H | H | H | H | ethyl-(thiophen-2-yl) | cis |
| 298 | B5b | H | H | H | H | ethyl-(5-bromothiophen-2-yl) | cis |
| 299 | B5b | H | H | H | H | ethyl-(4-bromothiophen-2-yl) | cis |
| 300 | B5b | H | H | H | H | ethyl-(thiophen-3-yl) | cis |
| 15 | B5b | H | H | H | H | ethyl-(naphthalen-2-yl) | cis |
| 34 | B5b | H | H | H | H | ethyl-(naphthalen-2-yl) | [3α(R),3a α];.HCl(1:2).H₂O(1:2) |
| 36 | B1a/B1b | H | H | H | H | ethyl-(naphthalen-2-yl) | cis;.HCl(1:2) |
| 16 | B5b | H | H | H | H | ethyl-(naphthalen-2-yl) | [A-[3α,3a α]];.HCl(1:2) |
| 17 | B5b | H | H | H | H | ethyl-(naphthalen-2-yl) | [B-[3α,3a α]];.HCl(1:2) |
| 131 | B5b | H | CH₃ | H | CH₃ | ethyl-(naphthalen-2-yl) | [3α(R*,S*),3a α] |
| 132 | B5b | CH₃ | H | H | CH₃ | ethyl-(naphthalen-2-yl) | [3α(R*,S*),3a α]; H₂O(1:1) |

TABLE 1-continued

| Comp. nr. | Ex. nr. | R8 a | b | c | d | R3 | Phys.data and stereochemistry |
|---|---|---|---|---|---|---|---|
| 133 | B5b | H | CH3 | H | H | 2-ethylnaphthalene | [3α,3a α] |
| 92 | B4 | H | H | H | H | 1-ethylnaphthalene | |
| 52 | B1a/B1b | H | H | H | H | 8-ethylnaphthalene | cis;.HCl(1:2) |
| 75 | B5a | H | H | H | H | 2-ethyl-1-methoxynaphthalene | cis |
| 62 | B5b | H | H | H | H | 6-ethyl-2-methoxynaphthalene | cis |
| 71 | B5b | H | H | H | H | 3-ethyl-2-methoxy isoquinoline derivative | cis |
| 117 | B5b | H | H | H | H | 6-ethyl-2-methylnaphthalene | cis |
| 72 | B5b | H | H | H | H | 6-ethyl-2-methylnaphthalene | cis |
| 74 | B1a/B1b | H | H | H | H | 2-ethyl-3-methylnaphthalene | cis |

TABLE 1-continued
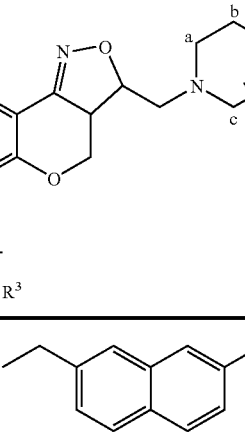
| Comp. nr. | Ex. nr. | R⁸ a | b | c | d | R³ | Phys.data and stereochemistry |
|---|---|---|---|---|---|---|---|
| 135 | B5b | H | H | H | H | 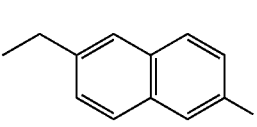 | cis |
| 76 | B5b | H | H | H | H | 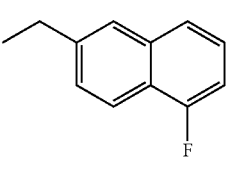 | cis |
| 136 | B5b | H | H | H | H | 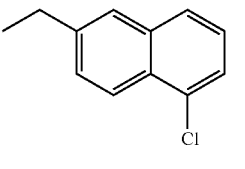 | cis |
| 301 | B5b | H | H | H | H | 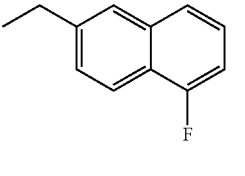 | cis |
| 302 | B5b | H | H | H | H | 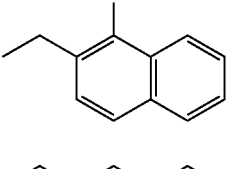 | A-cis |
| 77 | B5a | H | H | H | H | 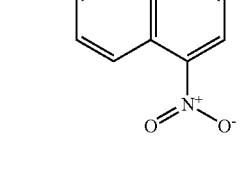 | cis |
| 303 | B5b | H | H | H | H | 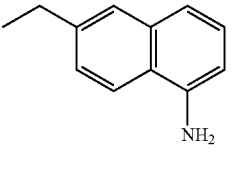 | B-cis |
| 304 | B5b | H | H | H | H |  | B-cis |

TABLE 1-continued
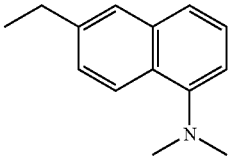
| Comp. nr. | Ex. nr. | R[8] a | b | c | d | R[3] | Phys.data and stereochemistry |
|---|---|---|---|---|---|---|---|
| 305 | B5b | H | H | H | H | 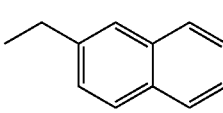 | B-cis |
| 140 | B5b | H | H | H | H | 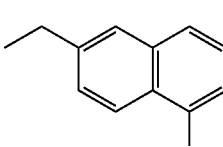 | cis |
| 193 | B5b | H | H | H | H | 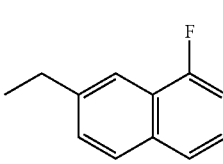 | cis |
| 206 | B5b | H | H | H | H | 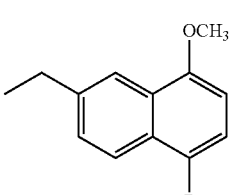 | cis |
| 123 | B5b | H | H | H | H | 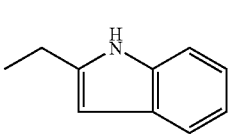 | cis |
| 51 | B1a/B1b | H | H | H | H | 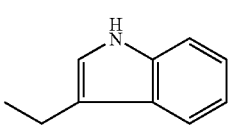 | cis |
| 306 | B5b | H | H | H | H | 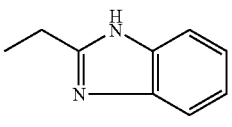 | cis |
| 37 | B5b | H | H | H | H | 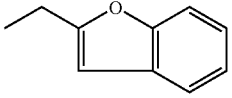 | cis;.HCl(1:2).H$_2$O(1:3) |
| 54 | B5b | H | H | H | H |  | cis;.HCl(1:2) |

TABLE 1-continued
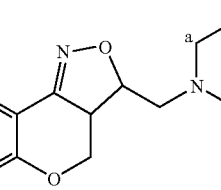
| Comp. nr. | Ex. nr. | R⁸ a | b | c | d | R³ | Phys.data and stereochemistry |
|---|---|---|---|---|---|---|---|
| 49 | B1a/B1b | H | H | H | H | 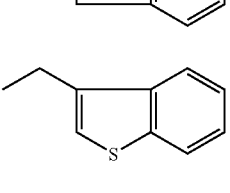 | cis;.HCl(1:2) |
| 204 | B5b | H | H | H | H | 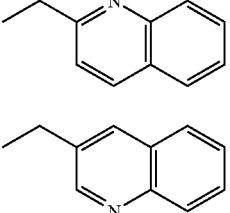 | cis |
| 45 | B1a/B1b | H | H | H | H | 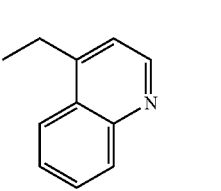 | |
| 61 | B1a/B1b | H | H | H | H | 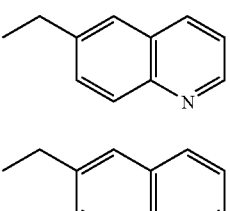 | cis |
| 59 | B1a/B1b | H | H | H | H | 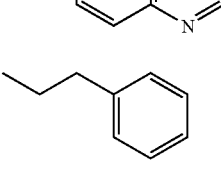 | cis;.HCl(1:2) .H₂O(1:2) |
| 58 | B1a/B1b | H | H | H | H | 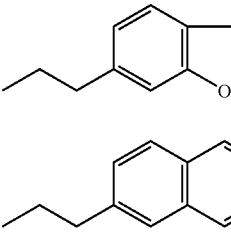 | cis |
| 4 | B1d/B1e | H | H | H | H |  | (B-cis) |
| 33 | B5b | H | H | H | H |  | cis |
| 47 | B1a/B1b | H | H | H | H |  | cis,.HCl(1:2) |
| 50 | B5b | H | H | H | H |  | cis;.HCl(1:2) |

TABLE 1-continued
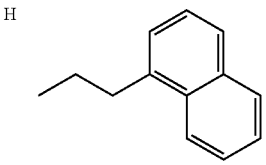
| Comp. nr. | Ex. nr. | a | b | c | d | R³ | Phys.data and stereochemistry |
|---|---|---|---|---|---|---|---|
| 53 | B5b | H | H | H | H | 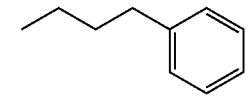 | cis;.HCl(1:2) |
| 32 | B1a/B1b | H | H | H | H | 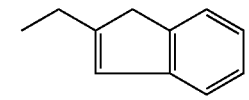 | cis |
| 191 | B5b | H | H | H | H | 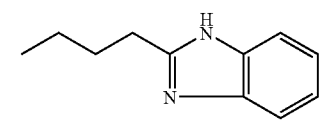 | cis |
| 56 | B1a/B1b | H | H | H | H | 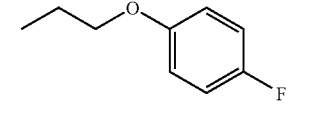 | cis |
| 48 | B1a/B1b | H | H | H | H | 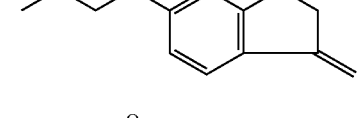 | cis;.HCl(1:2) |
| 67 | B5b | H | H | H | H | 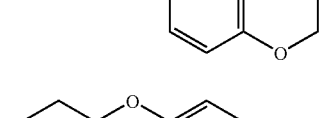 | cis |
| 73 | B5b | H | H | H | H | 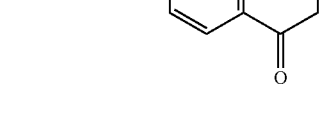 | cis |
| 78 | B5b | H | H | H | H | 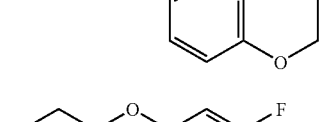 | cis |
| 68 | B5b | H | H | H | H | 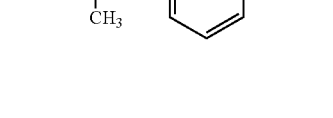 | cis |
| 27 | B15 | H | H | H | H |  | |

TABLE 1-continued
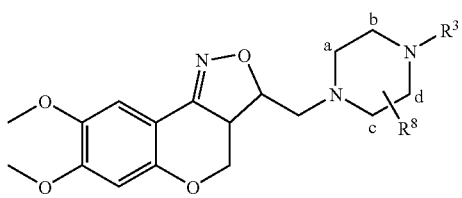
| Comp. nr. | Ex. nr. | R⁸ a | b | c | d | R³ | Phys.data and stereochemistry |
|---|---|---|---|---|---|---|---|
| 147 | B15 | H | H | H | H | 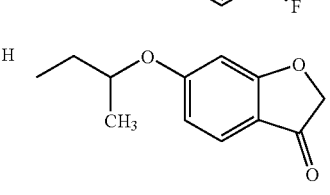 | cis |
| 142 | B | H | H | H | H | 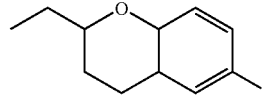 | cis |
| 35 | B5b | H | H | H | H | 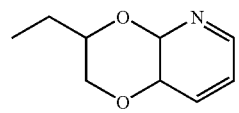 | [3α(S),3a α] |
| 307 | B5b | H | H | H | H | 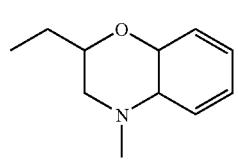 | cis |
| 308 | B5b | H | H | H | H | 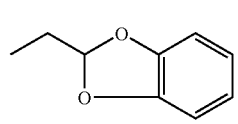 | cis |
| 66 | B5a | H | H | H | H | 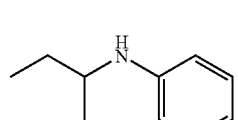 | cis |
| 26 | B14 | H | H | H | H | 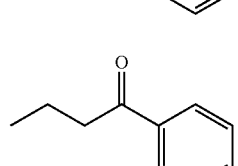 | [3α,3a α] |
| 309 | B14 | H | H | H | H | 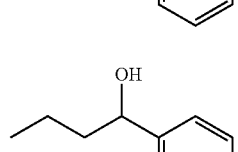 | B-cis |
| 310 | B14 | H | H | H | H |  | B-cis |

TABLE 1-continued
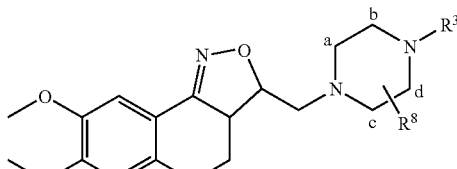
| Comp. nr. | Ex. nr. | R8 a | b | c | d | R3 | Phys.data and stereochemistry |
|---|---|---|---|---|---|---|---|
| 311 | B14 | H | H | H | H | 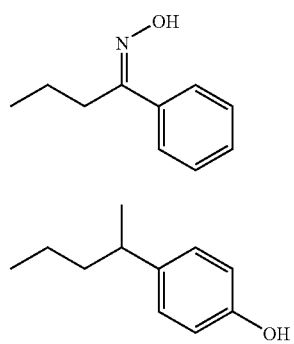 | B-cis |
| 312 | B1a/B1b | H | H | H | H | 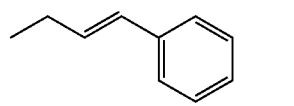 | [B-[3α(E),3a α]] |
| 2 | B1a/B1b | H | H | H | H | 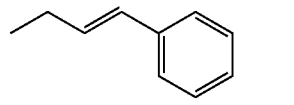 | [3α(E),3a α] |
| 7 | B1g | H | H | H | H | 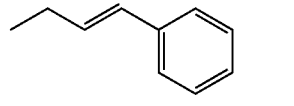 | [A-[3α(E),3a α]] |
| 8 | B1g | H | H | H | H | 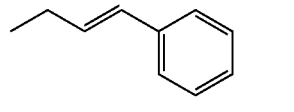 | [B-[3α(E),3a α]] |
| 1 | B1a/B1b | H | H | H | H | 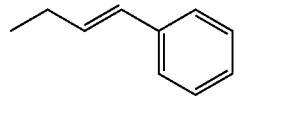 | [B-[3α(E),3a α]];. HCl(1:2).H2O(1:1) |
| 30 | B1a/B1b | H | H | H | H | 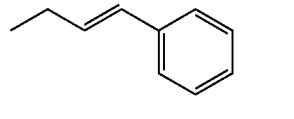 | [3α(E),3a β] |
| 46 | B1a/B1b | H | H | H | H | 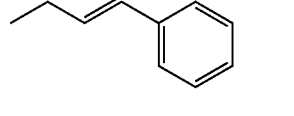 | [A-[3α(E),3a α]];. HCl(1:2) |
| 116 | B8 | H | H | H | H | 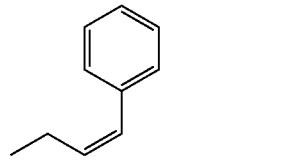 | cis |
| 64 | B10 | H | H | H | H |  | [3α(Z),3a α] |

TABLE 1-continued
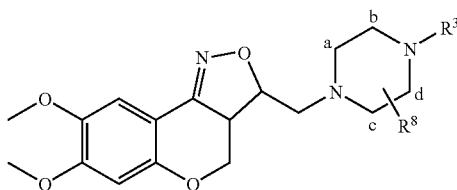
| Comp. nr. | Ex. nr. | R8 a | b | c | d | R3 | Phys.data and stereochemistry |
|---|---|---|---|---|---|---|---|
| 41 | B1a/B1b | H | H | H | H | 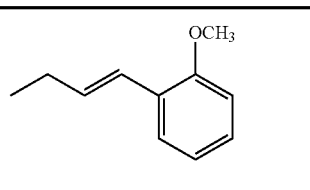 | [3α(E),3a α];. HCl(1:2) |
| 38 | B1a/B1b | H | H | H | H | 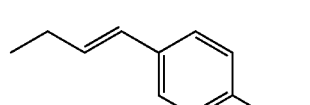 | [3α(E),3a α];. HCl(1:2) |
| 39 | B1a/B1b | H | H | H | H | 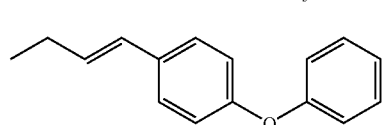 | [3α(E),3a α];. HCl(1:2) |
| 102 | B8 | H | H | H | H | 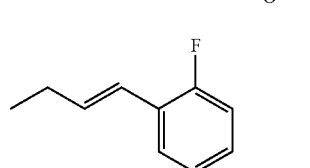 | cis |
| 44 | B1a/B1b | H | H | H | H | 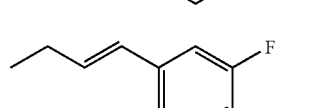 | [3α(E),3a α] |
| 42 | B1a/B1b | H | H | H | H | 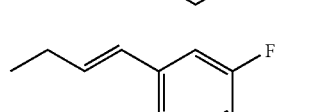 | [3α(E),3a α] |
| 189 | B13B | H | H | H | H | 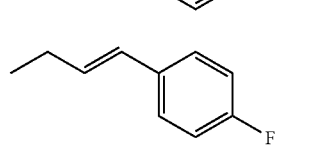 | cis |
| 43 | B1a/B1b | H | H | H | H | 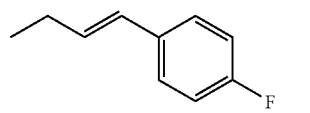 | [3α(E),3a α];. HCl (1:2) |
| 313 | B1a/B1b | H | H | H | H | 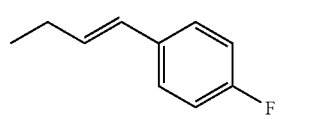 | [A-[3α(E),3a α]] |
| 5 | B1d/B1e | H | H | H | H | 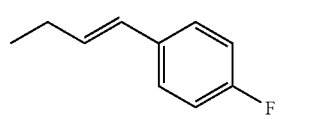 | [B-[3α(E),3a α]] |

TABLE 1-continued

| Comp. nr. | Ex. nr. | R⁸ a | b | c | d | R³ | Phys.data and stereochemistry |
|---|---|---|---|---|---|---|---|
| 100 | B8 | H | H | H | H | CH₂CH=CH-(2-Cl-C₆H₄) | cis |
| 108 | B8 | H | H | H | H | CH₂CH=CH-(3-Cl-C₆H₄) | cis |
| 113 | B8 | H | H | H | H | CH₂CH=CH-(4-Cl-C₆H₄) | cis |
| 105 | B8 | H | H | H | H | CH₂CH=CH-(2-Br-C₆H₄) | cis |
| 106 | B8 | H | H | H | H | CH₂CH=CH-(3-Br-C₆H₄) | cis |
| 107 | B8 | H | H | H | H | CH₂CH=CH-(4-Br-C₆H₄) | cis |
| 111 | B8 | H | H | H | H | CH₂CH=CH-(2-CF₃-C₆H₄) | cis |
| 101 | B8 | H | H | H | H | CH₂CH=CH-(3-CF₃-C₆H₄) | cis |
| 103 | B8 | H | H | H | H | CH₂CH=CH-(4-CF₃-C₆H₄) | cis |

TABLE 1-continued

| Comp. nr. | Ex. nr. | a | b | c | d | R³ | Phys.data and stereochemistry |
|---|---|---|---|---|---|---|---|
| 112 | B8 | H | H | H | H | 2-(1,1,1-trifluoro-2,2-difluoroethyl... CH₂CH=CHCH₃-phenyl (CF₂H, CF₃ at ortho) | cis |
| 104 | B8 | H | H | H | H | 4-(COOCH₃)-phenyl-CH=CHCH₂CH₃ | cis |
| 182 | B13 | H | H | H | H | 3-(COOCH₃)-phenyl-CH=CHCH₂CH₃ | cis |
| 109 | B8 | H | H | H | H | 3-NO₂-phenyl-CH=CHCH₂CH₃ | cis |
| 180 | B13 | H | H | H | H | 2-NO₂-phenyl-CH=CHCH₂CH₃ | cis |
| 20 | B8 | H | H | H | H | 2-CH₃-phenyl-CH=CHCH₂CH₃ | cis |
| 110 | B8 | H | H | H | H | 3-CH₃-phenyl-CH=CHCH₂CH₃ | cis |
| 114 | B8 | H | H | H | H | 3-phenoxy-phenyl-CH=CHCH₂CH₃ | cis |

TABLE 1-continued
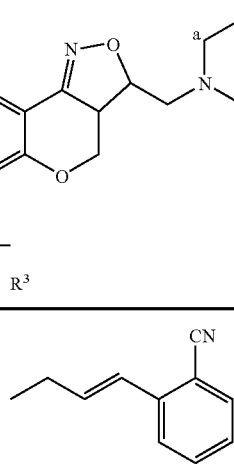
| Comp. nr. | Ex. nr. | R[8] a | b | c | d | R[3] | Phys.data and stereochemistry |
|---|---|---|---|---|---|---|---|
| 175 | B13 | H | H | H | H | 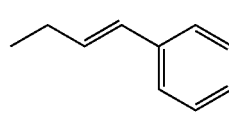 | cis |
| 176 | B13 | H | H | H | H | 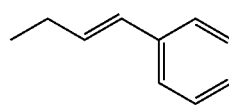 | cis |
| 115 | B8 | H | H | H | H | 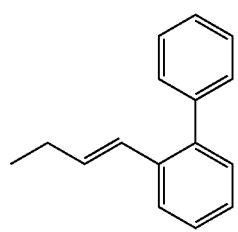 | cis |
| 177 | B13 | H | H | H | H | 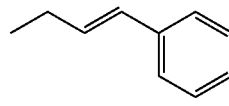 | cis |
| 184 | B13 | H | H | H | H | 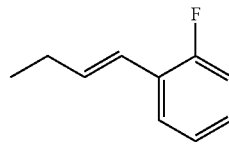 | (B) |
| 172 | B13 | H | H | H | H | 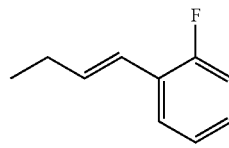 | (A) |
| 185 | B13 | H | H | H | H | 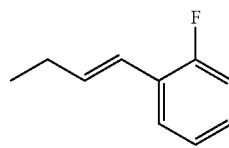 | (B) |
| 173 | B13 | H | H | H | H |  | (A) |

TABLE 1-continued

| Comp. nr. | Ex. nr. | R8 a | b | c | d | R3 | Phys.data and stereochemistry |
|---|---|---|---|---|---|---|---|
| 186 | B13 | H | H | H | H | (2,3-difluorophenyl)propenyl | (B) |
| 167 | B13 | H | H | H | H | (2,6-difluorophenyl)propenyl | cis |
| 170 | B13 | H | H | H | H | (2,5-difluorophenyl)propenyl | cis |
| 171 | B13 | H | H | H | H | (3,5-difluorophenyl)propenyl | cis |
| 168 | B13 | H | H | H | H | (2,6-dichlorophenyl)propenyl | cis |
| 174 | B13 | H | H | H | H | (2-chloro-4-fluorophenyl)propenyl | (A) |
| 187 | B13 | H | H | H | H | (2-chloro-4-fluorophenyl)propenyl | (B) |
| 169 | B13 | H | H | H | H | (2-fluoro-6-chlorophenyl)propenyl | cis |

TABLE 1-continued

| Comp. nr. | Ex. nr. | R⁸ a | b | c | d | R³ | Phys.data and stereochemistry |
|---|---|---|---|---|---|---|---|
| 22 | B10 | H | H | H | H | propenyl-indane | [3α(E),3a α] |
| 118 | B7 | H | H | H | H | propenyl-benzodioxine | cis |
| 119 | B7 | H | H | H | H | propenyl-fluorene | cis |
| 120 | B6 | H | H | H | H | propenyl-dibenzofuran | cis |
| 124 | B6 | H | H | H | H | propenyl-benzodioxole | [3α(E),3a α] |
| 125 | B6 | H | H | H | H | propenyl-dihydrobenzofuran | [3α(E),3a α] |
| 179 | B13 | H | H | H | H | propenyl-(nitro,dimethoxy)phenyl | cis |
| 159 | B8 | H | H | H | H | propenyl-thiophene | cis |
| 314 | B8 | H | H | H | H | propenyl-thiophene | [A-[3α(E),3a α]] |
| 315 | B8 | H | H | H | H | propenyl-thiophene | [B-[3α(E),3a α]] |

TABLE 1-continued
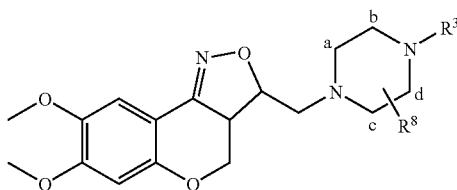
| Comp. nr. | Ex. nr. | R⁸ a | b | c | d | R³ | Phys.data and stereochemistry |
|---|---|---|---|---|---|---|---|
| 160 | B8 | H | H | H | H | 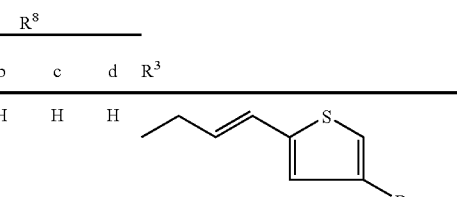 | cis |
| 161 | B8 | H | H | H | H | 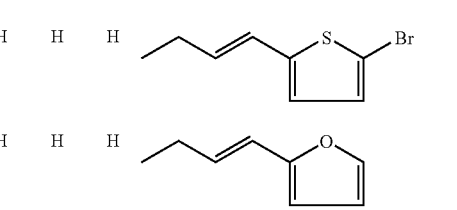 | cis |
| 158 | B8 | H | H | H | H | 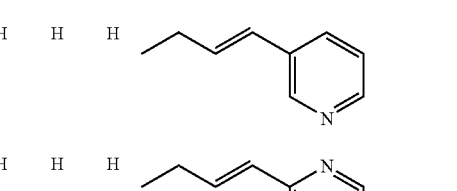 | cis |
| 163 | B8 | H | H | H | H | 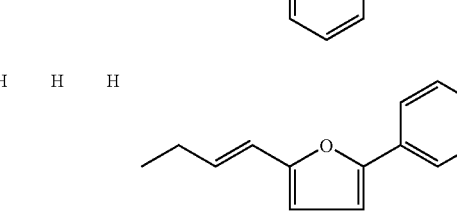 | cis |
| 164 | B8 | H | H | H | H | 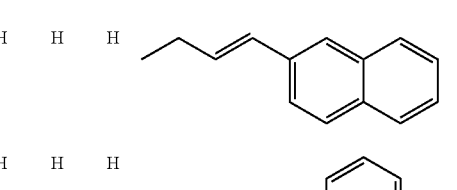 | cis |
| 165 | B8 | H | H | H | H | 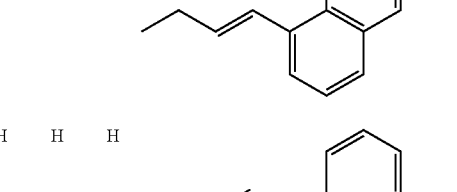 | cis |
| 181 | B13 | H | H | H | H | 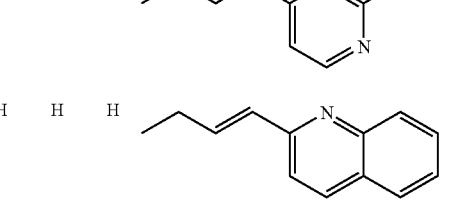 | cis |
| 55 | B5a | H | H | H | H | 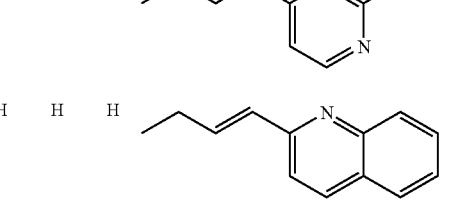 | [3α(E),3a α];. HCl(1:2) |
| 162 | B8 | H | H | H | H |  | cis |
| 166 | B8 | H | H | H | H |  | cis |

TABLE 1-continued

| Comp. nr. | Ex. nr. | R⁸ a | b | c | d | R³ | Phys.data and stereochemistry |
|---|---|---|---|---|---|---|---|
| 178 | B13 | H | H | H | H | (anthracen-9-yl-CH=CH-CH2-CH3) | (A) |
| 188 | B13 | H | H | H | H | (anthracen-9-yl-CH=CH-CH2-CH3) | (B) |
| 316 | B13 | H | H | H | H | (Ph-CH=CH-CH(CH3)2) | [B-[3α(E),3a α]] |
| 60 | B5a | H | H | H | H | (Ph-C(CH3)=CH-CH2CH3) | [3α(E),3a α] |
| 70 | B5b | H | H | H | H | (Ph-C(CH3)=CH-CH2CH3) | [B-[3α(E),3a α]];. HCl(1:2).H2O(1:1) |
| 69 | B5b | H | H | H | H | (Ph-CH=C(CH3)-CH2CH3) | [3α(E),3a α] |
| 126 | B5b | H | H | H | H | (Ph-CH=C(CH3)-CH2CH3) | [A-[3α(E),3a α]] |
| 129 | B5b | H | H | H | H | (Ph-CH=C(CH3)-CH2CH3) | [A-[3α(E),3a α]];. (E)-2-Butenedioate (1:2) |
| 134 | B5a | CH3 | H | H | CH3 | (Ph-CH=C(CH3)-CH2CH3) | [3α(R*,S*)(E),3a α] |

TABLE 1-continued
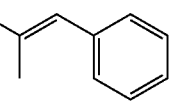
| Comp. nr. | Ex. nr. | R8 a | b | c | d | R3 | Phys.data and stereochemistry |
|---|---|---|---|---|---|---|---|
| 137 | B5a | H | CH3 | H | CH3 | 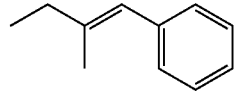 | [3α(R*,S*)(E),3a α] |
| 139 | B1a/B1b | CH3 | H | CH3 | H | 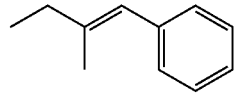 | [3α(R*,S*)(E),3a α] |
| 148 | B1f | H | H | H | H | 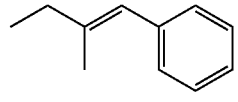 | [3α(Z),3a α] |
| 190 | B13 | H | H | H | H | 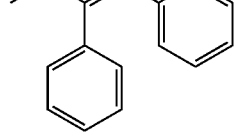 | |
| 151 | B13 | H | H | H | H | 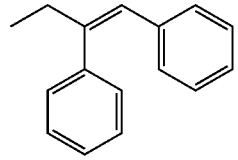 | (A) |
| 183 | B13 | H | H | H | H | 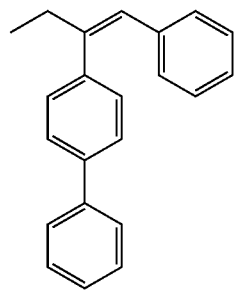 | (B) |
| 152 | B13 | H | H | H | H | 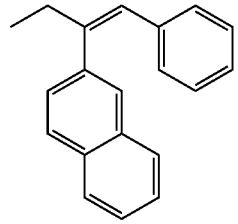 | cis |
| 153 | B13 | H | H | H | H |  | cis |

TABLE 1-continued
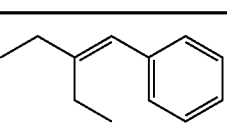
| Comp. nr. | Ex. nr. | R8 a | b | c | d | R3 | Phys.data and stereochemistry |
|---|---|---|---|---|---|---|---|
| 154 | B13 | H | H | H | H | 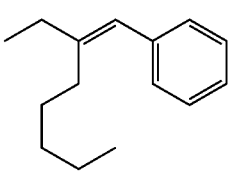 | cis |
| 192 | B5a | H | H | H | H | 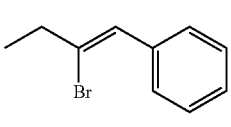 | [3α(E),3a α] |
| 143 | B5a | H | H | H | H | 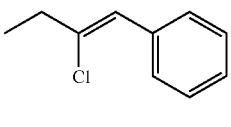 | [3α(Z),3a α] |
| 144 | B5a | H | H | H | H | 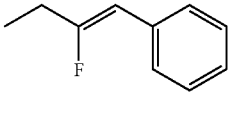 | [3α(Z),3a α] |
| 146 | B5a | H | H | H | H | 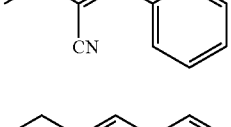 | [3α(Z),3a α] |
| 150 | B5a | H | H | H | H | 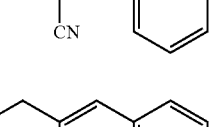 | [3α(Z),3a α] |
| 317 | B5a | H | H | H | H | 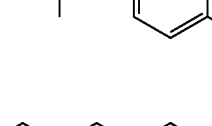 | [B-[3α(Z),3a α]] |
| 155 | B13 | H | H | H | H | 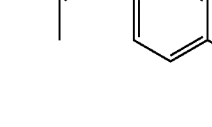 | cis |
| 156 | B13 | H | H | H | H |  | cis |

TABLE 1-continued
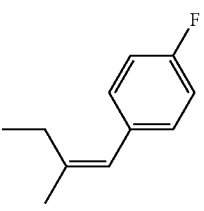
| Comp. nr. | Ex. nr. | R8 a | b | c | d | R3 | Phys.data and stereochemistry |
|---|---|---|---|---|---|---|---|
| 200 | B12 | H | H | H | H | 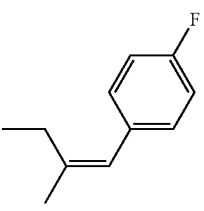 | [3α(Z),3a α] |
| 207 | B12 | H | H | H | H | 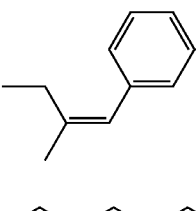 | [B-[3α(Z),3a α]] |
| 194 | B12 | H | H | H | H |  | [3α(Z),3a α] |
| 195 | B12 | H | H | H | H | 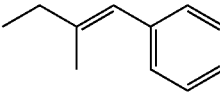 | [3α(E),3a α] |
| 196 | B12 | H | H | H | H | 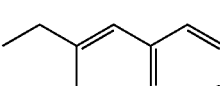 | [3α(E),3a α] |
| 318 | B12 | H | H | H | H | 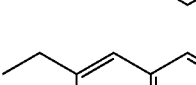 | [A-[3α(E),3a α]] |
| 24 | B5a | H | H | H | H | 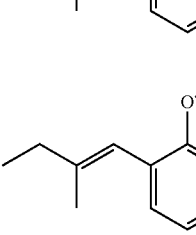 | [B-[3α(E),3a α]] |
| 201 | B12 | H | H | H | H | | [3α(E),3a α] |

TABLE 1-continued

| Comp. nr. | Ex. nr. | R⁸ a | b | c | d | R³ | Phys.data and stereochemistry |
|---|---|---|---|---|---|---|---|
| 197 | B12 | H | H | H | H | 2-chloro-6-fluorophenyl (E)-2-methylbut-1-enyl | [3α(E),3a α] |
| 198 | B12 | H | H | H | H | 2,5-difluorophenyl (Z)-2-methylbut-1-enyl | [3α(Z),3a α] |
| 199 | B12 | H | H | H | H | 2,5-difluorophenyl (E)-2-methylbut-1-enyl | [3α(E),3a α] |
| 202 | B12 | H | H | H | H | 2,3-difluorophenyl (Z)-2-methylbut-1-enyl | [3α(Z),3a α] |
| 203 | B12 | H | H | H | H | 2,3-difluorophenyl (E)-2-methylbut-1-enyl | [3α(E),3a α] |
| 157 | B13 | H | H | H | H | 1-naphthyl (E)-2-methylbut-1-enyl | cis |
| 65 | B9 | H | H | H | H | 2H-chromen-3-yl ethyl | cis |
| 21 | B9 | H | H | H | H | 3,4-dihydronaphthalen-2-yl ethyl | cis |

TABLE 1-continued

| Comp. nr. | Ex. nr. | R8 a | b | c | d | R3 | Phys.data and stereochemistry |
|---|---|---|---|---|---|---|---|
| 25 | B13 | H | H | H | H | (1-methyl-1-phenyl-but-1-enyl) | cis |
| 205 | B5b | H | H | H | H | (1-methyl-1-phenyl-but-1-enyl) | [3α(E),3a α] |
| 319 | B5b | H | H | H | H | (1-methyl-1-phenyl-but-1-enyl) | [A-[3α(E),3a α]] |
| 320 | B5b | H | H | H | H | (1-methyl-1-phenyl-but-1-enyl) | [B-[3α(E),3a α]] |
| 321 | B5b | H | H | H | H | (1-methyl-1-phenyl-but-1-enyl) | [B-[3α(E),3a α]] |
| 322 | B5b | H | H | H | H | (1-methyl-1-(3-hydroxyphenyl)-but-1-enyl) | [B-[3α(E),3a α]] |
| 323 | B6 | H | H | H | H | (1-methyl-1-(thien-3-yl)-but-1-enyl) | [B-[3α(E),3a α]] |
| 130 | B6 | H | H | H | H | (2-methyl-2-(thien-2-yl)-ethenyl) | [3α(E),3a α] |
| 18 | B6 | H | H | H | H | (2-methyl-2-(thien-3-yl)-ethenyl) | [3α(E),3a α] |

TABLE 1-continued
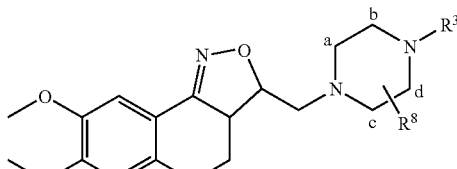
| Comp. nr. | Ex. nr. | a | b | c | d | R³ | Phys.data and stereochemistry |
|---|---|---|---|---|---|---|---|
| 324 | B6 | H | H | H | H | 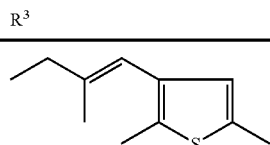 | [B-[3α(E),3a α]] |
| 325 | B6 | H | H | H | H | 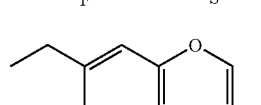 | [3α(Z),3a α] |
| 121 | B6 | H | H | H | H | 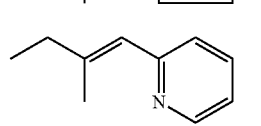 | [3α(E),3a α] |
| 23 | B11 | H | H | H | H | 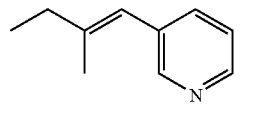 | [3α(Z),3a α] |
| 208 | B7 | H | H | H | H | 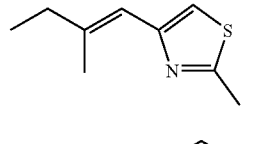 | [B-[3α(E),3a α]] |
| 326 | B6 | H | H | H | H | 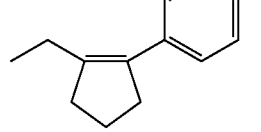 | [B-[3α(E),3a α]] |
| 145 | B6 | H | H | H | H | 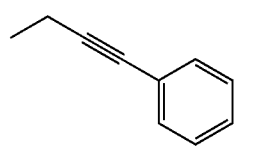 | cis |
| 122 | B6 | H | H | H | H | 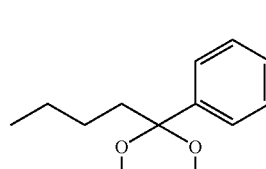 | cis |
| 63 | B5a | H | H | H | H | 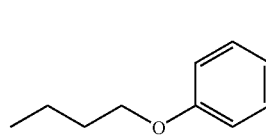 | cis |
| 40 | B5a | H | H | H | H |  | cis |

TABLE 1-continued

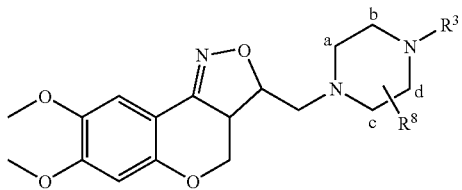

| Comp. nr. | Ex. nr. | R⁸ a | b | c | d | R³ | Phys.data and stereochemistry |
|---|---|---|---|---|---|---|---|
| 327 | B6 | H | H | H | H | 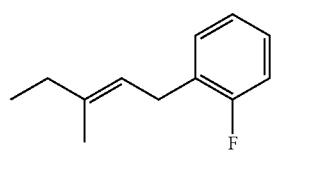 | [B-[3α(E),3a α]] |
| 127 | B9 | H | H | H | H | 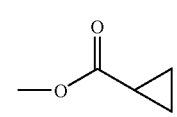 | [A-[3α(E),3a α]] |

TABLE 2A

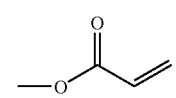

R¹ or R² not equal to —OCH₃

| Comp. nr. | Ex. nr. | R¹ | R² | R⁴ | R⁶ | Phys.data |
|---|---|---|---|---|---|---|
| 209 | B1a/B1b | H | H | H | | cis, E |
| 263 | B1a/B1b | H | H | H | c-COOMe | [3α(E),3a α] |
| 254 | B1a/B1b | H | F | CH₃ | | [3α(E),3a α] |
| 232 | B1f | H | OH | H | | [3α(E),3a α] |
| 237 | B1f | H | OH | CH₃ | | [3α(E),3a α] |
| 217 | B1a/B1b | H | OCH₃ | H | | [3α(E),3a α] |
| 229 | B1g | H | OCH₃ | H | | [A-[3α(E),3a α]];.HCl(1:2) |
| 230 | B1g | H | OCH₃ | H | | [B-[3α(E),3a α]];.HCl(1:2) |
| 328 | B1g | H | OCH₃ | CH₃ | | [3α(E),3a α] |
| 239 | B1f | H | OC₂H₄OCH₃ | CH₃ | | [3α(E),3a α] |
| 231 | B1a/B1b | H | OCH₂OC₂H₄OCH₃ | H | | [3α(E),3a α] |
| 236 | B1a/B1b | H | OCH₂OC₂H₄OCH₃ | CH₃ | | [3α(E),3a α] |
| 247 | B1f | H | OC₂H₄OC₂H₄OC₂H₄ | CH₃ | | [3α(E),3a α];.HCl(1:2) |
| 238 | B1f | H | O(C=O)NHC₂H₅ | CH₃ | | [3α(E),3a α] |
| 233 | B1f | H | O(C=O)CH₃ | H | | [3α(E),3a α] |
| 240 | B1f | H | O(C=O)CH₃ | CH₃ | | [3α(E),3a α] |
| 248 | B1f | H | O(C=O)C₂H₅ | CH₃ | | [3α(E),3a α] |
| 249 | B1f | H | O(C=O)CH₂OCH₃ | CH₃ | | [3α(E),3a α] |
| 250 | B1f | H | (cyclopropyl ester) | CH₃ | | [3α(E),3a α] |
| 329 | B1f | H | OC(=O)C(CH₃)₃ | CH₃ | | [3α(E),3a α] |
| 251 | B1f | H | (acrylate ester) | CH₃ | | [3α(E),3a α] |

TABLE 2A-continued

R¹ or R² not equal to —OCH₃

| Comp. nr. | Ex. nr. | R¹ | R² | R⁴ | R⁶ | Phys.data |
|---|---|---|---|---|---|---|
| 243 | B1f | H | methoxycyclopentyl | CH₃ | | [3α(E),3a α] |
| 330 | B1f | H | methyl isonicotinate group | CH₃ | | [3α(E),3a α] |
| 242 | B1f | H | OC₂H₄N(CH₃)₂ | CH₃ | | [3α(E),3a α] |
| 260 | B1f | H | OSO₂H | CH₃ | | [3α(E),3a α] |
| 211 | B1a/B1b | Cl | H | H | | [3α(E),3a α] |
| 246 | B1a/B1b | Cl | OCH₃ | CH₃ | | [3α(E),3a α] |
| 212 | B1a/B1b | Br | H | H | | [3α(E),3a α] |
| 214 | B1g | Br | H | H | | [A-[3α(E),3a α]] |
| 215 | B1g | Br | H | H | | [B-[3α(E),3a α]] |
| 235 | B1a/B1b | F | F | CH₃ | | [3α(E),3a α] |
| 241 | B1f | F | OCH₃ | CH₃ | | [3α(E),3a α] |
| 216 | B1f | phenyl | H | H | | [3α(E),3a α] |
| 219 | B1a/B1b | CH₃ | H | H | | [3α(E),3a α] |
| 244 | B1f | F | SCH₃ | CH₃ | | [3α(E),3a α] |
| 331 | B1f | OH | OH | CH₃ | | [B-[3α(E),3a α]] HCl(1:2) |
| 255 | B1c | OH | OCH₃ | CH₃ | | [3α(E),3a α] |
| 257 | B1f | O(C=O)CH₃ | OCH₃ | CH₃ | | [3α(E),3a α] |
| 332 | B1f | OC₂H₄OC(=O)—CH₃ | OCH₃ | CH₃ | | [3α(E),3a α] |
| 333 | B1f | O(C=O)CH₃ | OCH₃ | CH₃ | | [B-[3α(E),3a α]] |
| 213 | B1a/B1b | OCH₃ | H | H | | [3α(E),3a α] |
| 3 | B1c | OCH₃ | OH | CH₃ | | [3α(E),3a α] |
| 6 | B1f | OCH₃ | O(C=O)CH₃ | CH₃ | | [3α(E),3a α] |
| 334 | B1f | OCH₃ | O(C=O)CH₃ | CH₃ | b-F | [B-[3α(E),3a α]] |
| 335 | B1f | OCH₃ | O(C=O)CH₃ | CH₃ | c-F | [B-[3α(E),3a α]] |
| 336 | B1f | OCH₃ | O(C=O)CH₃ | H | c-F | [B-[3α(E),3a α]] |
| 337 | B1f | OCH₃ | methoxymethylcyclopropyl | CH₃ | c-F | [B-[3α(E),3a α]] |
| 338 | B1f | OCH₃ | methyl cyclopropanecarboxylate group | CH₃ | | [B-[3α(E),3a α]] |
| 339 | B1f | OCH₃ | methyl nicotinate group | CH₃ | | [B-[3α(E),3a α]] |
| 340 | B1f | OCH₃ | OC(=O)NHC₂H₅ | CH₃ | | [B-[3α(E),3a α]] |
| 341 | B1f | OCH₃ | OC₂H₅N(CH₃)₂ | CH₃ | | [B-[3α(E),3a α]] |
| 342 | B1f | OCH₃ | OCH₂OC₂H₄OCH₃ | CH₃ | | [B-[3α(E),3a α]] |
| 343 | B1f | OCH₃ | OC(=O)OCH₃ | CH₃ | | [B-[3α(E),3a α]] |
| 344 | B1f | OCH₃ | OCH₂CH=CH₂ | CH₃ | | [B-[3α(E),3a α]] |
| 345 | B1f | OCH₃ | OCH₂CH₂OH | CH₃ | | [B-[3α(E),3a α]] HCl(1:2) |
| 346 | B1f | OCH₃ | OSO₂—CH₃ | CH₃ | | [B-[3α(E),3a α]] |

TABLE 2A-continued

R¹ or R² not equal to —OCH₃

| Comp. nr. | Ex. nr. | R¹ | R² | R⁴ | R⁶ | Phys.data |
|---|---|---|---|---|---|---|
| 348 | B1f | OCH₃ | H | CH₃ | | [3α(E),3a α]] |
| 349 | B1f | OCH₃ | phenyl | CH₃ | | [3α(E),3a α]] |
| 350 | B1f | OCH₃ | SCH₃ | CH₃ | | [3α(E),3a α]] Trifluoroacetate (1:1) |

TABLE 2B

R¹ or R² not equal to —OCH₃

| Comp. nr. | Ex. nr. | R⁷ | R¹ | R² | R⁴ | R⁶ | Phys.data |
|---|---|---|---|---|---|---|---|
| 210 | B2a | H | H | H | H | | [3α(E),3a α] |
| 234 | B2a | H | H | H | CH₃ | | [3α(E),3a α] |
| 256 | B1a/B1b | H | OCH₃ | OCH₃ | H | | [3α(E),3a α] |
| 351 | B1a/B1b | H | OCH₃ | OCH₃ | H | b-F | [3α(E),3a α] |
| 352 | B1a/B1b | H | OCH₃ | OCH₃ | H | b-F | [A-[3α(E),3a α]] |
| 353 | B1a/B1b | H | OCH₃ | OCH₃ | H | b-F | [B-[3α(E),3a α]] |
| 354 | B1a/B1b | H | OCH₃ | OCH₃ | H | c-F | [3α(E),3a α] |
| 258 | B1a/B1b | H | OCH₃ | OCH₃ | H | | [3α(E),3a α] |
| 12 | B3b | H | OCH₃ | OCH₃ | CH₃ | | [A-[3α(E),3a α]] |
| 253 | B3b | H | OCH₃ | OCH₃ | CH₃ | | [B-[3α(E),3a α]] |
| 11 | B3a | H | OCH₃ | OCH₃ | CH₃ | | [3α(E),3a α] |
| 223 | B16 | H | OCH₃ | OCH₃ | H | | [3α(E),3a α] |
| 261 | B1f | H | H | OCH₃ | CH₃ | | [3α(E),3a α] |
| 228 | B2b | CH₃ | H | H | H | | [3α(E),3a α] |
| 252 | B3a | CH₃ | OCH₃ | OCH₃ | CH₃ | | [3α(E),3a α] |
| 259 | B1a/B1b | benzyl | H | OCH₃ | CH₃ | | [3α(E),3a α] |
| 222 | B16 | C(=O)CF₃ | OCH₃ | OCH₃ | H | | [3α(E),3a α] |
| 224 | B2b | C(=O)CF₃ | H | H | H | | [3α(E),3a α] |
| 225 | B2b | C(=O)CH₃ | H | H | H | | [3α(E),3a α] |
| 226 | B2b | C(=O)OC₂H₅ | H | H | H | | [3α(E),3a α] |
| 227 | B2b | C(=O)NHC₂H₅ | H | H | H | | [3α(E),3a α] |

TABLE 2C

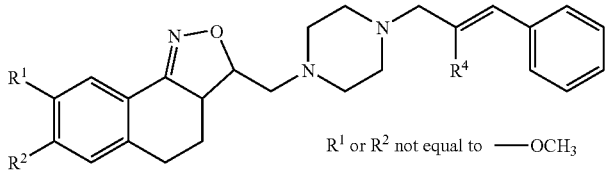

R¹ or R² not equal to —OCH₃

| Comp. nr. | Ex. nr. | R¹ | R² | R⁴ | Phys.data |
|---|---|---|---|---|---|
| 220 | B16 | H | OCH₃ | H | [3α(E),3a α]; .HCl(1:2) |
| 218 | B5a | H | H | H | [3α(E),3a α] |

TABLE 3A

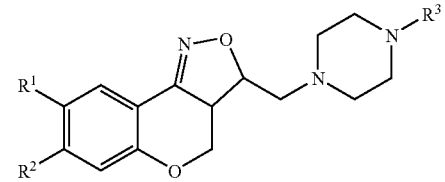

| Comp nr. | Ex. nr. | R¹ | R² | R³ | Phys.data |
|---|---|---|---|---|---|
| 262 | B1a/B1b | H | H | -CH₂-C₆H₅ (phenethyl) | cis |
| 264 | B1a/B1b | H | H | -(CH₂)₃-C₆H₅ | cis |
| 265 | B1a/B1b | H | OCH₃ | -CH₂CH₂-(2-naphthyl) | cis; HCl(1:2) |
| 267 | B1a/B1b | H | -OCH₂OCH₂CH₂OCH₃ | -CH₂CH₂-(2-naphthyl) | cis |
| 268 | B1f | H | OH | -CH₂CH₂-(2-naphthyl) | cis |
| 269 | B1f | H | -OCH₂-cyclopropyl | -CH₂CH₂-(2-naphthyl) | cis |
| 270 | B1f | H | -OCHF₂ | -CH₂CH₂-(2-naphthyl) | cis |
| 271 | B1f | H | -O-(tetrahydrofuran-3-yl) | -CH₂CH₂-(2-naphthyl) | [3α(E),3a α] |

TABLE 3A-continued
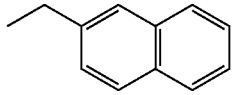
| Comp nr. | Ex. nr. | R¹ | R² | R³ | Phys.data |
|---|---|---|---|---|---|
| 273 | B1f | H | O(C=O)CH₃ | 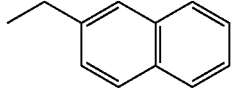 | cis |
| 355 | B1f | OCH₃ | O(C=O)CH₃ | 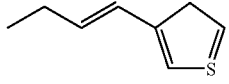 | B-cis |
| 357 | B1f | OCH₃ | O(C=O)CH₃ | 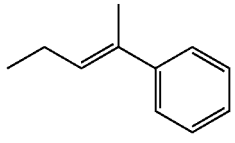 | [B-[3α(E),3a α]] |
| 358 | B1f | OCH₃ | O(C=O)CH₃ | 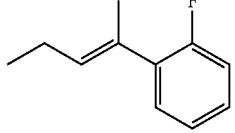 | [B-[3α(E),3a α]] |
| 359 | B1f | OCH₃ | OCH₃ | 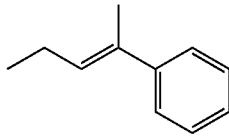 | [B-[3α(E),3a α]] |
| 360 | B1f | OCH₃ | OCH₃ | 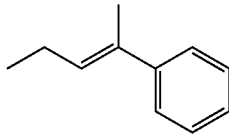 | [B-[3α(E),3a α]] |
| 361 | B1f | OCH₃ | OCH₃ | 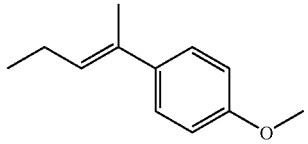 | [B-[3α(E),3a α]] |
| 362 | B1f | OCH₃ | OCH₃ | 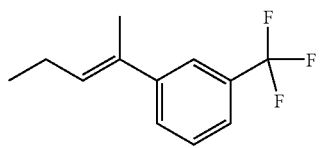 | [B-[3α(E),3a α]] |
| 363 | B1f | OCH₃ | OCH₃ |  | [B-[3α(E),3a α]] |

TABLE 3A-continued
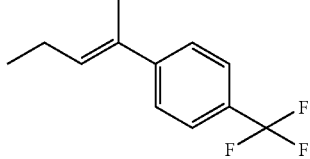
| Comp nr. | Ex. nr. | R¹ | R² | R³ | Phys.data |
|---|---|---|---|---|---|
| 364 | B1f | OCH₃ | OCH₃ | 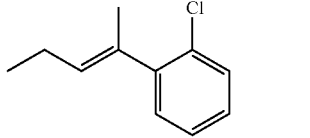 | [B-[3α(E),3a α]] |
| 365 | B1f | OCH₃ | OCH₃ | 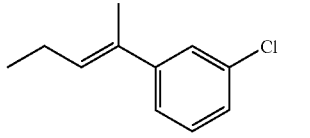 | [B-[3α(E),3a α]] |
| 366 | B1f | OCH₃ | OCH₃ | 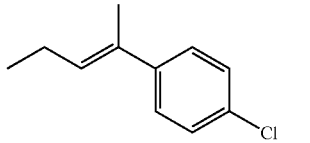 | [B-[3α(E),3a α]] |
| 367 | B1f | OCH₃ | OCH₃ | 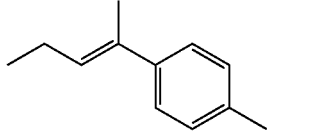 | [B-[3α(E),3a α] |
| 368 | B1f | OCH₃ | OCH₃ | 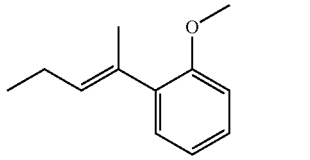 | [B-[3α(E),3a α]] |
| 369 | B1f | OCH₃ | OCH₃ | 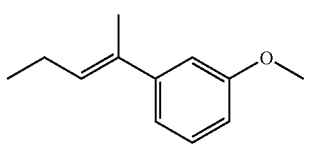 | [B-[3α(E),3a α]] |
| 370 | B1f | OCH₃ | OCH₃ | 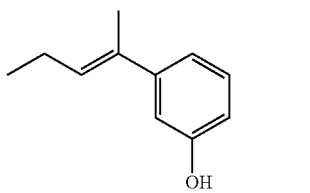 | [B-[3α(E),3a α]] |
| 371 | B1f | OCH₃ | OCH₃ |  | [B-[3α(E),3a α]] |

TABLE 3A-continued
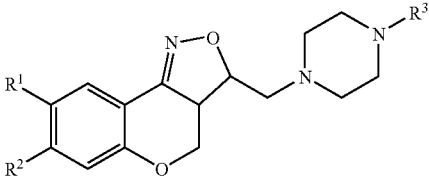
| Comp nr. | Ex. nr. | R¹ | R² | R³ | Phys.data |
|---|---|---|---|---|---|
| 372 | B1f | OCH₃ | OCH₃ | 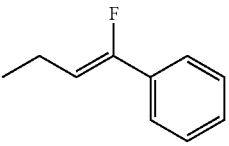 | [B-[3α(E),3a α]] HCl(1:2) |
| 373 | B1f | OCH₃ | OCH₃ | 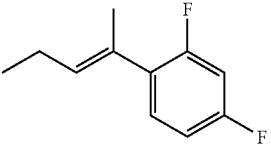 | [B-[3α(E),3a α]] |
| 374 | B1f | OCH₃ | OCH₃ | 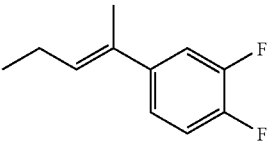 | [B-[3α(E),3a α]] |
| 375 | B1f | OCH₃ | OCH₃ | 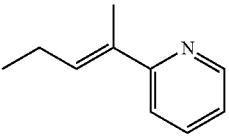 | [B-[3α(E),3a α]] |
| 376 | B1f | OCH₃ | OCH₃ | 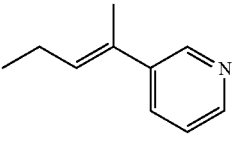 | [B-[3α(E),3a α]] |
| 377 | B1f | OCH₃ | OCH₃ | 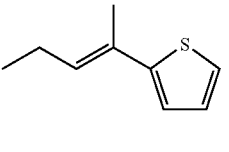 | [B-[3α(E),3a α]] |
| 378 | B1f | OCH₃ | OCH₃ | 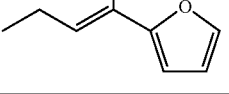 | [B-[3α(E),3a α]] |

TABLE 3B
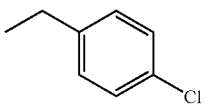
| Comp nr. | Ex. nr. | R⁷ | R¹ | R² | R³ | Phys.data |
|---|---|---|---|---|---|---|
| 275 | B5a | H | OCH₃ | OCH₃ | 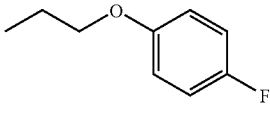 | cis |
| 274 | B5a | H | OCH₃ | OCH₃ | 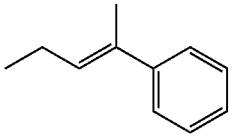 | cis |
| 379 | B1f | H | OCH₃ | OCH₃ | 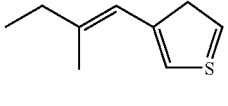 | [3α(E),3a α] |
| 380 | B1f | H | OCH₃ | OCH₃ | 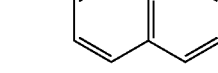 | [3α(E),3a α] |
| 272 | B5a | H | OCH₃ | OCH₃ | 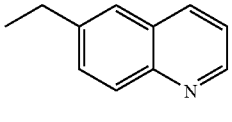 | cis |
| 276 | B5a | H | OCH₃ | OCH₃ | 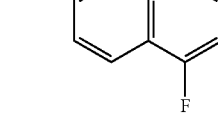 | cis |
| 381 | B5a | H | OCH₃ | OCH₃ | 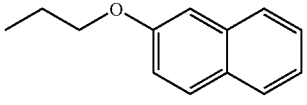 | cis |
| 382 | B5a | H | OCH₃ | OCH₃ | 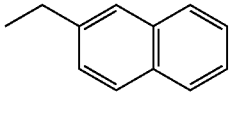 | |
| 9 | B2a | H | H | H | 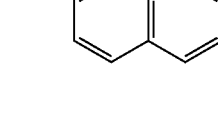 | cis |
| 10 | B2b | C(=O)CH₃ | H | H |  | cis |

TABLE 3B-continued
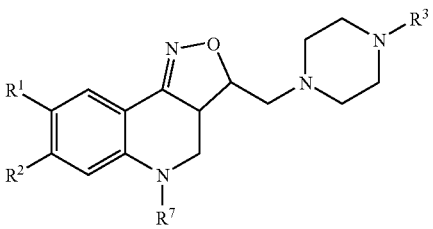
| Comp nr. | Ex. nr. | R⁷ | R¹ | R² | R³ | Phys.data |
|---|---|---|---|---|---|---|
| 266 | B2b | CH₃ | H | H | 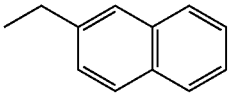 | cis |
TABLE 3C
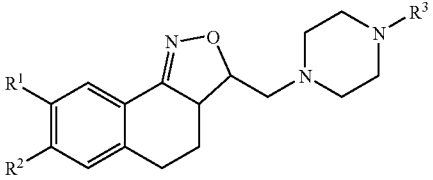
| Comp nr. | Ex. nr. | R¹ | R² | R³ | Phys.data |
|---|---|---|---|---|---|
| 28 | B16 | H | OCH₃ | 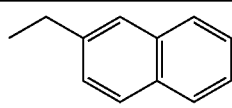 | cis; HCl(1:2) |
TABLE 4
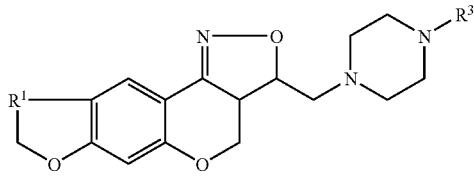
| Comp. nr. | Ex. nr. | R¹ | R³ | Phys.data |
|---|---|---|---|---|
| 277 | B1a/B1b | O | 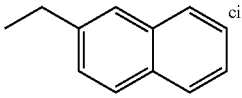 | cis; .HCl(1:2) |
| 278 | B1a/B1b | O | 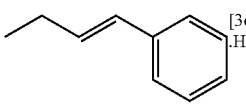 | [3α(E),3a α]; .HCl(1:2) |
TABLE 4-continued
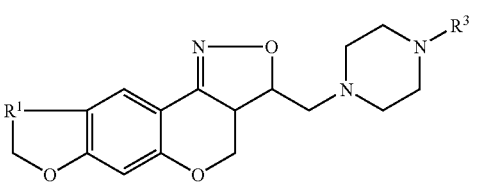
| Comp. nr. | Ex. nr. | R¹ | R³ | Phys.data |
|---|---|---|---|---|
| 279 | B1a/B1b | CH₃ | 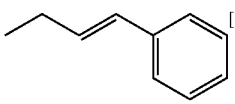 | [3α(E),3a α] |

TABLE 5

| Comp. nr. | Ex. nr. | R¹ | m | Pir | Phys.data |
|---|---|---|---|---|---|
| 280 | B1a/B1b | H | 2 | —N(piperazine)N— | trans |
| 29 | B17 | OCH₃ | 1 | —NH—(piperidine)N— | cis |
| 281 | B17 | OCH₃ | 1 | —NMe—(piperidine)N— | cis |
| 282 | B17 | OCH₃ | 1 | —N(CHO)—(piperidine)N— | cis |
| 283 | B17 | OCH₃ | 1 | —N(piperazine)N—CH₂—NH— | cis |

C. Pharmacological Examples

EXAMPLE C1

Binding Experiment for $\alpha_2$-Adrenergic Receptor Subtypes and for 5-HT Transporter General The interaction of the compounds of Formula (I) with h$\alpha_2$-receptors and h5-HT-transporters was assessed in in vitro radioligand binding experiments. In general, a low concentration of a radioligand with a high binding affinity for a particular receptor or transporter is incubated with a sample of a tissue preparation enriched in a particular receptor or transporter or with a preparation of cells expressing cloned human receptors in a buffered medium. During the incubation, the radioligand binds to the receptor or transporter. When equilibrium of binding is reached, the receptor bound radioactivity is separated from the nonbound radioactivity, and the receptor- or transporter-bound activity is counted. The interaction of the test compounds with the receptor is assessed in competition binding experiments. Various concentrations of the test compound are added to the incubation mixture containing the receptor- or transporter preparation and the radioligand. The test compound in proportion to its binding affinity and its concentration inhibits binding of the radioligand. The radioligand used for h$\alpha_{2A}$, h$\alpha_{2B}$ and h$\alpha_{2C}$ receptor binding was [³H]-raulwolscine and for the h5-HT transporter was [³H]paroxetine.

Cell Culture and Membrane Preparation

CHO cells, stabile transfected with human adrenergic-$\alpha_{2A}$-, -$\alpha_{2B}$ or $\alpha_{2C}$ receptor cDNA, were cultured in Dulbecco's Modified Eagle's Medium (DMEM)/Nutrient mixture Ham's F12 (ratio 1:1)(Gibco, Gent-Belgium) supplemented with 10% heat inactivated fetal calf serum (Life Technologies, Merelbeke-Belgium) and antibiotics (100 IU/ml penicillin G, 100 μg/ml streptomycin sulphate, 110 μg/ml pyruvic acid and 100 μg/ml L-glutamine). One day before collection, cells were induced with 5 mM sodiumbutyrate. Upon 80–90% of confluence, cells were scraped in phosphate buffered saline without $Ca^{2+}$ and $Mg^{2+}$ and collected by centrifugation at 1500×g for 10 min. The cells were homogenised in Tris-HCl 50 mM using an Ultraturrax homogenizer and centrifuged for 10 min at 23,500×g. The pellet was washed once by resuspension and rehomogenization and the final pellet was resuspended in Tris-HCl, divided in 1 ml aliquots and stored at −70° C.

Binding Experiment for $\alpha_2$-Adrenergic Receptor Subtypes

Membranes were thawed and re-homogenized in incubation buffer (glycylglycine 25 mM, pH 8.0). In a total volume of 500 μL, 2–10 μg protein was incubated with [³H]raulwolscine (NET-722) (New England Nuclear, USA) (1 nM final concentration) with or without competitor for 60 min at 25° C. followed by rapid filtration over GF/B filter using a Filtermate196 harvester (Packard, Meriden, Conn.). Filters were rinsed extensively with ice-cold rinsing buffer (Tris-HCl 50 mM pH 7.4). Filter-bound radioactivity was determined by scintillation counting in a Topcount (Packard, Meriden, Conn.) and results were expressed as counts per minute (cpm). Non-specific binding was determined in the presence of 1 μM oxymetazoline for h$\alpha_{2A}$- and h$\alpha_{2B}$ receptors and 1 μM spiroxatrine for h$\alpha_{2C}$ receptors.

Binding Experiment for 5-HT Transporter

Human platelet membranes (Oceanix Biosciences Corporation, Hanover, Md., USA) were thawed, diluted in buffer (Tris-HCl 50 mM, 120 mM NaCl and 5 mM KCl) and quickly (max 3 s) homogenised with an Ultraturrax homogenizer. In a total volume of 250 μL, 50–100 μg protein was incubated with [³H]paroxetine (NET-869) (New England Nuclear, USA) (0.5 nM final concentration) with or without competitor for 60 min at 25° C. Incubation was stopped by rapid filtration of the incubation mixture over GF/B filters, pre-wetted with 0.1% polyethyleneamine, using a Filtermate196 harvester (Packard, Meriden, Conn.). Filters were rinsed extensively with ice-cold buffer and radioactivity on the filters was counted in a Topcount liquid scintillation counter (Packard, Meriden, Conn.). Data were expressed as cpm. Imipramine (at 1 μM final concentration) was used to determine the non-specific binding.

Data Analysis and Results

Data from assays in the presence of compound were calculated as a percentage of total binding measured in the absence of test compound. Inhibition curves, plotting percent of total binding versus the log value of the concentration of the test compound, were automatically generated, and sigmoidal inhibition curves were fitted using non-linear regression. The $pIC_{50}$ values of test compounds were derived from individual curves.

All compounds according to formula (I) produced an inhibition at least at the $h\alpha_{2A}$ site (but often also at the $h\alpha_{2B}$ and $h\alpha_{2C}$ sites) and simultaneously at the 5-HT transporter site of more than 50% ($pIC_{50}$) at a test concentration ranging between $10^{-6}$ M and $10^{-9}$ M in a concentration-dependent manner. For a selected number of compounds, covering most of the various embodiments of Formula (I), the results of the in vitro studies are given in Table 6.

TABLE 6

Some results of the in vitro experiments ($pIC_{50}$-values).

| Comp nr. | $h\alpha_{2A}$ | $h\alpha_{2B}$ | $h\alpha_{2C}$ | 5HTT |
|---|---|---|---|---|
| 1 | 8.20 | 8.49 | 8.96 | 8.29 |
| 3 | 8.63 | 8.59 | 8.73 | 7.79 |
| 8 | 8.34 | 8.14 | 7.92 | 7.75 |
| 9 | 7.99 | 8.33 | 6.97 | 8.80 |
| 14 | 6.37 | 6.19 | 6.58 | 6.44 |
| 15 | 7.90 | 7.84 | 7.94 | 7.77 |
| 16 | 8.27 | 8.21 | 8.17 | 8.43 |
| 21 | 8.79 | 7.73 | 8.98 | 8.92 |
| 24 | 7.86 | 8.41 | 8.54 | 8.26 |
| 26 | 6.28 | 6.99 | 6.61 | 6.17 |
| 27 | 8.39 | 8.22 | 8.81 | 7.74 |
| 28 | 8.11 | 7.74 | 7.15 | 8.36 |
| 29 | 6.33 | 6.66 | 6.72 | 8.26 |
| 31 | 6.10 | 6.20 | 6.00 | 6.30 |
| 32 | 7.90 | 7.84 | 7.94 | 7.77 |
| 41 | 7.80 | 8.30 | 7.90 | 8.50 |
| 43 | 6.99 | 7.19 | 6.86 | 7.80 |
| 45 | 7.24 | 7.15 | 7.36 | 7.16 |
| 47 | 6.18 | 6.35 | 6.07 | 7.30 |
| 48 | 7.88 | 8.24 | 8.36 | 6.90 |
| 54 | 7.72 | 7.42 | 7.44 | 7.38 |
| 65 | 7.88 | 7.74 | 8.29 | 8.29 |
| 72 | 7.33 | 6.75 | 7.18 | 8.16 |
| 76 | 7.14 | 7.05 | 7.60 | 8.80 |
| 79 | 6.00 | 6.00 | 6.00 | 6.00 |
| 81 | 6.00 | 6.00 | 6.00 | 6.84 |
| 90 | 6.71 | 6.00 | 7.04 | 6.52 |
| 97 | 6.00 | 6.00 | 6.00 | 6.45 |
| 110 | 7.16 | 6.95 | 7.46 | 7.52 |
| 125 | 7.25 | 6.85 | 7.46 | 7.87 |
| 127 | 6.85 | 6.91 | 7.59 | 7.20 |
| 129 | 7.91 | 8.01 | 8.17 | 8.55 |
| 143 | 7.11 | 7.60 | 7.63 | 7.62 |
| 154 | 7.27 | 7.39 | 7.06 | 7.05 |
| 157 | 7.87 | 7.28 | 7.13 | 7.48 |
| 181 | 6.55 | 6.11 | 6.49 | 7.63 |
| 185 | 6.84 | 7.11 | 7.53 | 7.90 |
| 195 | 8.34 | 8.80 | 8.68 | 8.70 |

TABLE 6-continued

Some results of the in vitro experiments ($pIC_{50}$-values).

| Comp nr. | $h\alpha_{2A}$ | $h\alpha_{2B}$ | $h\alpha_{2C}$ | 5HTT |
|---|---|---|---|---|
| 196 | 7.84 | 8.44 | 8.09 | 8.41 |
| 199 | 8.92 | 9.00 | 8.78 | 7.89 |
| 201 | 8.36 | 8.49 | 8.34 | 8.12 |
| 217 | 8.78 | 8.21 | 7.85 | 7.27 |
| 218 | 6.74 | 6.88 | 5.90 | 6.34 |
| 220 | 8.12 | 7.85 | 7.36 | 7.18 |
| 224 | 6.96 | 7.66 | 7.13 | 7.31 |
| 226 | 6.85 | 7.09 | 6.96 | 8.08 |
| 233 | 8.33 | 8.20 | 7.94 | 7.36 |
| 234 | 8.57 | 8.88 | 8.41 | 7.71 |
| 237 | 9.11 | 8.90 | 8.93 | 7.94 |
| 238 | 8.56 | 8.62 | 8.59 | 8.07 |
| 239 | 9.31 | 8.62 | 9.54 | 7.85 |
| 241 | 7.78 | 8.13 | 8.20 | 7.01 |
| 242 | 9.49 | 9.44 | 8.97 | 7.95 |
| 243 | 8.27 | 7.77 | 8.29 | 6.75 |
| 244 | 8.42 | 8.13 | 8.87 | 6.90 |
| 246 | 7.55 | 7.90 | 7.86 | 7.50 |
| 250 | 8.40 | 8.17 | 8.48 | 7.09 |
| 251 | 8.43 | 8.31 | 8.26 | 6.89 |
| 253 | 8.24 | 7.94 | 7.98 | 6.60 |
| 257 | 7.52 | 8.37 | 8.65 | 7.46 |
| 260 | 8.61 | 8.21 | 8.59 | 7.22 |
| 265 | 8.46 | 7.68 | 7.56 | 7.83 |
| 266 | 7.84 | 7.80 | 7.45 | 8.88 |
| 267 | 8.49 | 7.90 | 8.55 | 8.30 |
| 268 | 9.00 | 8.26 | 8.05 | 8.24 |
| 271 | 8.41 | 7.86 | 7.37 | 8.53 |
| 272 | 6.50 | 7.57 | 6.87 | 8.32 |
| 273 | 8.11 | 7.68 | 7.51 | 7.88 |
| 277 | 8.61 | 8.10 | 7.77 | 6.97 |
| 278 | 8.49 | 8.14 | 8.16 | 6.61 |
| 279 | 8.45 | 8.03 | 8.24 | 7.45 |
| 280 | 7.04 | 6.35 | 6.42 | 8.09 |
| 281 | 7.05 | 7.19 | 7.31 | 7.25 |
| 282 | 7.66 | 7.26 | 7.64 | 8.06 |
| 283 | 7.00 | 7.33 | 7.13 | 8.89 |
| 285 | 6.22 | 6.24 | 6.44 | 6.59 |
| 291 | 6.07 | 6.00 | 6.00 | 6.00 |
| 296 | 6.12 | 6.39 | 6.14 | 6.06 |
| 300 | 6.46 | 6.03 | 6.20 | 6.14 |
| 304 | 7.71 | 7.23 | 7.19 | 7.41 |
| 309 | 7.30 | n.d. | 7.23 | 6.41 |
| 310 | 6.67 | n.d. | 7.19 | 6.06 |
| 312 | 8.08 | n.d. | 8.20 | 7.62 |
| 314 | 7.95 | 8.16 | 8.19 | 8.06 |
| 316 | 7.98 | 6.76 | 6.92 | 6.39 |
| 320 | 8.23 | 7.70 | 8.17 | 7.49 |
| 323 | 8.21 | n.d. | 8.02 | 7.82 |
| 329 | 7.70 | 7.56 | 7.74 | 7.48 |
| 332 | 8.35 | n.d. | 9.22 | 7.23 |
| 333 | 8.32 | 8.42 | 8.33 | 7.52 |
| 334 | 8.57 | n.d. | 8.64 | 7.58 |
| 337 | 7.68 | n.d. | 7.88 | 7.88 |
| 340 | 9.00 | n.d. | 8.42 | 7.64 |
| 341 | 8.44 | n.d. | 8.91 | 8.66 |
| 342 | 8.07 | n.d. | 9.79 | 7.76 |
| 343 | 8.63 | n.d. | 8.91 | 7.43 |
| 344 | 8.45 | n.d. | 8.68 | 8.00 |
| 346 | 8.65 | n.d. | 8.91 | 8.37 |
| 348 | 8.92 | n.d. | 8.88 | 7.75 |
| 350 | 8.39 | n.d. | 8.68 | 7.69 |
| 351 | 7.95 | 8.16 | 8.19 | 8.06 |
| 355 | 8.29 | n.d. | 8.15 | 7.87 |
| 358 | 8.83 | n.d. | 8.49 | 7.43 |
| 359 | 8.10 | n.d. | 8.46 | 7.35 |
| 361 | 7.90 | n.d. | 8.51 | 8.38 |
| 366 | 7.89 | n.d. | 8.48 | 7.94 |
| 379 | 7.56 | 7.71 | 7.39 | 7.46 |
| 380 | 7.78 | 8.35 | 7.99 | 7.63 | n.d.: not determined.

EXAMPLE C2

In Vivo Experiment for α₂-Adrenoceptor Antagonism and for Serotonine (5-HT) Reuptake Activity A. Medetomidine-test The onset and end of medetomidine (0.10 mg/kg, i.v.)-induced loss of righting was recorded in overnight-starved Wiga male rats (200–250 g). The intensity of the loss of righting was scored: 0=normal behaviour, 1=slight ataxia, 2=pronounced ataxia, 3=loss of righting for a period<5 min, 4=loss of righting for a period>5 min. Under standard conditions, test compound or solvent was administered (s.c. or p.o.) 1 h before medetomidine. Criterion for drug-induced antagonism: (1) antagonism of loss of righting: duration=0 min (1.4% false positive controls; n=74) (2) reversal of ataxia: score<2 (0% false positives). Criterion for drug-induced potentiation: loss of righting reflex over a period longer than 120 min (0% false positives). Centrally acting α₂-adrenoceptor antagonists or behavioural stimulants antagonise the loss of righting; sedative compounds may result in prolongation.

The following observations were made: onset of loss of righting (min), end of loss of righting (min) and intensity of loss of righting (score 0–4). The observations were performed at 1 h following s.c. (solutions) or p.o. (suspensions) administration, respectively. Starting dose was 10 mg/kg (References: Berger, U. V., Grzanna, R., Molliver, M. E., *Exp. Neurol.* 103, 111–115 (1989), Fuller, R. W., Perry, K. W., Molloy, B. B., *Eur. J. Pharmacol.* 33, 119–124 (1975) and Lassen, B. J., *Psychopharmacol.* 57, 151–153 (1978)).

B. pCA-test

Male Wiga rats were used (body weight: 200±20 g). One hour after administration of test compound or solvent, a solution of pCA was injected subcutaneously (5 mg/kg; 10 ml/kg). Forty-five minutes after the pCA injection, head-twitches (HTW) are counted and the excitation (EXC) were scored over three successive 5 min intervals (starting 45, 50 and 55 minutes after pCA-administration. The scores were given by a trained observator according to the intensity scale: 0=absent or doubtful, 1=present, 2=pronounced, 3=maximal. For statistical analysis, the head-twitches counted during the 15-min observation time were cumulated. For the other phenomena, the median value of the three 5-min-intervals was used.

Standard observations were performed at 1 h following s.c. or p.o. administration. The starting dose was in general 10 mg/kg. Doses were initially given to 2 animals. When both animals show activity for at least one of the observations, the compound was considered active and testing was repeated at a 4 times lower dose. When activity was found in only one out of the two animals, an additional animal was tested. When activity was found in this additional animal, the compound was also considered to be active and testing was repeated at a 4 times lower dose. In all other cases the compound was considered inactive at the particular time-route-dose (Reference: Janssen, P. A. J., Niemegeers, C. J. E., Awouters, F., Schellekens, K. H. L., Megens, A. A. H. P., Meert, T. F J. *Pharmacol. Exp. Therap.* 244, 685–693 (1988)).

Results

A large number of compounds according to the invention showed a central activity (minimal effective dose) both in the medetomidine test and in the pCA-test of less than or equal to 10 mg/kg.

EXAMPLE C3

[³⁵S]GTPγS Binding Assay

Membranes of the hα₂ₐ adrenoceptor expressing CHO cell line were thawed and re-homogenised in 20 mM Hepes buffer. The incubation medium consisted of: 20 mM Hepes buffer, pH 7.5, 1 μM GDP, 3 mM MgCl₂, 100 mM NaCl, 0.25 nM [³⁵S]GTPγS and 10 μg protein per well of a 96-well plate. Antagonists and the reference agonist noradrenaline (3 μM) were added 20 min before the [³⁵S]GTPγS. The incubation (20 min, 37° C.) was ended by rapid filtration through GF/B filters and binding quantified by liquid scintillation counting.

RESULTS

All compounds according to the invention evaluated in the GTPγS binding assay did not show significant increases of [³⁵S]GTPγS binding to the hα₂ₐ receptor up to 10 μM. All compounds evaluated in the assay were able to inhibit noradrenaline-induced increases of [³⁵S]GTPγS binding, thereby showing their antagonistic nature at this receptor.

The invention claimed is:

1. A compound according to the general Formula (I)

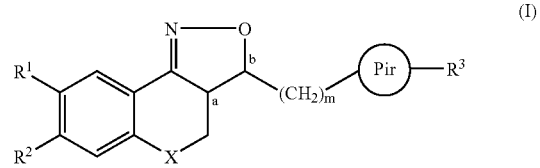

the pharmaceutically acceptable acid or base addition salts thereof, the stereochemically isomeric forms thereof and the N-oxide form thereof, wherein:

X is $CH_2$, N—$R^7$, S or O;

$R^7$ is selected from the group consisting of hydrogen, alkyl, phenyl, phenylalkyl, alkylcarbonyl, alkyloxycarbonyl and mono- and dialkylaminocarbonyl, the phenyl and alkyl groups being optionally substituted with one or more halo atoms;

$R^1$ and $R^2$ are each, independently from each other, selected from the group consisting of hydrogen, hydroxy, cyano, halo, $OSO_2H$, $OSO_2CH_3$, phenyl, phenylalkyl, alkyloxy, alkyloxyalkyloxy, alkyloxyalkyloxyalkyloxy, tetrahydrofuranyloxy, alkylcarbonyloxy, alkylthio, alkyloxyalkylcarbonyloxy, pyridinylcarbonyloxy, alkylcarbonyloxyalkyloxy, alkyloxycarbonyloxy, alkenyloxy, alkenylcarbonyloxy and mono- and dialkylaminoalkyloxy, the alkyl and aryl radicals being optionally substituted with one or more hydroxy or halo atoms or amino groups; or $R^1$ and $R^2$ may be taken together to form a bivalent radical —$R^1$—$R^2$— selected from the group consisting of —$CH_2$—$CH_2$—O—, —O—$CH_2$—$CH_2$—, —O—$CH_2$—O—, —$CH_2$—O—$CH_2$— and —O—$CH_2$—$CH_2$—O—;

a and b are asymmetric centers;

$(CH_2)_m$ is a straight hydrocarbon chain of m carbon atoms, m being an integer ranging from 1 to 4;

Pir is an optionally substituted radical according to any one of Formula (IIa), (IIB or (IIc)

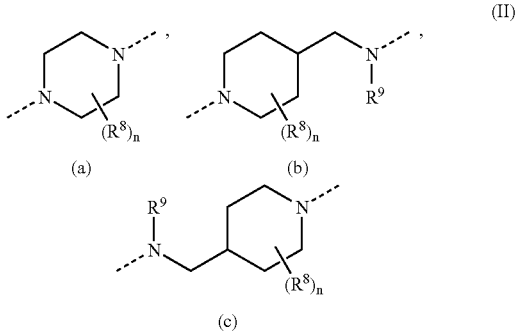

wherein:
each $R^8$ is independently from each other, selected from the group consisting of hydrogen, hydroxy, amino, nitro, cyano, halo and alkyl;
n is an integer ranging from 1 to 5;
$R^9$ is selected from the group consisting of hydrogen, alkyl and formyl; and
$R^3$ is a radical according to any one of Formula (III)

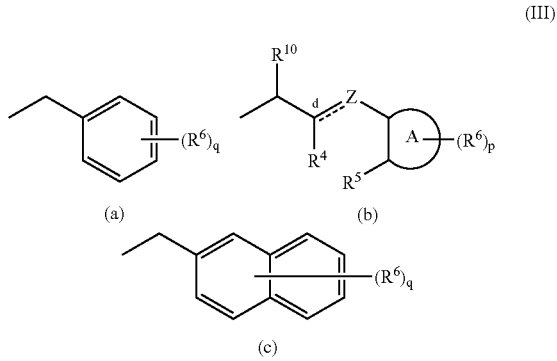

wherein:
d is a single bond while Z is a bivalent radical selected from the group consisting of —$CH_2$—, —C(=O)—, —CH(OH)—, —C(=N—OH)—, —CH(alkyl)-, —O—, —S—, —S(=O), and —NH—; or d is a double bond while Z is a trivalent radical of formula =CH— or =C(alkyl);
A is a 5- or 6-membered aromatic homocyclic or heterocyclic ring, selected from the group consisting of phenyl, pyranyl, pyridinyl, pyrazinyl, pyrimidinyl, pyridazinyl, thienyl, isothiazolyl, pyrrolyl, imidazolyl, pyrazolyl, furanyl, oxadiazolyl and isoxazolyl;
p is an integer ranging from 0 to 4;
q is an integer ranging from 0 to 7;
$R^4$ is selected from the group consisting of hydrogen, alkyl, phenyl, biphenyl, naphthyl, halo and cyano, the alkyl and aryl radicals being optionally substituted with one or more hydroxy or halo atoms or amino groups;
$R^5$ is equal to $R^4$; or
$R^4$ and $R^5$ may be taken together to form a bivalent radical —$R^4$—$R^5$— selected from the group consisting of —$CH_2$—, =CH—, —$CH_2$—$CH_2$—, —CH=CH—, —O—, —NH—, =N—, —S—, —$CH_2$N(-alkyl)-, —CH=N—, —$CH_2$O— and —$OCH_2$—;

each $R^6$ is independently from each other, selected from the group consisting of hydrogen, hydroxy, amino, nitro, cyano, halo, carboxyl, alkyl, phenyl, alkyloxy, phenyloxy, alkylcarbonyloxy, alkyloxycarbonyl, alkylthio, mono- and dialkylamino, alkylcarbonylamino, mono- and dialkylaminocarbonyl, mono- and dialkylaminocarbonyloxy, mono- and dialkylaminoalkyloxy, the alkyl and aryl radicals being optionally substituted with one or more hydroxy or halo atoms or amino groups; or
two vicinal radicals $R^6$ may be taken together to form a bivalent radical —$R^6$—$R^6$— selected from the group consisting of —$CH_2$—$CH_2$—O—, —O—$CH_2$—C(=O)—, —O—$CH_2$—O—, —$CH_2$—O—$CH_2$—, —O—$CH_2$—$CH_2$—O—, —CH=CH—CH=CH—, —CH=CH—CH=N—, —CH=CH—N=CH—, —CH=N—CH=CH—, —N=CH—CH=CH—, —$CH_2$—$CH_2$—$CH_2$—, —$CH_2$—$CH_2$—C(=O)— and —$CH_2$—$CH_2$—$CH_2$—$CH_2$—; and
$R^{10}$ is selected from the group consisting of hydrogen, alkyl, phenylalkyl and phenyl.

2. A compound according to claim 1 wherein that X=O or NH; $R^1$ and $R^2$ are both alkyloxy; m=1; Pir is a radical according to Formula (IIa) wherein $R^8$ is hydrogen and n=4; $R^3$ is a radical according to Formula (IIIb) wherein Z is =CH—, d is a double bond, A is a phenyl ring, $R^4$ is an alkyl and $R^{10}$ is hydrogen.

3. A pharmaceutically pure compound according to claims 1 which is suitable for use in a medicine.

4. A process for the treatment of a disorder selected from the group consisting of depression, anxiety and body weight disorders to a patient in need of said treatment comprising administering an effective amount of a compound of claim 1.

5. A pharmaceutical composition comprising a pharmaceutically acceptable carrier and, as active ingredient a therapeutically effective amount of a compound of claim 1.

6. A process for making a pharmaceutical composition comprising mixing a compound according to claim 1 and a pharmaceutically acceptable carrier.

7. A pharmaceutical composition comprising a pharmaceutically acceptable carrier and, as active ingredient a therapeutically effective amount of a compound according to claim 1 and one or more other compounds selected from the group consisting of antidepressants, anxiolytics and antipsychotics.

8. A process for the treatment of a patient in need of treatment comprising administering to the patient a therapeutically effective amount of a pharmaceutical composition in according to claim 7 for the treatment of a disorder selected from the group consisting of depression, anxiety and body weight disorders.

9. A process for the treatment of a disorder selected from the group consisting of depression, anxiety and body weight disorders comprising the simultaneous or sequential administration of a compound according to claim 1 and one or more other compounds selected from the group consisting of antidepressants, anxiolytics and antipsychotics.

10. A process for the treatment of a disorder selected from the group consisting of depression, anxiety and body weight disorders, said treatment comprising the simultaneous or sequential administration of one or more compounds selected from the group of antidepressants, anxiolytics and antipsychotics and a compound according to claim 2.

11. A process for making a pharmaceutical composition comprising mixing a compound according to claim 1 and a compound selected from the group consisting of antidepressants, anxiolytics and antipsychotics and a pharmaceutically acceptable carrier.

12. A process for preparing a compound according to claim 1 wherein a compound according to Formula (IV) is reacted with a compound according to Formula (V) under suitable conditions to yield the compound of Formula (VI)

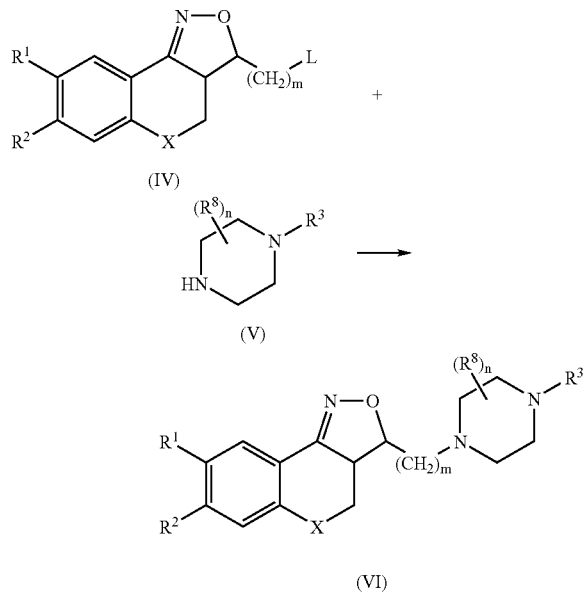

wherein
L is a leaving group
X is $CH_2$, N—$R^7$, S or O;
$R^7$ is selected from the group consisting of hydrogen, alkyl, phenyl, phenylalkyl, alkylcarbonyl, alkyloxycarbonyl and mono- and dialkylaminocarbonyl, the phenyl and alkyl groups being optionally substituted with one or more halo atoms;
$R^1$ and $R^2$ are each, independently from each other, selected from the group consisting of hydrogen, hydroxy, cyano, halo, $OSO_2H$, $OSO_2CH_3$, phenyl, phenylalkyl, alkyloxy, alkyloxyalkyloxy, alkyloxyalkyloxyalkyloxy, tetrahydrofuranyloxy, alkylcarbonyloxy, alkylthio, alkyloxyalkylcarbonyloxy, pyridinylcarbonyloxy, alkylcarbonyloxyalkyloxy, alkyloxycarbonyloxy, alkenyloxy, alkenylcarbonyloxy and mono- and dialkylaminoalkyloxy, the alkyl and aryl radicals being optionally substituted with one or more hydroxy or halo atoms or amino groups; or
$R^1$ and $R^2$ may be taken together to form a bivalent radical —$R^1$—$R^2$— selected from the group consisting of —$CH_2$—$CH_2$—O—, —O—$CH_2$—$CH_2$—, —O—$CH_2$—O—, —$CH_2$—O—$CH_2$— and —O—$CH_2$—$CH_2$—O—;
$(CH_2)_m$ is a straight hydrocarbon chain of m carbon atoms, m being an integer ranging from 1 to 4;
each $R^8$ is independently from each other, selected from the group consisting of hydrogen, hydroxy, amino, nitro, cyano, halo and alkyl;
n is an integer ranging from 1 to 5;
$R^3$ is a radical according to any one of Formula (III)

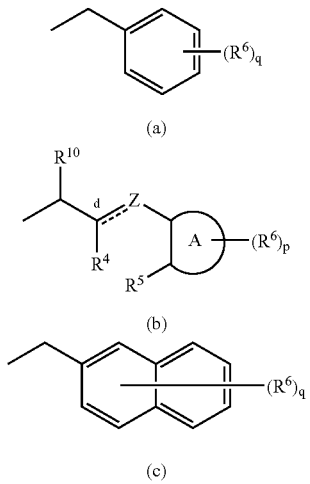

wherein:
d is a single bond while Z is a bivalent radical selected from the group consisting of —$CH_2$—, —C(=O)—, —CH(OH)—, —C(=N—OH)—, —CH(alkyl)-, —O—, —S—, —S(=O), and —NH—; or d is a double bond while Z is a trivalent radical of formula =CH— or =C(alkyl);
A is a 5- or 6-membered aromatic homocyclic or heterocyclic ring, selected from the group consisting of phenyl, pyranyl, pyridinyl, pyrazinyl, pyrimidinyl, pyridazinyl, thienyl, isothiazolyl, pyrrolyl, imidazolyl, pyrazolyl, furanyl, oxadiazolyl and isoxazolyl;
p is an integer ranging from 0 to 4;
q is an integer ranging from 0 to 7;
$R^4$ is selected from the group consisting of hydrogen, alkyl, phenyl, biphenyl, naphthyl, halo and cyano, the alkyl and aryl radicals being optionally substituted with one or more hydroxy or halo atoms or amino groups;
$R^5$ is equal to $R^4$; or
$R^4$ and $R^5$ may be taken together to form a bivalent radical —$R^4$—$R^5$— selected from the group consisting of —$CH_2$—, =CH—, —$CH_2$—$CH_2$—, —CH=CH—, —O—, —NH—, =N—, —S—, —$CH_2$N(-alkyl)-, —CH=N—, —$CH_2$O— and —O$CH_2$—;
each $R^6$ is independently from each other, selected from the group consisting of hydrogen, hydroxy, amino, nitro, cyano, halo, carboxyl, alkyl, phenyl, alkyloxy, phenyloxy, alkylcarbonyloxy, alkyloxycarbonyl, alkylthio, mono- and dialkylamino, alkylcarbonylamino, mono- and dialkylaminocarbonyl, mono- and dialkylaminocarbonyloxy, mono- and dialkylaminoalkyloxy, the alkyl and aryl radicals being optionally substituted with one or more hydroxy or halo atoms or amino groups; or
two vicinal radicals $R^6$ may be taken together to form a bivalent radical —$R^6$—$R^6$— selected from the group consisting of —$CH_2$—$CH_2$—O—, —O—$CH_2$—C(=O)—, —O—$CH_2$—O—, —$CH_2$—O—$CH_2$—, —O—$CH_2$—$CH_2$—O—, —CH=CH—CH=CH—, —CH=CH—CH=N—, —CH=CH—N=CH—, —CH=N—CH=CH—, —N=CH—CH=CH—, —$CH_2$—$CH_2$—$CH_2$—, —$CH_2$—$CH_2$—C(=O)— and —$CH_2$—$CH_2$—$CH_2$—$CH_2$—; and $R^{10}$ is selected from the group consisting of hydrogen, alkyl, phenylalkyl and phenyl.

13. A compound according to the general Formula (IV)

(IV)

wherein
L is a leaving group;
X is $CH_2$, $N-R^7$, S or O;
$R^7$ is selected from the group consisting of hydrogen, alkyl, phenyl, phenylalkyl, alkylcarbonyl, alkyloxycarbonyl and mono- and dialkylaminocarbonyl, the phenyl and alkyl groups being optionally substituted with one or more halo atoms;
$R^1$ and $R^2$ are each, independently from each other, selected from the group consisting of hydrogen, hydroxy, cyano, halo, $OSO_2H$, $OSO_2CH_3$, phenyl, phenylalkyl, alkyloxy, alkyloxyalkyloxy, alkyloxyalkyloxyalkyloxy, tetrahydrofuranyloxy, alkylcarbonyloxy, alkylthio, alkyloxyalkylcarbonyloxy, pyridinylcarbonyloxy, alkylcarbonyloxyalkyloxy, alkyloxycarbonyloxy, alkenyloxy, alkenylcarbonyloxy and mono- and dialkylaminoalkyloxy, the alkyl and aryl radicals being optionally substituted with one or more hydroxy or halo atoms or amino groups; or
$R^1$ and $R^2$ may be taken together to form a bivalent radical $-R^1-R^2-$ selected from the group consisting of $-CH_2-CH_2-O-$, $-O-CH_2-CH_2-$, $-O-CH_2-O-$, $-CH_2-O-CH_2-$ and $-O-CH_2-CH_2-O-$;
$(CH_2)_m$ is a straight hydrocarbon chain of m carbon atoms, m being an integer ranging from 1 to 4; and
excluding 3,3a,4,5-tetrahydronaphtho[1,2-c]isoxazole-3-acetic acid.

14. A compound according to the general Formula (VIII)

(VIII)

wherein
X is $CH_2$, $N-R^7$, S or O;
$R^7$ is selected from the group consisting of hydrogen, alkyl, phenyl, phenylalkyl, alkylcarbonyl, alkyloxycarbonyl and mono- and dialkylaminocarbonyl, the phenyl and alkyl groups being optionally substituted with one or more halo atoms;
$R^1$ and $R^2$ are each, independently from each other, selected from the group consisting of hydrogen, hydroxy, cyano, halo, $OSO_2H$, $OSO_2CH_3$, phenyl, phenylalkyl, alkyloxy, alkyloxyalkyloxy, alkyloxyalkyloxyalkyloxy, tetrahydrofuranyloxy, alkylcarbonyloxy, alkylthio, alkyloxyalkylcarbonyloxy, pyridinylcarbonyloxy, alkylcarbonyloxyalkyloxy, alkyloxycarbonyloxy, alkenyloxy, alkenylcarbonyloxy and mono- and dialkylaminoalkyloxy, the alkyl and aryl radicals being optionally substituted with one or more hydroxy or halo atoms or amino groups; or
$R^1$ and $R^2$ may be taken together to form a bivalent radical $-R^1-R^2-$ selected from the group consisting of $-CH_2-CH_2-O-$, $-O-CH_2-CH_2-$, $-O-CH_2-O-$, $-CH_2-O-CH_2-$ and $-O-CH_2-CH_2-O-$;
$(CH_2)_m$ is a straight hydrocarbon chain of m carbon atoms, m being an integer ranging from 1 to 4;
each $R^8$ is independently from each other, selected from the group consisting of hydrogen, hydroxy, amino, nitro, cyano, halo and alkyl; and
n is an integer ranging from 1 to 5.

15. A compound according to claim 13 wherein L is selected from the group of $OSO_2C_6H_4(CH_3)$, $OSO_2CH_3$, Cl, Br and I.

16. A process for preparing a compound according to claim 1 wherein a compound according to Formula (IV) is reacted with a compound according to Formula (VII) under suitable conditions to yield the compound of Formula (VIII)

(IV)

+

(VII)

→

(VIII)

L is a leaving group
X is $CH_2$, $N-R^7$, S or O;
$R^7$ is selected from the group consisting of hydrogen, alkyl, phenyl, phenylalkyl, alkylcarbonyl, alkyloxycarbonyl and mono- and dialkylaminocarbonyl, the phenyl and alkyl groups being optionally substituted with one or more halo atoms;
$R^1$ and $R^2$ are each, independently from each other, selected from the group consisting of hydrogen, hydroxy, cyano, halo, $OSO_2H$, $OSO_2CH_3$, phenyl, phenylalkyl, alkyloxy, alkyloxyalkyloxy, alkyloxyalkyloxyalkyloxy, tetrahydrofuranyloxy, alkylcarbonyloxy, alkylthio, alkyloxyalkylcarbonyloxy, pyridinylcarbonyloxy, alkylcarbonyloxyalkyloxy, alkyloxycarbonyloxy, alkenyloxy, alkenylcarbonyloxy and mono- and dialkylaminoalkyloxy, the alkyl and aryl radicals being optionally substituted with one or more hydroxy or halo atoms or amino groups; or $R^1$ and $R^2$ may be taken together to form a bivalent radical —$R^1$—$R^2$— selected from the group consisting of —CH$_2$—CH$_2$—O—, —O—CH$_2$—CH$_2$—, —O—CH$_2$—O—, —CH$_2$—O—CH$_2$— and —O—CH$_2$—CH$_2$—O—;

(CH$_2$)$_m$ is a straight hydrocarbon chain of m carbon atoms, m being an integer ranging from 1 to 4;

each $R^8$ is independently from each other, selected from the group consisting of hydrogen, hydroxy, amino, nitro, cyano, halo and alkyl; and n is an integer ranging from 1 to 5.

\* \* \* \* \*